United States Patent
Kang et al.

(10) Patent No.: US 9,492,237 B2
(45) Date of Patent: Nov. 15, 2016

(54) METHOD AND APPARATUS FOR CONTROLLING A HAPTIC DEVICE

(75) Inventors: Hyosig Kang, Weston, FL (US); Dennis Moses, Doral, FL (US); Arthur Quaid, Ft. Lauderdale, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 794 days.

(21) Appl. No.: 11/750,815

(22) Filed: May 18, 2007

(65) Prior Publication Data

US 2007/0270685 A1 Nov. 22, 2007

Related U.S. Application Data

(60) Provisional application No. 60/801,378, filed on May 19, 2006.

(51) Int. Cl.
*G01C 9/00* (2006.01)
*G01C 17/00* (2006.01)
(Continued)

(52) U.S. Cl.
CPC ........... *A61B 34/20* (2016.02); *A61B 19/5244* (2013.01); *A61B 34/30* (2016.02); *A61B 34/71* (2016.02); *A61B 34/76* (2016.02); *A61B 17/1764* (2013.01); *A61B 34/25* (2016.02); *A61B 90/03* (2016.02); *A61B 2017/00119* (2013.01); *A61B 2017/00694* (2013.01); *A61B 2017/00712* (2013.01); *A61B 2017/00725* (2013.01); *A61B 2034/102* (2016.02); *A61B 2034/107* (2016.02); *A61B 2034/108* (2016.02); *A61B 2034/207* (2016.02);
(Continued)

(58) Field of Classification Search
CPC .................. A61B 19/5244; A61B 19/2203
USPC .......... 702/85, 94, 95, 97, 150–155; 606/45, 606/80, 130; 600/300, 423, 424
See application file for complete search history.

(56) References Cited

U.S. PATENT DOCUMENTS 4,747,393 A 5/1988 Medwid
4,903,536 A 2/1990 Salisbury, Jr. et al.
(Continued)

FOREIGN PATENT DOCUMENTS

CN 1684729 10/2005
EP 1 059 067 A1 12/2000
(Continued)

OTHER PUBLICATIONS

Argenson, Jean-Nöel A. et al., "Is There a Place for Patellofemoral Arthroplasty?", Clinical Orthopaedics and Related Research, No. 321, 1995, pp. 162-167.
(Continued)

*Primary Examiner* — Michael Nghiem
(74) *Attorney, Agent, or Firm* — Foley & Lardner LLP

(57) ABSTRACT

A method for calibrating a surgical device is provided. The method includes acquiring first data including a position and/or an orientation of a first object disposed on the surgical device at a first location; acquiring second data including a position and/or an orientation of a second object disposed on the surgical device at a second location; determining third data including a position and/or an orientation of the first object relative to the second location; and determining a position and/or an orientation of the second object relative to the second location based at least in part on the first data, the second data, and the third data.

18 Claims, 21 Drawing Sheets

(51) Int. Cl.
  *G01C 19/00* (2013.01)
  *A61B 19/00* (2006.01)
  *A61B 17/17* (2006.01)
  *A61B 17/00* (2006.01)

(52) U.S. Cl.
  CPC *A61B 2034/2055* (2016.02); *A61B 2034/2059* (2016.02); *A61B 2034/2065* (2016.02); *A61B 2034/2068* (2016.02); *A61B 2034/305* (2016.02); *A61B 2090/363* (2016.02); *A61B 2090/364* (2016.02); *A61B 2090/3983* (2016.02)

(56) References Cited

U.S. PATENT DOCUMENTS

| | | |
|---|---|---|
| 4,979,949 A | 12/1990 | Matsen et al. |
| 5,046,375 A | 9/1991 | Salisbury et al. |
| 5,086,401 A | 2/1992 | Glassman et al. |
| 5,142,930 A | 9/1992 | Allen et al. |
| 5,154,717 A | 10/1992 | Matsen et al. |
| 5,207,114 A | 5/1993 | Salisbury et al. |
| 5,230,338 A | 7/1993 | Allen et al. |
| 5,236,432 A | 8/1993 | Matsen et al. |
| 5,299,288 A | 3/1994 | Glassman et al. |
| 5,343,385 A | 8/1994 | Joskowicz et al. |
| 5,388,480 A | 2/1995 | Townsend |
| 5,399,951 A | 3/1995 | Lavallee et al. |
| 5,408,409 A | 4/1995 | Glassman et al. |
| 5,445,144 A | 8/1995 | Wodicka et al. |
| 5,445,166 A | 8/1995 | Taylor |
| 5,452,941 A | 9/1995 | Halse et al. |
| 5,551,429 A | 9/1996 | Fitzpatrick et al. |
| 5,572,999 A | 11/1996 | Funda et al. |
| 5,576,727 A | 11/1996 | Rosenberg et al. |
| 5,587,937 A | 12/1996 | Massie et al. |
| 5,611,353 A | 3/1997 | Dance et al. |
| 5,625,576 A | 4/1997 | Massie et al. |
| 5,630,431 A | 5/1997 | Taylor |
| 5,638,819 A | 6/1997 | Manwaring et al. |
| 5,676,673 A | 10/1997 | Ferre et al. |
| 5,682,886 A | 11/1997 | Delp et al. |
| 5,688,280 A | 11/1997 | Booth et al. |
| 5,694,013 A | 12/1997 | Stewart et al. |
| 5,695,500 A | 12/1997 | Taylor et al. |
| 5,701,140 A | 12/1997 | Rosenberg et al. |
| 5,704,791 A | 1/1998 | Gillio |
| 5,727,554 A | 3/1998 | Kalend et al. |
| 5,766,016 A | 6/1998 | Sinclair et al. |
| 5,769,640 A | 6/1998 | Jacobus et al. |
| 5,792,147 A | 8/1998 | Evans et al. |
| 5,799,055 A | 8/1998 | Peshkin et al. |
| 5,806,518 A | 9/1998 | Mittelstadt |
| 5,831,408 A | 11/1998 | Jacobus et al. |
| 5,855,553 A | 1/1999 | Tajima et al. |
| 5,871,018 A | 2/1999 | Delp et al. |
| 5,887,121 A | 3/1999 | Funda et al. |
| 5,888,220 A | 3/1999 | Felt et al. |
| 5,898,599 A | 4/1999 | Massie et al. |
| 5,928,137 A | 7/1999 | Green |
| 5,950,629 A | 9/1999 | Taylor et al. |
| 5,971,997 A | 10/1999 | Guthrie et al. |
| 5,976,156 A | 11/1999 | Taylor et al. |
| 5,978,696 A | 11/1999 | VomLehn et al. |
| 5,980,535 A | 11/1999 | Barnett et al. |
| 5,984,930 A | 11/1999 | Maciunas et al. |
| 5,987,960 A | 11/1999 | Messner et al. |
| 6,002,859 A | 12/1999 | DiGioia, III et al. |
| 6,006,126 A | 12/1999 | Cosman |
| 6,006,127 A | 12/1999 | Van Der Brug et al. |
| 6,017,305 A | 1/2000 | Bonutti |
| 6,033,415 A | 3/2000 | Mittelstadt et al. |
| 6,084,587 A | 7/2000 | Tarr et al. |
| 6,104,158 A | 8/2000 | Jacobus et al. |
| 6,109,270 A | 8/2000 | Mah et al. |
| 6,111,577 A | 8/2000 | Zilles et al. |
| 6,113,395 A | 9/2000 | Hon |
| 6,147,674 A | 11/2000 | Rosenberg et al. |
| 6,161,032 A | 12/2000 | Acker |
| 6,188,728 B1 | 2/2001 | Hurst |
| 6,191,796 B1 | 2/2001 | Tarr |
| 6,205,411 B1 | 3/2001 | DiGioia, III et al. |
| 6,219,032 B1 | 4/2001 | Rosenberg et al. |
| 6,223,100 B1 | 4/2001 | Green |
| 6,226,566 B1 | 5/2001 | Funda et al. |
| 6,228,089 B1 | 5/2001 | Wahrburg |
| 6,231,526 B1 | 5/2001 | Taylor et al. |
| 6,233,504 B1 | 5/2001 | Das et al. |
| 6,259,806 B1 | 7/2001 | Green |
| 6,285,902 B1 | 9/2001 | Kienzle et al. |
| 6,288,705 B1 | 9/2001 | Rosenberg et al. |
| 6,292,174 B1 | 9/2001 | Mallett et al. |
| 6,300,936 B1 | 10/2001 | Braun et al. |
| 6,322,467 B1 | 11/2001 | Hook et al. |
| 6,322,567 B1 | 11/2001 | Mittelstadt et al. |
| 6,325,808 B1 | 12/2001 | Bernard et al. |
| 6,337,994 B1 | 1/2002 | Stoianovici et al. |
| 6,366,273 B1 | 4/2002 | Rosenberg et al. |
| 6,369,834 B1 | 4/2002 | Zilles et al. |
| 6,377,011 B1 | 4/2002 | Ben-Ur |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,393,340 B2 | 5/2002 | Funda et al. |
| 6,405,072 B1 | 6/2002 | Cosman |
| 6,405,158 B1 | 6/2002 | Massie et al. |
| 6,417,638 B1 | 7/2002 | Guy et al. |
| 6,421,048 B1 | 7/2002 | Shih et al. |
| 6,424,885 B1 | 7/2002 | Niemeyer et al. |
| 6,430,434 B1 | 8/2002 | Mittelstadt |
| 6,434,416 B1 | 8/2002 | Mizoguchi et al. |
| 6,443,894 B1 | 9/2002 | Sumanaweera et al. |
| 6,466,815 B1 | 10/2002 | Saito et al. |
| 6,468,265 B1 | 10/2002 | Evans et al. |
| 6,493,608 B1 | 12/2002 | Niemeyer |
| 6,494,039 B2 | 12/2002 | Pratt et al. |
| 6,533,737 B1 | 3/2003 | Brosseau et al. |
| 6,546,277 B1 | 4/2003 | Franck et al. |
| 6,547,782 B1 | 4/2003 | Taylor |
| 6,551,325 B2 | 4/2003 | Neubauer et al. |
| 6,552,722 B1 | 4/2003 | Shih et al. |
| 6,583,161 B1 | 6/2003 | Medina |
| 6,642,686 B1 | 11/2003 | Ruch |
| 6,671,651 B2 | 12/2003 | Goodwin et al. |
| 6,674,916 B1 | 1/2004 | Deman et al. |
| 6,690,964 B2 | 2/2004 | Bieger et al. |
| 6,692,485 B1 | 2/2004 | Brock et al. |
| 6,701,174 B1 | 3/2004 | Krause et al. |
| 6,704,694 B1 | 3/2004 | Basdogan et al. |
| 6,711,431 B2 | 3/2004 | Sarin et al. |
| 6,711,432 B1 | 3/2004 | Krause et al. |
| 6,748,819 B2 | 6/2004 | Maeguchi et al. |
| 6,750,877 B2 | 6/2004 | Rosenberg et al. |
| 6,757,582 B2 | 6/2004 | Brisson et al. |
| 6,778,850 B1 | 8/2004 | Adler et al. |
| 6,785,572 B2 | 8/2004 | Yanof et al. |
| 6,786,896 B1 | 9/2004 | Madhani et al. |
| 6,801,801 B1 | 10/2004 | Sati |
| 6,810,281 B2 | 10/2004 | Brock et al. |
| 6,816,148 B2 | 11/2004 | Mallett et al. |
| 6,831,640 B2 | 12/2004 | Shih et al. |
| 6,850,794 B2 | 2/2005 | Shahidi |
| 6,853,965 B2 | 2/2005 | Massie et al. |
| 6,859,661 B2 | 2/2005 | Tuke |
| 6,877,239 B2 | 4/2005 | Leitner et al. |
| 6,894,678 B2 | 5/2005 | Rosenberg et al. |
| 6,920,347 B2 | 7/2005 | Simon et al. |
| 6,985,133 B1 | 1/2006 | Rodomista et al. |
| 6,987,504 B2 | 1/2006 | Rosenberg et al. |
| 7,001,346 B2 | 2/2006 | White |
| 7,035,716 B2 | 4/2006 | Harris et al. |
| 7,039,866 B1 | 5/2006 | Rosenberg et al. |
| 7,131,073 B2 | 10/2006 | Rosenberg et al. |
| 7,168,042 B2 | 1/2007 | Braun et al. |

(56) References Cited

U.S. PATENT DOCUMENTS

| | | |
|---|---|---|
| 7,199,790 B2 | 4/2007 | Rosenberg et al. |
| 7,206,626 B2 | 4/2007 | Quaid, III |
| 7,206,627 B2 | 4/2007 | Abovitz et al. |
| 7,491,198 B2 | 2/2009 | Kockro |
| 7,660,623 B2 | 2/2010 | Hunter et al. |
| 7,742,804 B2 | 6/2010 | Faul |
| 7,747,311 B2 | 6/2010 | Quaid, III |
| 7,774,044 B2 | 8/2010 | Sauer et al. |
| 7,831,292 B2 | 11/2010 | Quaid et al. |
| 2001/0034530 A1 | 10/2001 | Malackowski et al. |
| 2001/0037064 A1 | 11/2001 | Shahidi |
| 2001/0039422 A1 | 11/2001 | Carol et al. |
| 2001/0041838 A1 | 11/2001 | Holupka et al. |
| 2002/0082498 A1 | 6/2002 | Wendt et al. |
| 2002/0107521 A1 | 8/2002 | Petersen et al. |
| 2002/0108054 A1 | 8/2002 | Moore et al. |
| 2002/0120188 A1 | 8/2002 | Brock et al. |
| 2002/0133174 A1 | 9/2002 | Charles et al. |
| 2003/0093103 A1 | 5/2003 | Malackowski et al. |
| 2003/0112281 A1 | 6/2003 | Sriram et al. |
| 2003/0187351 A1 | 10/2003 | Franck et al. |
| 2003/0209096 A1 | 11/2003 | Pandey et al. |
| 2004/0009459 A1 | 1/2004 | Anderson et al. |
| 2004/0012806 A1 | 1/2004 | Murata |
| 2004/0024311 A1 | 2/2004 | Quaid, III |
| 2004/0034282 A1 | 2/2004 | Quaid, III |
| 2004/0034283 A1 | 2/2004 | Quaid, III |
| 2004/0034302 A1 | 2/2004 | Abovitz et al. |
| 2004/0102866 A1 | 5/2004 | Harris et al. |
| 2004/0106916 A1* | 6/2004 | Quaid et al. ............ 606/1 |
| 2004/0115606 A1 | 6/2004 | Davies |
| 2004/0127788 A1 | 7/2004 | Arata |
| 2004/0128026 A1 | 7/2004 | Harris et al. |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0013477 A1 | 1/2005 | Ratti et al. |
| 2005/0062738 A1 | 3/2005 | Handley et al. |
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0137599 A1 | 6/2005 | Masini |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0215879 A1 | 9/2005 | Chuanggui |
| 2005/0215888 A1* | 9/2005 | Grimm ............ A61B 19/54 600/426 |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0109266 A1 | 5/2006 | Itkowitz et al. |
| 2006/0133827 A1 | 6/2006 | Becouarn et al. |
| 2006/0142657 A1* | 6/2006 | Quaid et al. ............ 600/424 |
| 2006/0265179 A1* | 11/2006 | Jansen ............ G01B 21/042 702/157 |
| 2006/0293598 A1 | 12/2006 | Fraser |
| 2007/0142751 A1* | 6/2007 | Kang et al. ............ 600/587 |
| 2007/0260140 A1 | 11/2007 | Solar et al. |
| 2008/0004633 A1 | 1/2008 | Arata et al. |
| 2008/0010705 A1 | 1/2008 | Quaid et al. |
| 2008/0010706 A1 | 1/2008 | Moses et al. |
| 2008/0058945 A1 | 3/2008 | Hajaj et al. |
| 2009/0000626 A1* | 1/2009 | Quaid et al. ............ 128/898 |
| 2009/0000627 A1* | 1/2009 | Quaid et al. ............ 128/898 |
| 2009/0012531 A1* | 1/2009 | Quaid et al. ............ 606/130 |
| 2009/0012532 A1* | 1/2009 | Quaid et al. ............ 606/130 |

FOREIGN PATENT DOCUMENTS

| | | |
|---|---|---|
| EP | 1 184 684 A2 | 3/2002 |
| EP | 1380266 | 1/2004 |
| EP | 1 871 267 | 1/2008 |
| EP | 1 574 186 | 6/2008 |
| JP | 08-215211 A | 8/1996 |
| JP | 09-330016 A | 12/1997 |
| JP | 2000-279425 A | 10/2000 |
| JP | 2002-102251 | 4/2002 |
| JP | 2003-053684 | 2/2003 |
| JP | 2004-513684 | 5/2004 |
| WO | WO-95/01757 A | 1/1995 |
| WO | WO-96/17552 A1 | 6/1996 |
| WO | WO-00/35336 A2 | 6/2000 |
| WO | WO-02/24051 A2 | 3/2002 |
| WO | WO-02/060653 A2 | 8/2002 |
| WO | WO 02/061371 | 8/2002 |
| WO | WO 02/061688 | 8/2002 |
| WO | WO 03/077101 A2 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO 2004/070577 A2 | 8/2004 |
| WO | WO-2004/070580 A2 | 8/2004 |
| WO | WO-2004/070581 A2 | 8/2004 |
| WO | WO-2004/075987 | 9/2004 |
| WO | WO-2005/009215 A | 2/2005 |
| WO | WO 2005-72629 | 8/2005 |
| WO | WO-2005/072629 | 8/2005 |
| WO | WO 2005/120380 A1 | 12/2005 |
| WO | WO 2005/122916 A1 | 12/2005 |
| WO | WO-2006/004894 A2 | 1/2006 |
| WO | WO-2006/091494 A1 | 8/2006 |
| WO | WO-2007/117297 A2 | 10/2007 |

OTHER PUBLICATIONS

Arciero, Robert A. et al., "Patellofemoral Arthroplasty, a Three-to Nine-Year Follow-up Study", Clinical Orthopaedics and Related Research, No. 236, Nov. 1988, pp. 60-71.

Kanazides, Peter et al., "An Integrated System for Cementless Hip Replacement", Integrated Surgical Systems Department of Orthopedic Surgery, Sutter General Hospital, May/Jun. 1995, pp. 307-313.

Taylor, Russell et al., "An Image-Directed Robotic System for Precise Orthopaedic Surgery", IEEE Transactions on Robotics and Automation, vol. 10, No. 3, Jun. 1994, pp. 261-275.

Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.

Taylor, Russell et al., "Robotic Joint Replacement Surgery", NSF Engineering Research Center for Computer-Integrated Surgical Systems and Technology, 2000, 2001, 2004.

U.S. Appl. No. 10/357,197, filed Feb. 21, 2006, Quaid et al.
U.S. Appl. No. 10/384,072, filed Mar. 6, 2003, Quaid, III.
U.S. Appl. No. 10/384,077, filed Mar. 6, 2003, Abovitz et al.
U.S. Appl. No. 10/384,078, filed Mar. 6, 2003, Quaid, III.
U.S. Appl. No. 10/384,194, filed Mar. 6, 2003, Quaid, III.
U.S. Appl. No. 10/621,119, filed Jul. 16, 2003, Quaid et al.
U.S. Appl. No. 11/646,204, filed Dec. 27, 2006, Kang et al.
U.S. Appl. No. 12/144,496, filed Jun. 23, 2008, Quaid et al.
U.S. Appl. No. 12/144,507, filed Jun. 23, 2008, Quaid et al.
U.S. Appl. No. 12/144,517, filed Jun. 23, 2008, Quaid et al.
U.S. Appl. No. 12/144,526, filed Jun. 23, 2008, Quaid et al.
U.S. Appl. No. 12/698,353, filed Feb. 2, 2010, Quaid, III.

Abovitz et al., "The Future Use of Networked Haptic Learning Information Systems in Computer-Assisted Surgery," CAOS 2001, Jul. 6-8, 2001, pp. 337-338.

Abovitz, "Digital surgery: the future of medicine and human-robot symbiotic interaction," Industrial Robot: An International Journal, Oct. 2001, vol. 28, Issue 5, pp. 401-406 (abstract only).

(56) References Cited

OTHER PUBLICATIONS

Abovitz, "Human-Interactive Medical Robotics," CAOS 2000, Jun. 15-17, 2000, pp. 71-72.
Abovitz, "Human-Interactive Medical Robotics," CAOS 2001, Jul. 6-8, 2001, pp. 81-82.
Advisory Action for U.S. Appl. No. 10/384,078, mail date Mar. 1, 2010, 3 pages.
Advisory Action for U.S. Appl. No. 10/384,194, mail date May 22, 2009, 3 pages.
Advisory Action for U.S. Appl. No. 10/621,119, mail date Sep. 17, 2008, 3 pages.
Appeal Brief for U.S. Appl. No. 10/384,078, submitted Apr. 22, 2010, 42 pages.
Applicant's response to 1st Office Action for Chinese Application No. 200680012488.3, submitted May 14, 2010 (10 pages).
Applicant's response to 2nd Office Action for Chinese Application No. 200680012488.3, submitted Dec. 7, 2010 (3 pages).
Applicant's Pre-Appeal Brief Conference Request for U.S. Appl. No. 10/384,078, submitted Feb. 25, 2010, 5 pages.
Applicant's request under Rule 48 correcting inventorship for U.S. Appl. No. 11/357,197, submitted Apr. 15, 2011, 2 pages.
Applicant's response to Final Office Action for U.S. Appl. No. 12/144,526, submitted Mar. 15, 2011.
Applicant's response to non-final Office Action for U.S. Appl. No. 12/144,507, submitted Sep. 15, 2010.
Applicant's response to non-final Office Action for U.S. Appl. No. 12/144,517, submitted Sep. 8, 2010.
Applicant's response to non-final Office Action for U.S. Appl. No. 12/144,526, submitted Jul. 29, 2010.
Applicant's response to Office Action for U.S. Appl. No. 10/384,072, submitted Aug. 21, 2006, 14 pages.
Applicant's response to Office Action for U.S. Appl. No. 10/384,077, submitted Aug. 21, 2006, 22 pages.
Applicant's response to Office Action for U.S. Appl. No. 10/384,078, submitted Apr. 25, 2008, 10 pages.
Applicant's response to Office Action for U.S. Appl. No. 10/384,078, submitted Feb. 15, 2010, 14 pages.
Applicant's response to Office Action for U.S. Appl. No. 10/384,078, submitted Jan. 7, 2009, 12 pages.
Applicant's response to Office Action for U.S. Appl. No. 10/384,078, submitted Jul. 8, 2009, 17 pages.
Applicant's response to Office Action for U.S. Appl. No. 10/384,078, submitted Mar. 29, 2011, 16 pages.
Applicant's response to Office Action for U.S. Appl. No. 10/384,078, submitted Oct. 19, 2010, 16 pages.
Applicant's response to Office Action for U.S. Appl. No. 10/384,194, submitted Feb. 2, 2010, 13 pages.
Applicant's response to Office Action for U.S. Appl. No. 10/384,194, submitted Jun. 1, 2009, 20 pages.
Applicant's response to Office Action for U.S. Appl. No. 10/384,194, submitted May 1, 2009, 20 pages.
Applicant's response to Office Action for U.S. Appl. No. 10/384,194, submitted Nov. 18, 2008, 19 pages.
Applicant's response to Office Action for U.S. Appl. No. 10/621,119, submitted Apr. 30, 2010, 19 pages.
Applicant's response to Office Action for U.S. Appl. No. 10/621,119, submitted Aug. 8, 2008, 24 pages.
Applicant's response to Office Action for U.S. Appl. No. 10/621,119, submitted Dec. 4, 2007, 19 pages.
Applicant's response to Office Action for U.S. Appl. No. 10/621,119, submitted Mar. 9, 2009, 20 pages.
Applicant's response to Office Action for U.S. Appl. No. 10/621,119, submitted Nov. 13, 2009, 19 pages.
Applicant's response to Office Action for U.S. Appl. No. 10/621,119, submitted Oct. 2, 2006, 25 pages.
Applicant's response to Office Action for U.S. Appl. No. 10/621,119, submitted Sep. 14, 2006, 23 pages.
Applicant's response to Office Action for U.S. Appl. No. 11/357,197, submitted Apr. 15, 2011, 20 pages.
Applicant's response to Office Action for U.S. Appl. No. 11/357,197, submitted Jan. 31, 2011, 29 pages.
Applicant's response to Office Action for U.S. Appl. No. 11/750,840, submitted May 16, 2011, 11 pages.
Bennett et al., "Autonomous Calibration of Single-Loop Kinematic Chains Formed by Manipulators With Passive End-Point Constraints," IEEE Transactions on Robotics and Automation, vol. 7, pp. 597-606, 1991.
Bettini, A., et al., "Vision Assisted Control for Manipulation Using Virtual Fixtures," proceedings of the 2001 Institute of Electrical and Electronics Engineers International Conference on Intelligent Robots and Systems, Oct. 29-Nov. 3, 2001, pp. 1171-1176.
Chapter II Demand and Response to Written Opinion for PCT/US2006/005700, submitted Dec. 15, 2006 (16 pages).
Chapter II Demand and Response to Written Opinion for PCT/US2006/049216, submitted Jul. 15, 2008.
Cobb et al., "A robotic system for TKR surgery," in Third Annual North American Program on Computer Assisted Orthopaedic Surgery, (Pittsburgh, PA), pp. 71-74, Jun. 1999.
Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.
English translation of first Office Action for corresponding Chinese Application No. 200680012488.3, dated Jan. 15, 2010 (6 pages).
Examination report for EP 04757075.9, dated Jan. 12, 2011.
Examiner Interview Summary Record for U.S. Appl. No. 10/384,078, mail date Oct. 15, 2010, 3 pages.
Goswami, et al., "Complete Parameter Identification of a Robot Using Partial Pose Information," IEEE Control Systems Magazine, Oct. 1993.
Ho, S.C. et al., "Robot Assisted Knee Surgery Establishing a Force Control Strategy Incorporating Active Motion Constraint," IEEE Engineering in Medicine and Biology Magazine, vol. 14, No. 3, May 1, 1995, col. 2-3, p. 293.
Hollerbach, J.M. & D. E. Johnson. Virtual Environment Rendering. To appear in Human and Machine Haptics, M. Cutkosky, R. Howe, K. Salisbury, and M. Srinivasan (eds.), MIT Press, 2000 (available at http://www.cs.ubc.ca/labs/spin/publications/related/hollerbach00.pdf).
International Preliminary Report for PCT/US2003/007063, dated Sep. 2, 2004 (2 pages).
International Preliminary Report on Patentability for PCT/US2004/022978 including International Search Report and Written Opinion, dated Feb. 13, 2007, (6 pages).
International Preliminary Report on Patentability for PCT/US2006/005700, dated May 8, 2007 (7 pages).
International Preliminary Report on Patentability for PCT/US2006/049216, dated Sep. 10, 2008.
International Search Report and Written Opinion for corresponding PCT Application No. PCT/US2006/049216, dated May 8, 2008 (7 pgs.).
International Search Report and Written Opinion for PCT/US2006/005700, dated Jun. 27, 2006.
International Search Report for PCT/US2003/007063, dated Apr. 16, 2004 (7 pages).
Leeser et al., "Computerassisted teach and play: Novel user-friendly robot teach mode using gravity compensation and backdrivability," in Proceedings of the Robotics International/SME Fifth World Conference in Robotics Research, (Cambridge, MA), Sep. 1994.
Meggiolaro, et al., "Manipulator calibration using a single endpoint contact constraint," in 26th ASME Bienniel Mechanisms Conference, (Baltimore, MD), 2000.
Notice of Allowance and Examiner Interview Summary Record for U.S. Appl. No. 10/621,119, mail date Jun. 11, 2010, 9 pages.
Notice of Allowance for U.S. Appl. No. 10/384,072, mail date Dec. 21, 2006, 7 pages.
Notice of Allowance for U.S. Appl. No. 10/384,077, mail date Dec. 14, 2006, 8 pages.
Notice of Allowance for U.S. Appl. No. 10/384,194, mail date Apr. 15, 2010, 4 pages.

(56) References Cited

OTHER PUBLICATIONS

Notice of Appeal and Pre-Appeal Brief Request for Review filed in response to Final Office Action for U.S. Appl. No. 12/144,507, submitted Mar. 22, 2011.
Notice of Appeal and Pre-Appeal Brief Request for Review filed in response to Final Office Action for U.S. Appl. No. 12/144,517, submitted Mar. 22, 2011.
Notice of Non-Compliant or Non-Responsive Amendment for U.S. Appl. No. 10/621,119, mail date Sep. 20, 2006, 2 pages.
Office Action for U.S. Appl. No. 10/384,072, mail date May 18, 2006, 6 pages.
Office Action for U.S. Appl. No. 10/384,077, mail date Jun. 1, 2006, 8 pages.
Office Action for U.S. Appl. No. 10/384,078, mail date Apr. 9, 2009, 13 pages.
Office Action for U.S. Appl. No. 10/384,078, mail date Dec. 30, 2010, 21 pages.
Office Action for U.S. Appl. No. 10/384,078, mail date Feb. 4, 2008, 9 pages.
Office Action for U.S. Appl. No. 10/384,078, mail date Jul. 20, 2010, 12 pages.
Office Action for U.S. Appl. No. 10/384,078, mail date Nov. 25, 2009, 14 pages.
Office Action for U.S. Appl. No. 10/384,078, mail date Oct. 7, 2008, 8 pages.
Office Action for U.S. Appl. No. 10/384,194, mail date Jun. 18, 2008, 2010, 9 pages.
Office Action for U.S. Appl. No. 10/384,194, mail date Mar. 2, 2009, 2010, 11 pages.
Office Action for U.S. Appl. No. 10/384,194, mail date Nov. 2, 2009, 8 pages.
Office Action for U.S. Appl. No. 10/621,119, mail date Dec. 10, 2008, 10 pages.
Office Action for U.S. Appl. No. 10/621,119, mail date Feb. 3, 2010, 12 pages.
Office Action for U.S. Appl. No. 10/621,119, mail date Jun. 16, 2006, 6 pages.
Office Action for U.S. Appl. No. 10/621,119, mail date Jun. 9, 2008, 9 pages.
Office Action for U.S. Appl. No. 10/621,119, mail date Sep. 29, 2009, 9 pages.
Office Action for U.S. Appl. No. 10/621,119, mail date Sep. 4, 2007, 8 pages.
Office Action for U.S. Appl. No 11/357,197, mail date Apr. 12, 2011, 9 pages.
Office Action for U.S. Appl. No. 11/357,197, mail date Sep. 29, 2010, 8 pages.
Office Action for U.S. Appl. No. 11/646,204, mail date Apr. 19, 2011, 7 pages.
Office Action for U.S. Appl. No. 12/144,507, mail date Jun. 17, 2010, 7 pages.
Office Action for U.S. Appl. No. 12/144,507, mail date Nov. 22, 2010, 9 pages.
Office Action for U.S. Appl. No. 12/144,517, mail date Jun. 9, 2010, 7 pages.
Office Action for U.S. Appl. No. 12/144,517, mail date Nov. 22, 2010, 8 pages.
Office Action for U.S. Appl. No. 12/144,526, mail date Apr. 29, 2010, 9 pages.
Office Action for U.S. Appl. No. 12/144,526, mail date Nov. 15, 2010, 11 pages.
Office Action with English translation for Chinese Application No. 200480023380.5, dated Jan. 23, 2009 (12 pages).
Office Action with English translation for Chinese Application No. 200480023380.5, dated Jul. 4, 2008 (9 pages).
Office Action with English translation for Japanese Application No. 2006-520381, dated May 19, 2010 (8 pages).
Office Action with English translation for Japanese Application No. 2006-520381, dated Nov. 18, 2010 (8 pages).
Office Action with English translation for Japanese Application No. 2008-551271, dated May 18, 2011 (6 pages).
Park et al., "Virtual fixtures for robotic cardiac surgery," in Proc. Medical Image Computing and Computer-Assisted Intervention, (Utrecht, Netherlands), Oct. 2001.
PCT/US2006/049216, Partial Intl. Search Report, Jan. 18, 2008 (2 pgs.).
Pre-Appeal Brief Conference Request for U.S. Appl. No. 10/621,119, submitted Oct. 9, 2008, 6 pages.
Pre-Appeal Conference Decision for U.S. Appl. No. 10/384,078, mail date Mar. 15, 2010, 2 pages.
Quaid et al., "Haptic Information Displays for Computer-Assisted Surgery," Proceedings of the 2002 IEEE International Conference on Robotics & Automation, May 2002, pp. 2092-2097.
Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.
Roche, "Changing the way surgeons plan and execute minimally invasive unicompartmental knee surgery," Orthopaedic Product News, pp. 16-18, Jul./Aug. 2006.
Rosenberg, Virtual Fixtures: Perceptual overlays enhance operator performance in telepresence tasks. PhD thesis, Stanford University, Aug. 1994.
Second Office Action and English translation for corresponding Chinese Application No. 200680012488.2, dated Oct. 12, 2010 (10 pages).
Terminal Disclaimer for U.S. Appl. No. 10/384,078, submitted Mar. 30, 2011, 1 pages.
Terminal Disclaimer Review Decision for U.S. Appl. No. 10/384,078, mailed Apr. 14, 2011, 1 page.
Townsend et al., "Teleoperator slave—WAM design methodology," Industrial Robot, vol. 26, No. 3, pp. 167-177, 1999.
U.S. Appl. No. 11/750,807, filed May 18, 2007, Arata et al.
U.S. Appl. No. 11/750,840, filed May 18, 2007, Quaid et al.
U.S. Appl. No. 11/750,845, filed May 18, 2007, Moses et al.
Applicant's response to Office Action for U.S. Appl. No. 11/750,840, submitted Oct. 21, 2010, 5 pages.
Office Action for U.S. Appl. No. 11/750,840, mailed Jul. 23, 2010, 17 pages.
Office Action for U.S. Appl. No. 11/750,840, mailed Nov. 16, 2010, 10 pages.
Acosta, et al., "Development of a Haptic Virtual Environment", Computer-Based Medical Systems, Proceedings 12th IEEE Symposium. pp. 35-39, 1999.
Bettini et al., "Vision assisted control for manipulation using virtual fixtures: Experiments at macro and micro scales," in Proc. 2002 IEEE Intl. Conf. on Robotics and Automation, (Washington, DC), May 2002.
Chen et al., "Force Feedback for Surgical Simulation," Proceedings of the IEEE, New York, US, vol. 86, No. 3, Mar. 1, 1998. pp. 524-530.
Colgate, J. Edward, et al., "Cobots: Robots for Collaboration with Human Operators," proceedings of International Mechanical Engineering Congress & Exhibition, DSC-vol. 58, 1996, pp. 433-439.
Davies et al, "Acrobot-using Robots and Surgeons Synergistically in Knee Surgery", 1997 British Crown Copyright, 173-178.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "'Acrobot' capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Moore, Carl A., et al., "Cabot Implementation of 3D Virtual Surfaces," proceedings of the 2002 Institute of Electrical and Electronics Engineers International Conference on Robotics & Automation, May 2002, pp. 3242-3247.
Niki, et al., "Simple Haptic Display and Object Data Design", Proceedings of the 2000 IEEE/RSJ International Conference on Intelligent Robots and Systems, pp. 967-972, 2000.

(56) References Cited

OTHER PUBLICATIONS

Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Press Release, "The Acrobot Company Wins Best Surgical Innovation Award," Acrobot Precision Surgical Systems, May 24, 2002, 1 page.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Rosenberg, "Virtual Fixtures: Perceptual Tools for Telerobotic Manipulation", 1993 IEEE, 76-82.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider, O., et al., "Synergistic Robotic Assistance to Cardiac Procedures," presented to Computer Assisted Radiology and Surgery on Jun. 23-26, 1999, 5 pages.
Sensable Technologies, Inc., "Freeform Feel the Difference", 2001, 4 pages.
Sensible Technologies, Inc., "FreeForm Modeling—Technical Features," 2003, 2 pages.
Tognetti, Lawrence Joseph, "Actuator Design for a Passive Haptic Display," Georgia Institute of Technology, Jun. 1999, 33 pages.
World Wide Web, http://haptics.me.jhu.edu/r.sub.—hapt.html, "Haptic Interfaces and Virtual Environments," printed on Jun. 12, 2003, 2 pages.
World Wide Web, http://haptics.me.jhu.edu/r.sub.—kine.html, "Robot Design and Kinematics," printed on Jun. 12, 2003, 2 pages.
World Wide Web, http://www.acrobot.co.uk/background.html, "The Acrobot Company Limited—Background," printed on Jul. 10, 2002, 1 page.
World Wide Web, http://www.acrobot.co.uk/home.html, "The Acrobot Company Limited—Precision Surgical Systems," printed on Jul. 10, 2002, 1 page.
World Wide Web, http://www.acrobot.co.uk/meetings.html, "The Acrobot Company Limited—Meetings and Publications," printed on Jul. 10, 2002, pp. 1-3.
World Wide Web, http://www.acrobot.co.uk/products.html, "The Acrobot Company Limited—Products," printed on Jul. 10, 2002, pp. 1-6.
World Wide Web, http://www.fcs-cs.com/robotics/content/assistance.htm, "Surgical Assistance," printed on Jun. 12, 2003, 1 page.
World Wide Web, http://www.fcs-cs.com/robotics/content/design.htm, "Virtual Design, Assembly & Maintenance," printed on Jun. 12, 2003, 1 page.
World Wide Web, http://www.fcs-cs.com/robotics/content/endeffectors.htm, "End effectors," printed on Jun. 12, 2003, 1 page.
World Wide Web, http://www.fcs-cs.com/robotics/content/hapticmaster.htm, "HapticMaster", printed on Jun. 12, 2003, 1 page.
World Wide Web, http://www.fcs-cs.com/robotics/content/reality.htm, "Virtual Reality," printed on Jun. 12, 2003, 1 page.
World Wide Web, http://www.fcs-cs.com/robotics/content/rehabilitation.htm, "Rehabilitation," printed on Jun. 12, 2003, 1 page.
World Wide Web, http://www.fcs-cs.com/robotics/content/research.htm, "Research," printed on Jun. 12, 2003, 1 page.
World Wide Web, http://www.fcs-cs.com/robotics/content/simulation.htm, "Simulation & Training," printed on Jun. 12, 2003, 1 page.
World Wide Web, http://www.fcs-cs.com/robotics/content/software.htm, "Software," printed on Jun. 12, 2003, 1 page.
World Wide Web, http://www.merl.com/projects/surgSim99/, "Knee Arthroscopy Simulation," printed on Jun. 12, 2003, 2 pages.
Written Opinion for PCT/US2006/049216, dated May 8, 2008.
Zilles, et al., "A Constraint-Based God-object Method for Haptic Display", IEEE Proceedings, pp. 146-151, 1995.
Germano et al., Clinical Use of the Optical Digitizer for Intracranial Neuronavigation, Neurosurgery, vol. 45(2), Aug. 1999, 15 pages.
Staecker et al., "Use of the LandmarX (tm) Surgical Navigation System in Lateral Skull Base and Temporal Bone Surgery", SkullBase, vol. 11, No. 4, 2001, pp. 245-255; Thieme Medical Publishers, Inc. 11 pages.
Decision to Refuse a European Patent Application for EP Application No. 07756266.8 dated Aug. 3, 2016, 32 pages.
Provision of the Minutes in Accordance with Rule 124(4) EPC for EP Application No. 07756266.8 dated Aug. 2, 2016, 5 pages.

\* cited by examiner

METHOD AND APPARATUS FOR CONTROLLING A HAPTIC DEVICE

CROSS REFERENCE TO RELATED APPLICATIONS

This application claims priority from U.S. Provisional Patent Application Ser. No. 60/801,378, filed May 19, 2006, the disclosure of which is hereby incorporated by reference herein in its entirety.

BACKGROUND OF THE INVENTION

1. Field of the Invention

The invention relates to a surgical system and, more particularly, to method and apparatus for controlling a haptic device.

2. Description of Related Art

Minimally invasive surgery (MIS) is the performance of surgery through incisions that are considerably smaller than incisions used in traditional surgical approaches. For example, in an orthopedic application such as total knee replacement surgery, an MIS incision length may be in a range of about 4 to 6 inches whereas an incision length in traditional total knee surgery is typically in a range of about 6 to 12 inches. As a result of the smaller incision length, MIS procedures are generally less invasive than traditional surgical approaches, which minimizes trauma to soft tissue, reduces post-operative pain, promotes earlier mobilization, shortens hospital stays, and speeds rehabilitation.

MIS presents several challenges for a surgeon. For example, in minimally invasive orthopedic joint replacement, the small incision size reduces the surgeon's ability to view and access the anatomy, which increases the complexity of sculpting bone and assessing proper implant position. As a result, accurate placement of implants may be difficult. Conventional techniques for counteracting these problems include, for example, surgical navigation, positioning the leg for optimal joint exposure, and employing specially designed, downsized instrumentation and complex surgical techniques. Such techniques, however, typically require a large amount of specialized instrumentation, a lengthy training process, and a high degree of skill. Moreover, operative results for a single surgeon and among various surgeons are not sufficiently predictable, repeatable, and/or accurate. As a result, implant performance and longevity varies among patients.

Conventional efforts to facilitate the performance and improve the outcome of minimally invasive and traditional orthopedic joint procedures may include the use of a robotic surgical system. For example, some conventional techniques include autonomous robotic systems, such as the ROBODOC system (formerly available from Integrated Surgical Systems, Inc., Sacramento, Calif.). Such systems, however, typically serve primarily to enhance bone machining by performing autonomous cutting with a high speed burr. Although such systems enable precise bone resections for improved implant fit and placement, they act autonomously (rather than cooperatively with the surgeon) and thus require the surgeon to cede a degree of control to the robot. Additional drawbacks of autonomous systems include the large size of the robot, poor ergonomics, increased incision length for adequate robot access, and limited acceptance by surgeons and regulatory agencies due to the autonomous nature of the system. Such systems also typically require rigid clamping of the bone during registration and cutting and thus lack real-time adaptability to the dynamic intraoperative scene.

Other conventional robotic systems include non-autonomous robots that cooperatively interact with the surgeon, such as the ACROBOT system (The Acrobot Company Limited, London, Great Britain). One drawback of conventional interactive robotic systems, however, is that such systems lack the ability to adapt surgical navigation in real-time to a dynamic intraoperative environment. For example, U.S. Pat. No. 7,035,716, which is hereby incorporated by reference herein in its entirety, discloses an interactive robotic system programmed with a three-dimensional virtual region of constraint that is registered to a patient. The robotic system includes a three degree of freedom (3 DOF) arm having a handle that incorporates force sensors. The surgeon utilizes the handle to manipulate the arm and move the cutting tool. Moving the arm via the handle is required so that the force sensors can measure the force being applied to the handle by the surgeon. The measured force is then used to control motors to assist or resist movement of the cutting tool. For example, during a knee replacement operation, the femur and tibia of the patient are fixed in position relative to the robotic system. As the surgeon applies force to the handle to move the cutting tool, the interactive robotic system applies an increasing degree of resistance to resist movement of the cutting tool as the tool approaches a boundary of the virtual region of constraint. In this manner, the robotic system guides the surgeon in preparing the bone by maintaining the tool within the virtual region of constraint. As with the above-described autonomous systems, however, the interactive robotic system functions primarily to enhance bone machining. Additionally, the 3 DOF configuration of the arm and the requirement that the surgeon manipulate the arm using the force handle results in limited flexibility and dexterity, making the robotic system unsuitable for certain MIS applications. The interactive robotic system also requires the anatomy to be rigidly restrained and the robotic system to be fixed in a gross position and thus lacks real-time adaptability to the intraoperative scene.

Although some interactive robotic systems may not require fixation of the anatomy, such as the VECTORBOT system (BrainLAB, Inc., Westchester, Ill.), such systems do not enable bone sculpting but instead merely function as intelligent tool guides. For example, such systems may control a robotic arm to constrain movement of a drill along a pre-planned drilling trajectory to enable a surgeon to drill a hole in a vertebra for placement of a pedicle screw. Similarly, other robotic systems, such as the BRIGIT system (Zimmer, Inc., Warsaw, Ind.), simply position a mechanical tool guide. For example, the robotic system disclosed in International Pub. No. WO 2005/0122916, and hereby incorporated by reference herein in its entirety, discloses a robotic arm that positions a mechanical tool guide. Using the robot-positioned tool guide, the surgeon manually manipulates a conventional surgical tool, such as a saw or drill, to make cuts to the patient's anatomy while the robot constrains movement of the tool guide. Although such systems may increase the accuracy and repeatability of the bone cuts, they are limited to performing the functions of a conventional tool guide and thus lack the ability to enable the surgeon to sculpt complex shapes in bone, as may be required for minimally invasive modular implant designs.

Some non-robotic conventional surgical tools useful for bone sculpting do not require fixation of the relevant anatomy, such as the Precision Freehand Sculptor (Blue Belt Technologies, Inc., Pittsburgh, Pa.). One drawback of such tools, however, is that they do not function in a manner that is transparent to the user. For example, U.S. Pat. No. 6,757,582, which is hereby incorporated by reference herein in its entirety, discloses a handheld surgical tool that can be used for sculpting a target shape into a bone. The handheld tool is a freehand cutting tool that is manipulated by the surgeon to grind away portions of the bone to form a desired target shape in the bone. The target shape is defined, for example, by a voxel-based model that is registered to the physical bone. During cutting, both the bone and the cutting tool are tracked to enable a controller to determine whether the cutting tool is impinging on the boundaries of the target shape and therefore cutting away bone that should be left intact. If so, the controller may shut off or retract the cutting tool to protect the bone. Although the bone is protected, the operation of the surgical tool is interrupted during the surgical procedure and the length of time to perform the procedure may increase. Further, interruption of cutting may also result in a rough surface cut. Additionally, such systems merely disable the cutting tool based on a position of the tool relative to the target shape but do not actually constrain the surgeon's manipulation of the cutting tool, for example, to prevent contact between the cutting tool and sensitive anatomy, or address other adverse situations, such as when rapid motion of the anatomy is detected. Thus, such systems may not include adequate safeguards to protect the patient. Moveover, a handheld tool that incorporates a shutoff mechanism may be bulky and heavier than a normal freehand tool or a gravity compensated interactive arm. Thus, it may be difficult for a surgeon to maneuver such a handheld tool to produce fine cutting motions, which makes such tools unsuited for applications that require complex shapes to be sculpted in bone, especially in a minimally invasive surgical environment such as when cutting in the gap between the femur and the tibia in a knee replacement operation without dislocating or distracting the joint.

In view of the foregoing, a need exists for a surgical system that is able to cooperatively interact with a surgeon to enable the surgeon to sculpt complex shapes in bone in a minimally invasive manner and that has the ability to dynamically compensate for motion of objects in the intraoperative environment in a manner that safeguards the patient and is substantially transparent to the surgeon.

SUMMARY OF THE INVENTION

According to an aspect of the present invention, a method for calibrating a surgical device includes acquiring first data including a position and/or an orientation of a first object disposed on the surgical device at a first location; acquiring second data including a position and/or an orientation of a second object disposed on the surgical device at a second location; determining third data including a position and/or an orientation of the first object relative to the second location; and determining a position and/or an orientation of the second object relative to the second location based at least in part on the first data, the second data, and the third data.

According to another aspect, a system for calibrating a surgical device includes a first object configured to be disposed on the surgical device, a second object configured to be disposed on the surgical device, and a computing system. The computing system is programmed to determine first data including a position and/or an orientation of the first object when the first object is disposed on the surgical device at a first location; determine second data including of a position and/or an orientation of the second object when the second object is disposed on the surgical device at a second location; determine third data including a position and/or an orientation of the first object relative to the second location; and determine a position and/or an orientation of the second object relative to the second location based at least in part on the first data, the second data, and the third data.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

Figure 1:
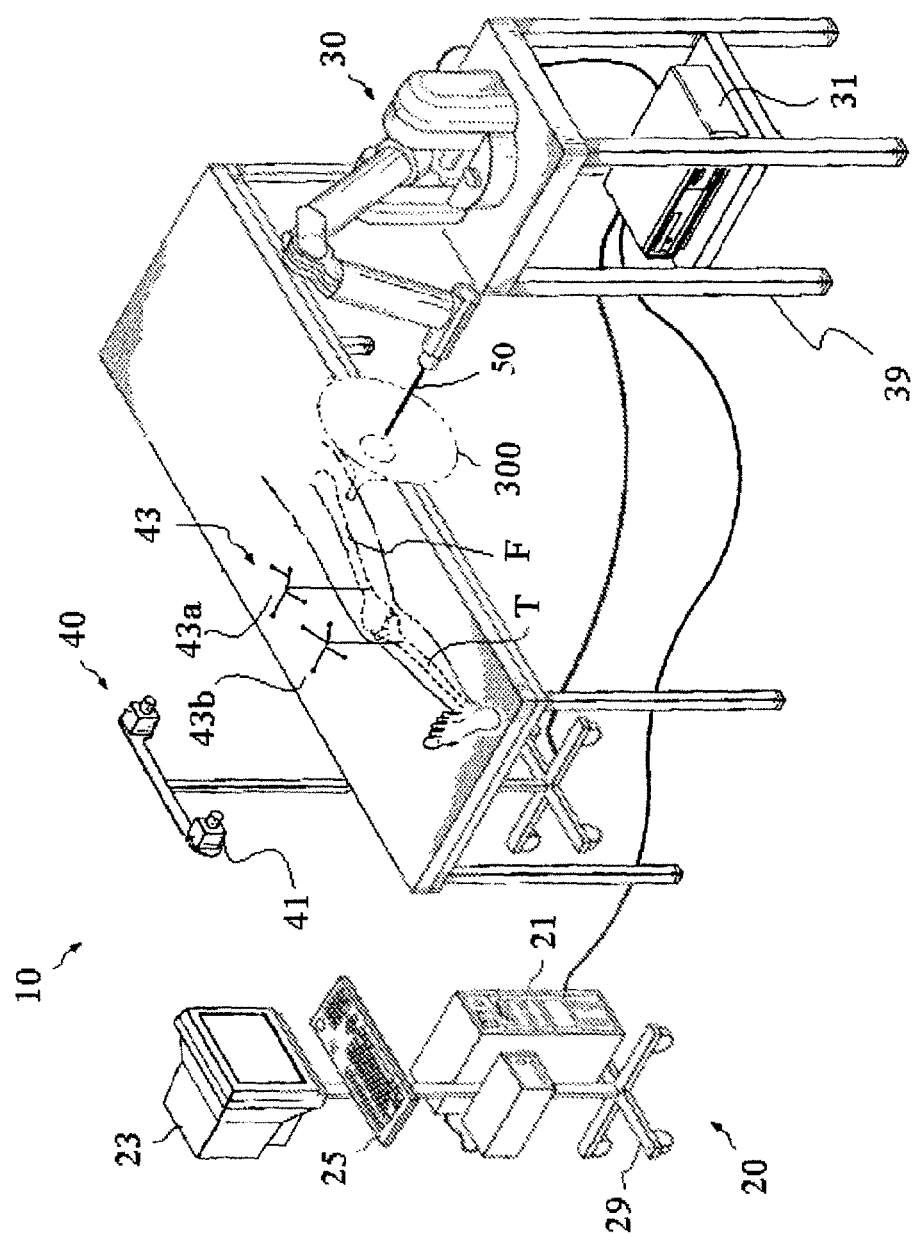
FIG. 1 is a perspective view of an embodiment of a surgical system according to the present invention.

Presently preferred embodiments of the invention are illustrated in the drawings. An effort has been made to use the same or like reference numbers to refer to the same or like parts.

FIG. 1 shows an embodiment of a surgical system 10. The surgical system 10 includes a computing system 20, a haptic device 30, and a tracking system 40. In one embodiment, the surgical system 10 is a robotic surgical system as disclosed in U.S. patent application Ser. No. 11/357,197, Pub. No. US 2006/0142657, filed Feb. 21, 2006, and incorporated by reference herein in its entirety. In a preferred embodiment, the surgical system 10 is the HAPTIC GUIDANCE SYSTEM™ available from MAKO SURGICAL CORP.® in Ft. Lauderdale, Fla.

The computing system 20 includes hardware and software for operation and control of the surgical system 10 and may comprise a computer 21, a computer 31, a display device 23, an input device 25, and a cart 29. The computing system 20 is adapted to enable the surgical system 10 to perform various functions related to surgical planning, navigation, image guidance, and/or haptic guidance. The computer 21 is preferably customized for surgical planning and navigation and includes algorithms, programming, and software utilities related to general operation, data storage and retrieval, computer aided surgery (CAS), and/or any other suitable functionality. In contrast, the computer 31 is preferably customized for controlling performance, stability, and/or safety of the haptic device 30 and includes haptic control utilities and programs that enable the haptic device 30 to utilize data from the tracking system 40.

The haptic device 30 is a surgical device configured to be manipulated by a user (such as a surgeon) to move a surgical tool 50 to perform a procedure on a patient, such as sculpting a surface of a bone to receive an implant. During the procedure, the haptic device 30 provides haptic guidance to the surgeon, for example, to maintain the tool 50 within a predefined virtual boundary. As disclosed in the above-referenced Pub. No. US 2006/0142657, the virtual boundary may be defined by a virtual haptic object that is generated by the computing system 20 and registered to (associated with) the anatomy of the patient. The haptic object establishes a desired relationship between the anatomy and the tool 50, such as a desired position, orientation, velocity, and/or acceleration of the tool 50 relative to the anatomy. In operation, when the surgeon moves the tool 50 in a manner that violates the desired relationship (such as when the tool 50 contacts a virtual boundary), the haptic device 30 provides haptic guidance in the form of tactile feedback (e.g., vibration) and/or force feedback (e.g., force and/or torque) to the surgeon. The haptic guidance may be experienced by the surgeon, for example, as resistance to further tool movement in the direction of the virtual boundary. As a result, the surgeon may feel as if the tool 50 has encountered a physical object, such as a wall. In this manner, the virtual boundary functions as a virtual cutting guide. Thus, the surgical system 10 limits the surgeon's ability to physically manipulate the haptic device 30 (e.g., by providing haptic guidance and/or a limit on user manipulation of the haptic device 30) by implementing control parameters based on a relationship between the anatomy and a position, an orientation, a velocity, and/or an acceleration of a portion of the haptic device 30, such as the tool 50. In addition to haptic objects, the relationship may be based on predefined parameters, such as a predefined depth that limits total travel of the tool 50.

Guidance from the haptic device 30 coupled with computer aided surgery (CAS) enables a surgeon to actively and accurately control surgical actions, such as bone cutting, and delivery of localized therapies (e.g., in the brain). In orthopedic applications, the haptic device 30 can be applied to the problems of inaccuracy, unpredictability, and non-repeatability in bone preparation by guiding the surgeon in proper sculpting of bone to thereby enable precise, repeatable bone resections while maintaining intimate involvement of the surgeon in the bone preparation process. Moreover, because the haptic device 30 guides the surgeon during cutting, the skill level of the surgeon is less critical. Thus, surgeons of varying skill degree and experience are able perform accurate, repeatable bone resections.

Figure 2A:
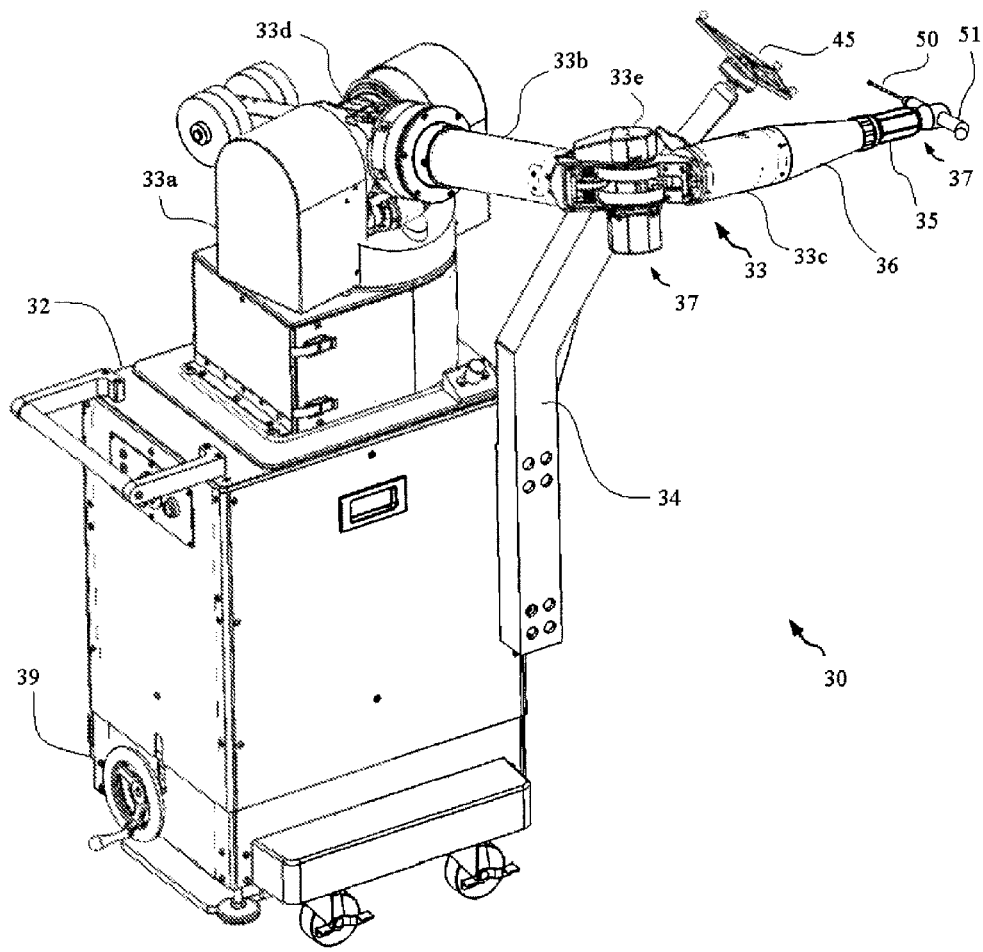
FIG. 2A is a perspective view of an embodiment of a haptic device according to the present invention.

The haptic device 30 may be robotic, non-robotic, or a combination of robotic and non-robotic systems. In one embodiment, the haptic device 30 is a robotic system as disclosed in the above-referenced Pub. No. US 2006/0142657. In a preferred embodiment, the haptic device is the HAPTIC GUIDANCE SYSTEM™ available from MAKO SURGICAL CORP.® in Ft. Lauderdale, Fla. As shown in FIG. 2A, the haptic device 30 includes a base 32, an arm 33, an end effector 35, a user interface 37, and a platform 39.

The base 32 provides a foundation for the haptic device 30. The base 32 supports the arm 33 and may also house other components, such as, for example, controllers, amplifiers, actuators, motors, transmission components, clutches, brakes, power supplies, sensors, computer hardware, and/or any other well-known robotic component.

Figure 2B:
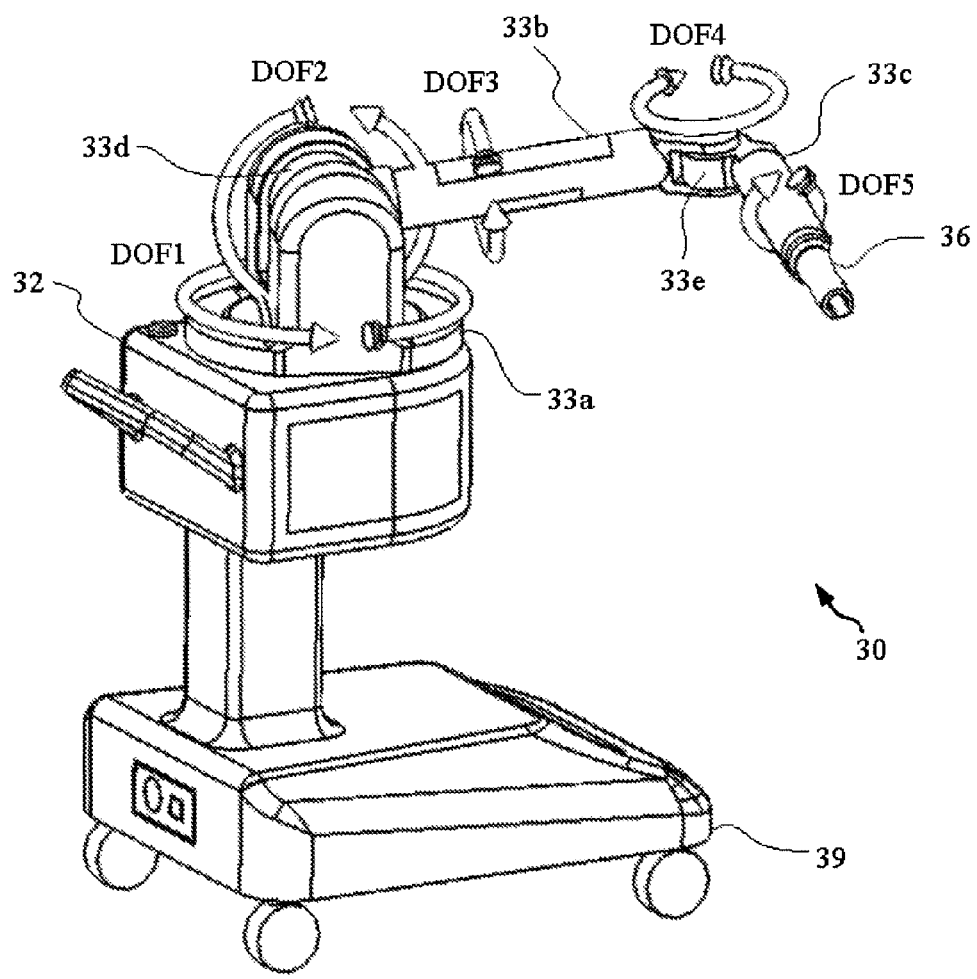
FIG. 2B is a perspective view of an embodiment of a haptic device according to the present invention.
Figure 2C:
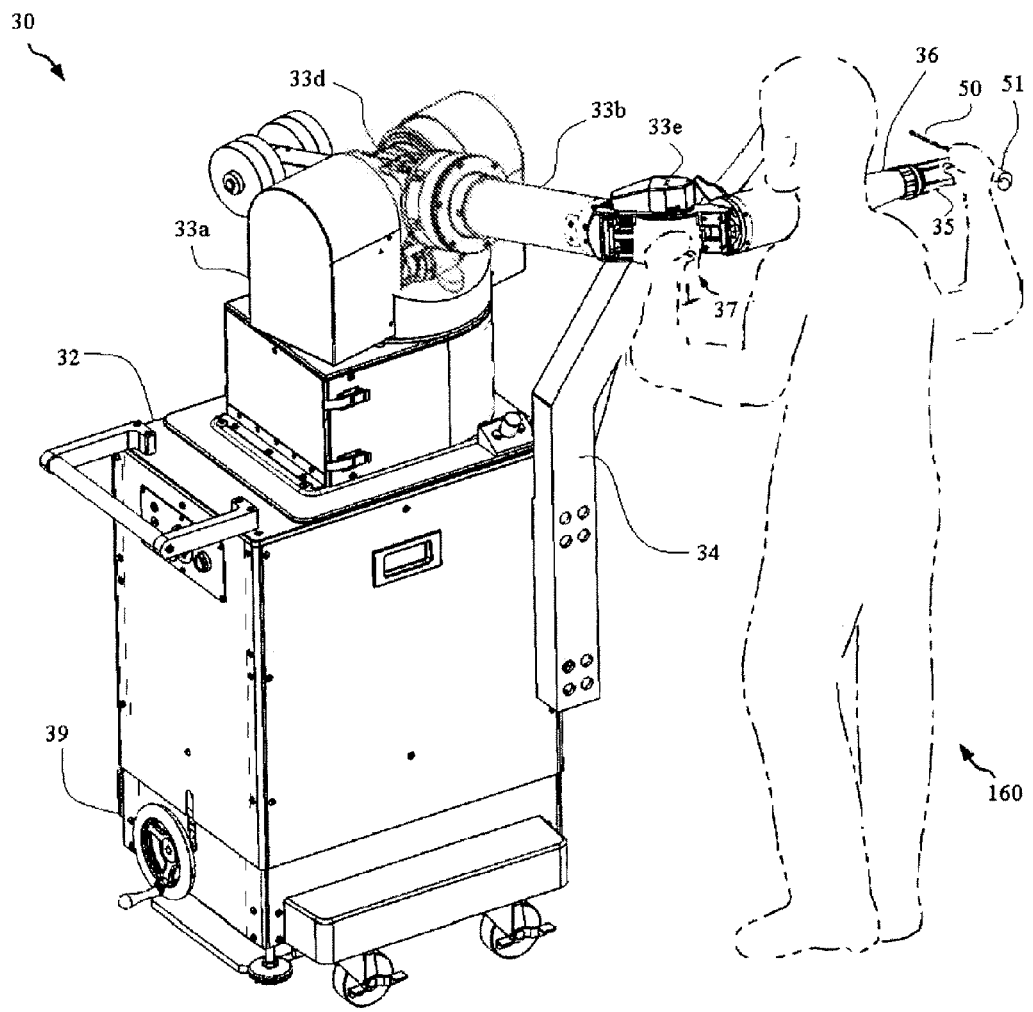
FIG. 2C is a perspective view of the haptic device of FIG. 2A showing a user operating the haptic device.

The arm 33 is disposed on the base 32 and is adapted to enable the haptic device 30 to be manipulated by the user. The arm 33 may be an articulated linkage such as serial device, a parallel device, or a hybrid device (i.e., a device having both serial and parallel elements). In a preferred embodiment, the arm 33 is a serial device having four or more degrees of freedom (axes of movement), such as, for example, a robotic arm known as the "Whole-Arm Manipulator" or WAM™ currently manufactured by Barrett Technology, Inc. The arm 33 includes a proximal end disposed on the base 32 and a distal end that includes the end effector 35 to which the surgical tool 50 is coupled. To manipulate the haptic device 30, a user 160 simply grasps and moves the arm 33 (as shown in FIG. 2C), which results in movement of the tool 50. In one embodiment, the arm 33 includes a first segment 33a, a second segment 33b, and a third segment 33c as shown in FIG. 2A. The first segment 33a and the second segment 33b are connected at a first joint 33d (e.g., a shoulder joint), and the second segment 33b and the third segment 33c are connected at a second joint 33e (e.g., an elbow joint). As shown in FIG. 2B, the arm 33 has a first degree of freedom $DOF_1$, a second degree of freedom $DOF_2$, a third degree of freedom $DOF_3$, and a fourth degree of freedom $DOF_4$. Dexterity of the arm 33 may be enhanced by adding additional degrees of freedom. For example, the arm 33 may include a wrist 36 disposed on the third segment 33c as shown in FIG. 2A. The wrist 36 includes one or more degrees of freedom, such as a degree of freedom $DOF_5$, to augment the degrees of freedom $DOF_1$, $DOF_2$, $DOF_3$, and $DOF_4$. The wrist 36 may be, for example, a one or three degree of freedom WAM™ wrist manufactured by Barrett Technology, Inc. or a one degree of freedom direct drive wrist.

To enable the haptic device 30 to provide haptic guidance to the user, the arm 33 incorporates a drive system, such as the drive system disclosed in the above-referenced Pub. No. US 2006/0142657. The drive system includes actuators (e.g., motors) and a mechanical transmission. In an exemplary embodiment, the drive system includes a high-speed cable transmission and zero backlash, low friction, cabled differentials. The cable transmission may be, for example, a cable transmission used in the WAM™ robotic arm currently manufactured by Barrett Technology, Inc. and/or a cable transmission as described in U.S. Pat. No. 4,903,536, which is hereby incorporated by reference herein in its entirety.

The arm 33 also includes position sensors (not shown) for determining a position and an orientation (i.e., pose) of the arm 33, such as encoders and/or resolvers mounted on the joints 33d and 33e and/or encoders and/or resolvers mounted on a shaft of each motor.

The end effector 35 comprises a working end of the haptic device 30. As shown in FIG. 2A, the end effector 35 includes a proximal portion connected to the arm 33 and a distal portion that includes the tool 50 and a tool holder 51. The tool 50 may be, for example, a surgical tool (such as a burr, drill, probe, saw, etc.). In one embodiment, the tool 50 and the tool holder 51 comprise an electric, air cooled surgical tool currently manufactured by ANSPACH® and having product numbers EMAX2 (motor), L-2SB (2 mm fluted ball), L-4B (4 mm fluted ball), L-6B (6 mm fluted ball), and L-1R (12) (1.2 mm×12.8 mm fluted router). The surgical tool may also include additional components such as a user input device (e.g., a foot pedal such as ANSPACH® product number EMAX2-FP), a control console (e.g., ANSPACH® product number SC2000), and the like. Further, the tool 50 may be integrated into the surgical system 10 such that cutting information (e.g., velocity, torque, temperature, etc.) is available to the surgical system 10 and/or such that the surgical system 10 can control operation of the tool 50.

Figure 3A:
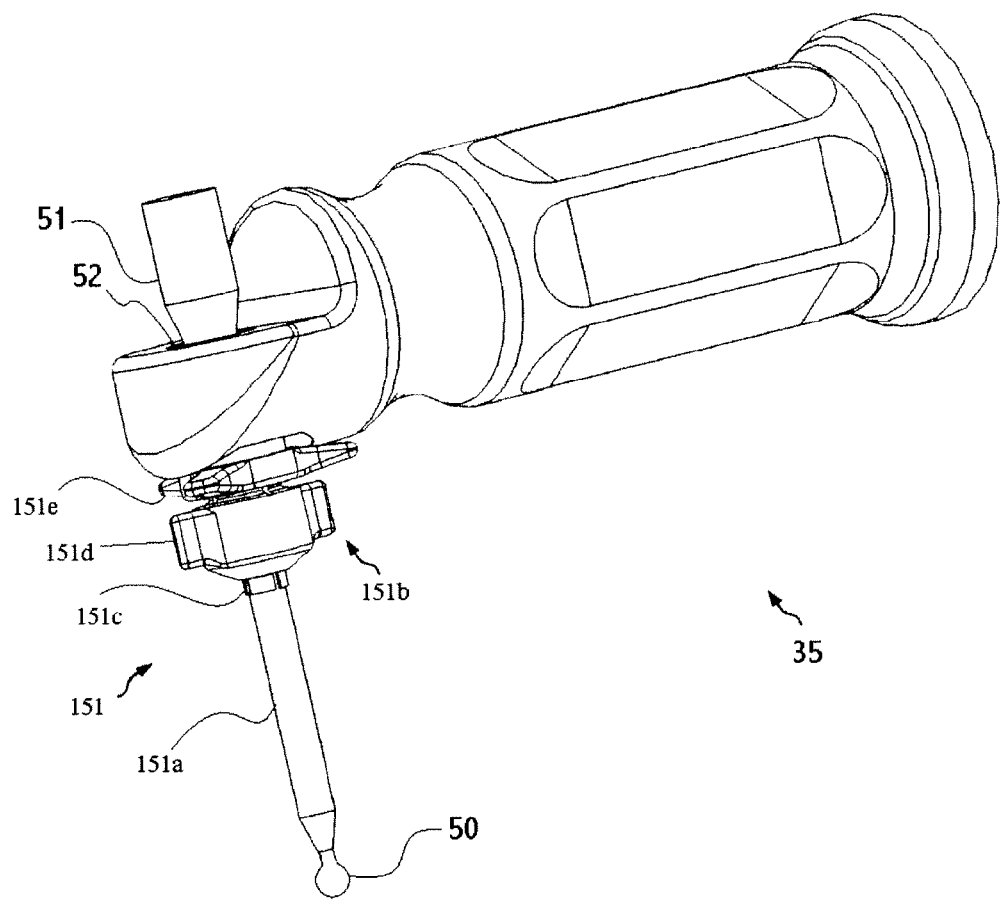
FIG. 3A is a perspective view of an embodiment of an end effector according to the present invention.
Figure 3B:
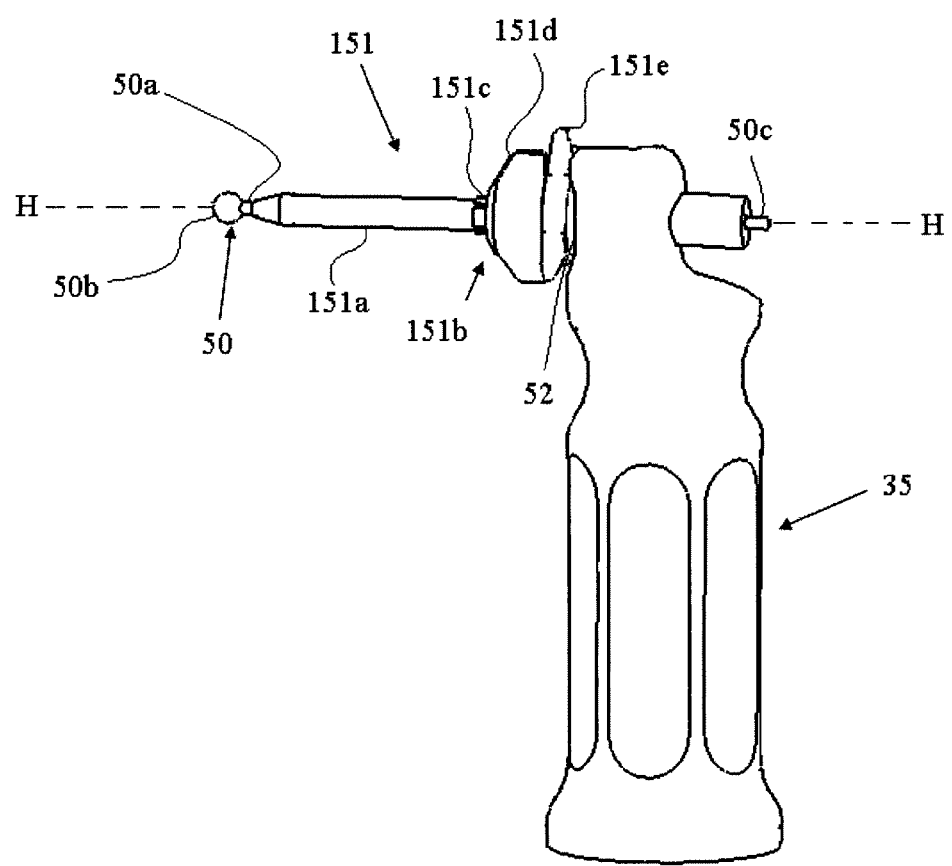
FIG. 3B is a side perspective view of the end effector of FIG. 3A.

In one embodiment, the tool holder 51 includes a holding device 151 configured to couple the surgical tool 50 to the haptic device 30. As shown in FIG. 3B, the holding device 151 comprises a first member 151a and a second member 151b. The first member 151a is configured to receive at least a portion of the tool 50 (e.g., a shaft 50a of the tool 50) and to engage the second member 151b. The second member 151b is configured to couple the first member 151a and the surgical tool 50 to the end effector 35 of the haptic device 30, to maintain the tool 50 in a desired position when the tool 50 is coupled to the end effector 35, and to substantially prevent movement of the tool 50 relative to the end effector 35. As shown in FIGS. 3A and 3B, the first member 151a of the holding device 151 may be a sleeve or sheath sized to receive a shaft 50a of the tool 50 and to be inserted into the second member 151b. For example, in one embodiment, the first member 151a has a diameter in a range of about 5.9 mm to about 6.1 mm at a first end (i.e., an end into which the shaft 50a is inserted) and a diameter of about 11.38 mm to about 11.48 mm at a second end (i.e., an end that is inserted into the second member 151b). The second member 151b of the holding device 151 may be any connector suitable for coupling a first object (e.g., a tool or work piece) to a second object (e.g., a machine or robot) in a manner that is secure, stable, and enables repeatable positioning of the first object relative to the second object. In one embodiment, the second member 151b includes a collet. In other embodiments, the second member 151b may include threads, clamping devices, set screws, and the like.

In one embodiment, the holding device 151 is configured so that an axis of the holding device 151 corresponds to a desired axis of the tool 50 when the holding device 151 is disposed on the haptic device 30. For example, in one embodiment (shown in FIGS. 3A and 3B), the second member 151b of the holding device 151 includes a connector comprising a collet 151c, a collet knob 151d, and a collar nut 151e. In this embodiment, the collet 151c includes a male morse taper feature, and the aperture 52 of the end effector 35 includes a corresponding female morse taper feature. The collet 151c is mated to the aperture 52 and tightened onto the end effector 35 with the collar nut 151e. This taper connection establishes an axis H-H that corresponds to the desired axis of the surgical tool 50. As shown in FIG. 3B, when the tool 50 is coupled to the end effector 35 via the holding device 151, an axis of the tool 50 aligns with the axis H-H. In this manner, the holding device 151 aligns the tool 50 in a desired configuration relative to the end effector 35. After the collet 151c is mated with the end effector 35, the first member 151a is inserted into the collet 151c. The shaft 50a of the tool 50 is inserted into the first member 151a until a tip 50b of the tool 50 is in a desired position. Once the tip 50b is properly positioned, the collet knob 151d is tightened down onto the fingers or tangs of the collet 151a. The clamping force exerted on the first member 151a and the tool 50 by the collet fingers secures the first member 151a and the tool 50 in place. In this manner, the holding device 151 substantially prevents movement of the first member 151a and the tool 50 relative to the end effector 35. Once installed on the end effector 35, a portion 50c (shown in FIG. 3B) of the tool 50 projects from the end effector 35 and can be attached to a motor for driving the tool 50. Additionally, because the holding device 151 and the tool 50 can be decoupled from the end effector 35, the components can be removed as necessary for replacement, sterilization, and the like.

The user interface 37 enables physical interaction between the user and the haptic device 30. The interface 37 is configured so that the user can grasp the interface 37 and manipulate the tool 50 while simultaneously receiving haptic guidance from the haptic device 30. The interface 37 may be a separate component affixed to the haptic device 30 (such as a handle or hand grip) or may simply be part of the existing structure of the haptic device 30 (such as the arm 33). Because the interface 37 is affixed to or is an integral part of the haptic device 30, any haptic feedback output by the haptic device 30 is transmitted directly to the user when the user is in contact with the interface 37. Thus, the interface 37 advantageously enables the haptic device 30 to hold the tool 50 cooperatively with the surgeon (as shown in FIG. 2C) and to simultaneously provide haptic guidance.

The tracking system 40 of the surgical system 10 is configured to track one or more objects during a surgical procedure to detect movement of the objects. As described in the above-referenced Pub. No. US 2006/0142657. The tracking system 40 includes a detection device that obtains a pose (i.e., position and orientation) of an object with respect to a coordinate frame of reference of the detection device 41. As the object moves in the coordinate frame of reference, the detection device tracks the object. A change in the pose of the object indicates that the object has moved. In response, the computing system 20 can make appropriate adjustments to the control parameters for the haptic device 30. For example, when the anatomy moves, the computing system 20 can make a corresponding adjustment to a virtual haptic object (e.g., a virtual cutting boundary) that is registered to the anatomy. Thus, the virtual cutting boundary moves along with the anatomy.

Figure 9:
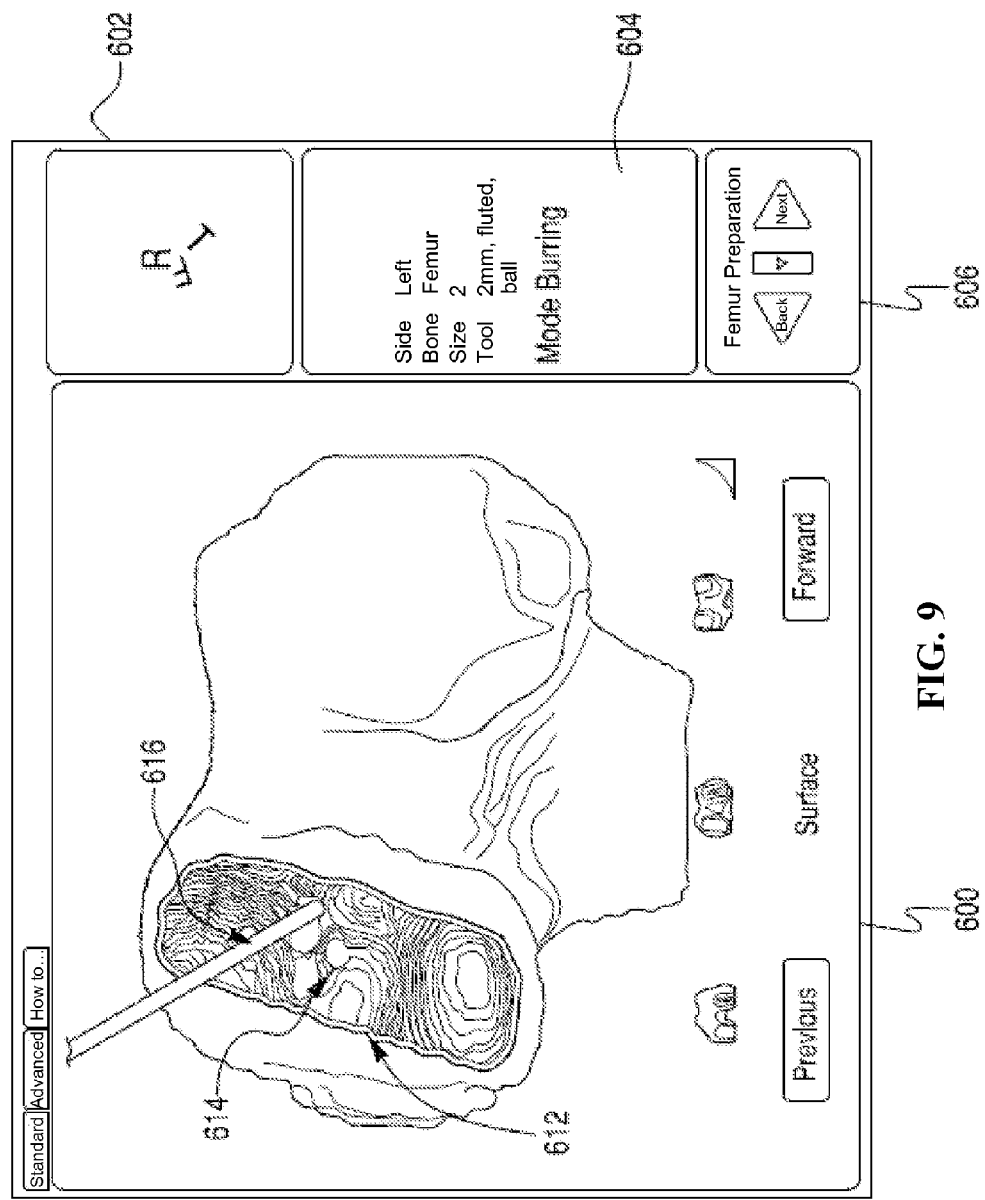
FIG. 9 shows an embodiment of a display of a CAS system according to the present invention.

Pose data from the tracking system 40 is also used to register (i.e., map or associate) coordinates in one space to those in another space to achieve spatial alignment, for example, using a coordinate transformation process. Registration may include any known registration technique, such as, for example, image-to-image registration; image-to-physical space registration; and/or combined image-to-image and image-to-physical-space registration. In one embodiment, the anatomy and the tool 50 (in physical space) are registered to a representation of the anatomy (such as an image 614 in image space) as disclosed in the above-referenced Pub. No. US 2006/0142657 and shown in FIG. 9. Based on registration and tracking data, the surgical system 10 can determine (a) a spatial relationship between the anatomy and the image 614 and (b) a spatial relationship between the anatomy and the tool 50 so that the computing system 20 can superimpose, and continually update, a virtual representation 616 of the tool 50 on the image 614. The relationship between the virtual representation 616 and the image 614 is substantially identical to the relationship between the tool 50 and the actual anatomy.

The tracking system 40 may be any tracking system that enables the surgical system 10 to continually determine (or track) a pose of the relevant anatomy of the patient and a pose of the tool 50 (and/or the haptic device 30). For example, the tracking system 40 may comprise a non-mechanical tracking system, a mechanical tracking system, or any combination of non-mechanical and mechanical tracking systems suitable for use in a surgical environment.

In one embodiment, the tracking system 40 includes a non-mechanical tracking system as shown in FIG. 1. The non-mechanical tracking system is an optical tracking system that comprises a detection device 41 and a trackable element (or tracker) that is configured to be disposed on a tracked object and is detectable by the detection device 41. In one embodiment, the detection device 41 includes a visible light-based detector, such as a micron tracker, that detects a pattern (e.g., a checkerboard pattern) on a tracking element. In another embodiment, the detection device 41 includes a stereo camera pair sensitive to infrared radiation and positionable in an operating room where the surgical procedure will be performed. The tracker is configured to be affixed to the tracked object in a secure and stable manner and includes an array of markers (e.g., an array S1 in FIG. 4) having a known geometric relationship to the tracked object. As is well known, the markers may be active (e.g., light emitting diodes or LEDs) or passive (e.g., reflective spheres, a checkerboard pattern, etc.) and have a unique geometry (e.g., a unique geometric arrangement of the markers) or, in the case of active, wired markers, a unique firing pattern. In operation, the detection device 41 detects positions of the markers, and the surgical system 10 (e.g., the detection device 41 using embedded electronics) calculates a pose of the tracked object based on the markers' positions, unique geometry, and known geometric relationship to the tracked object. The tracking system 40 includes a tracker for each object the user desires to track, such as an anatomy tracker 43 (to track patient anatomy), a haptic device tracker 45 (to track a global or gross position of the haptic device 30), an end effector tracker 47 (to track a distal end of the haptic device 30), and an instrument tracker 49 (to track an instrument held manually by the user).

Figure 4:
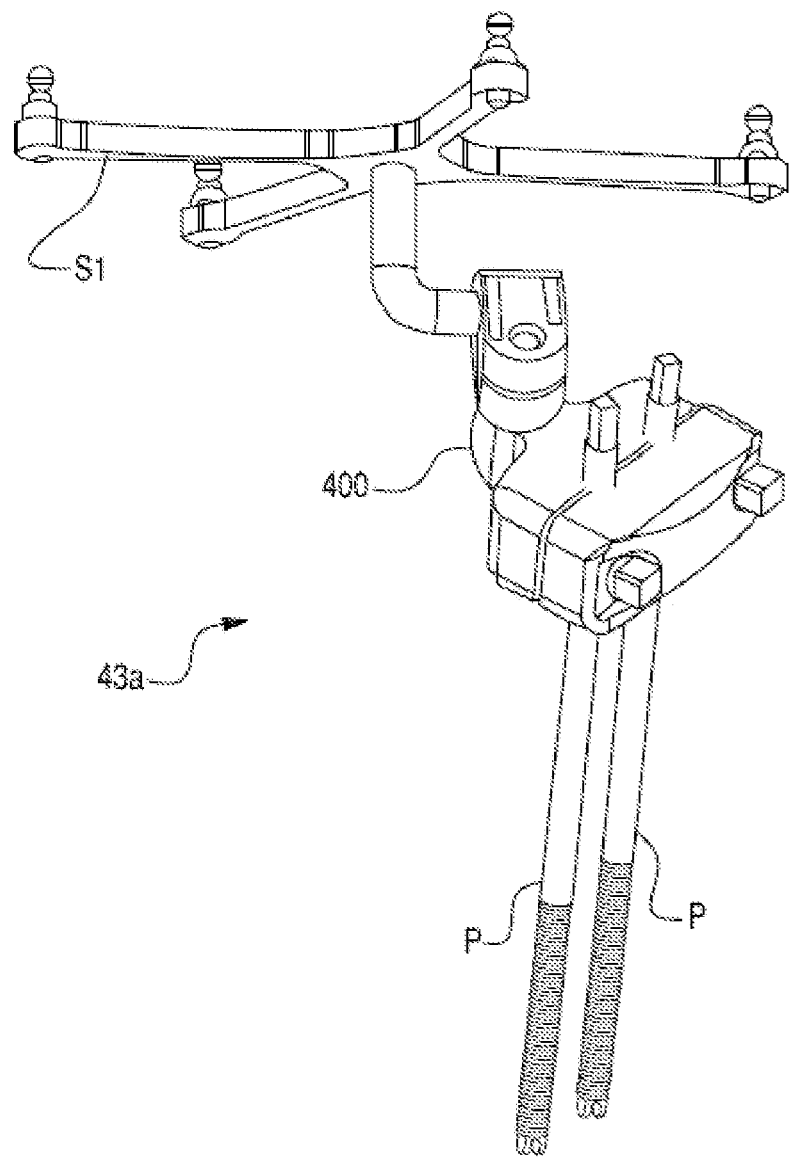
FIG. 4 is a perspective view of an embodiment of an anatomy tracker according to the present invention.

The anatomy tracker 43 is disposed on the patient's anatomy and enables the anatomy to be tracked by the detection device 41. The anatomy tracker 43 includes a fixation device for attachment to the anatomy, such as a bone pin, surgical staple, screw, clamp, intramedullary rod, or the like. In one embodiment, the anatomy tracker 43 is configured for use during knee replacement surgery to track a femur F and a tibia T of a patient. In this embodiment, as shown in FIG. 1, the anatomy tracker 43 includes a first tracker 43a adapted to be disposed on the femur F and a second tracker 43b adapted to be disposed on the tibia T. As shown in FIG. 4, the first tracker 43a includes a fixation device comprising bone pins P, a clamp 400, and a unique array S1 of markers (e.g., reflective spheres). The second tracker 43b is identical to the first tracker 43a except the second tracker 43b is installed on the tibia T and has its own unique array of markers. When installed on the patient, the first and second trackers 43a and 43b enable the detection device 41 to track a position of the femur F and the tibia T.

The haptic device tracker 45 is disposed on the haptic device 30 and enables the surgical system 10 to monitor a global or gross position of the haptic device 30 in physical space so that the surgical system 10 can determine whether the haptic device 30 has moved relative to other objects in the surgical environment, such as the patient, or whether the detection device 41 has moved relative to the haptic device 30. Such information is important because the tool 50 is attached to the haptic device 30. For example, if the user repositions or inadvertently bumps the haptic device 30 while cutting the femur F with the tool 50, the tracking system 40 will detect movement of the haptic device tracker 45. In response, the surgical system 10 can make appropriate adjustments to programs running on the computing system 20 to compensate for movement of the haptic device 30 (and the attached tool 50) relative to the femur F. As a result, integrity of the bone preparation process is maintained.

Figure 5:
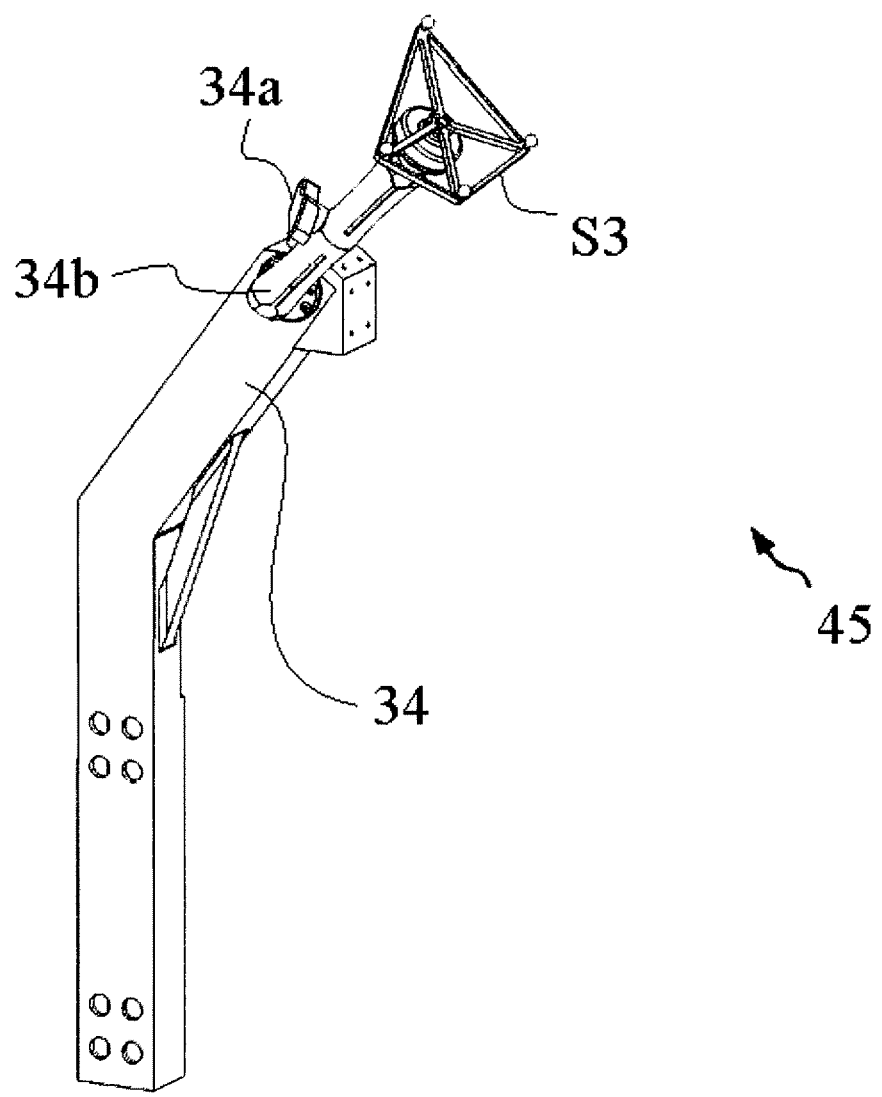
FIG. 5 is a perspective view of an embodiment of a haptic device tracker according to the present invention.

The haptic device tracker 45 includes a unique array S3 of markers (e.g., reflective spheres) and is adapted to be mounted on the base 32 of the haptic device 30 in a manner that enables the tracker 45 to be secured in a fixed position relative to the base 32. The fixed position is calibrated to the haptic device 30 during a haptic device registration calibration (discussed below) so that the surgical system 10 knows where the tracker 45 is located relative to the base 32. Once calibrated, the fixed position is maintained during the surgical procedure. In one embodiment, as shown in FIGS. 2A and 5, the tracker 45 is mounted on an arm 34 having a proximal end connected to the base 32 (e.g., via screws, rivets, welding, clamps, magnets, etc.) and a distal end that carries the array S3 of markers. The arm 34 may include one or more support members (e.g., brackets, struts, links, etc.) having a rigid structure so that the haptic device tracker 45 is fixed in a permanent position with respect to the haptic device 30. Preferably, however, the arm 34 is adapted for adjustability so that the array S3 is moveable relative to the haptic device 30. Thus, the array S3 can be positioned independently of the base 32 before being secured in a fixed position. As a result, a position of the array S3 can be customized for each surgical case (e.g., based on patient size, operating table height, etc.) and set so as not to impede the surgeon during a surgical procedure.

Adjustability may be imparted to the arm 34 in any known manner (e.g., an articulating linkage, a flexible neck, etc.). For example, in the embodiment of FIG. 5, the arm 34 includes a ball joint 34b on which the haptic device tracker 45 is disposed. The ball joint 34b includes a locking mechanism actuated by a handle 34a. In operation, the user may unscrew the handle 34a to release the ball joint 34b, manipulate the ball joint 34b until the tracker 45 is in a desired position, and tighten the handle 34a until the ball joint 34b is fixedly secured. In this manner, the tracker 45 may be fixed in the desired position. As an alternative to securing the tracker 45 in a fixed position and calibrating the fixed position to the haptic device 30, the arm 34 may include position sensors (e.g., encoders) similar to the position sensors of the arm 33 to provide measurements of a pose of the arm 34 relative to the base 32. When position sensors are incorporated into the arm 34, the haptic device registration calibration (discussed below) may be eliminated because the surgical system 10 can determine the location of the tracker 45 with respect to the base 32 based on the pose of the arm 34 provided by the position sensors.

The end effector tracker 47 enables the surgical system 10 to determine a pose of a distal end of the haptic device 30.

Figure 6A:
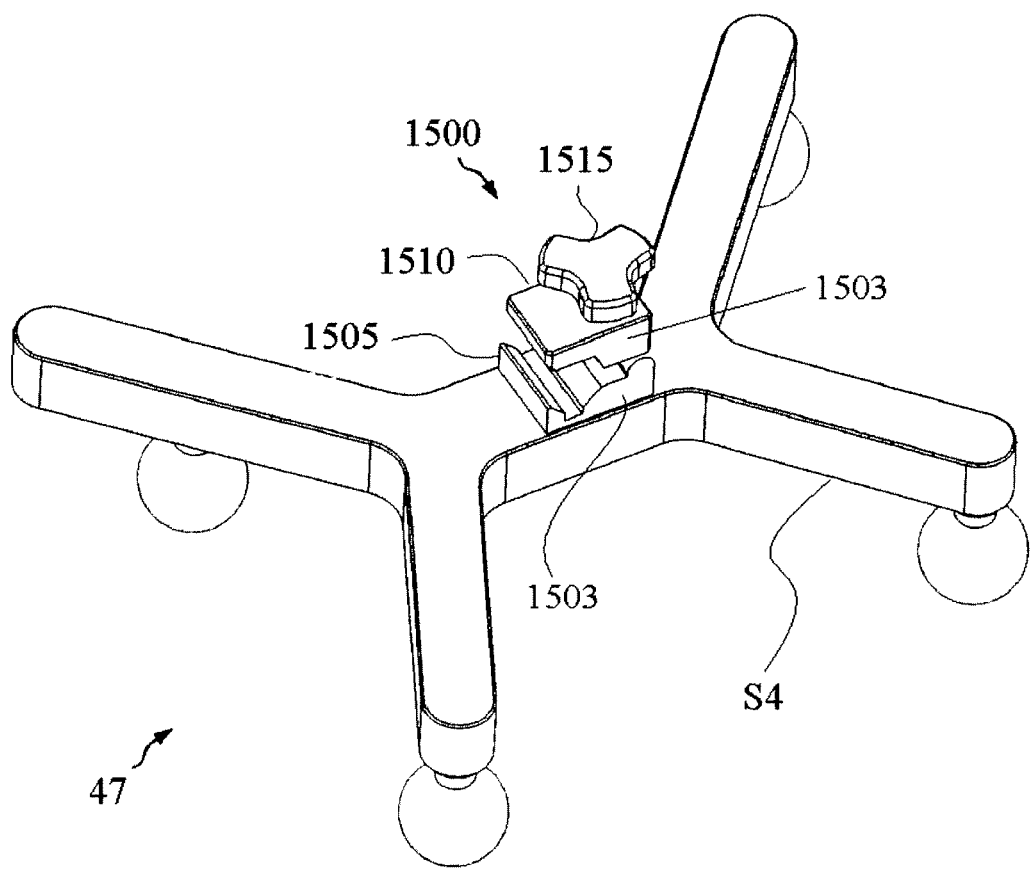
FIG. 6A is a perspective view of an embodiment of an end effector tracker according to the present invention.

The tracker 47 is preferably configured to be disposed on the haptic device 30 at a distal end of the arm 33 (e.g., on the segment 33c, the end effector 35, the tool 50, and/or the tool holder 51). In one embodiment (shown in FIG. 6B), the tracker 47 is disposed on the tool holder 51. As shown in FIG. 6A, the tracker 47 may include a unique array S4 of markers (e.g., reflective spheres) and may be adapted to be affixed to the haptic device 30 in any known manner, such as, for example, with a clamping device, threaded connection, magnet, or the like. In the embodiment of FIG. 6A, the tracker 47 is affixed to the haptic device 30 with a clamp 1500. The clamp 1500 may be formed integrally with the array S4 or affixed to the array S4 in any conventional manner, such as with mechanical hardware, adhesive, welding, and the like. The clamp 1500 includes a first portion 1505, a second portion 1510, and a thumbscrew 1515. The first and second portions 1505 and 1510 are shaped to receive a portion of the haptic device 30, such as a cylindrical portion of the tool 50 and/or the tool holder 51. In one embodiment, the cylindrical portion is the first member 151a of the holding device 151 of the tool holder 51 (shown in FIGS. 3A and 3B). To enable the clamp 1500 to grasp the cylindrical portion, the first portion 1505 may have a V-shaped groove (shown in FIG. 6A) and the second portion 1510 may have a planar surface so that the first and second portions 1505 and 1510 can securely receive the cylindrical portion when tightened together. In one embodiment, the clamp 1500 is configured so that the surgical system 10 can determine a point and/or an axis of the haptic device 30 at a location where the tracker 47 is disposed on the haptic device 30. For example, when the tracker 47 is secured to the cylindrical portion with the clamp 1500, the surgical system 10 is able to determine a point and/or an axis of the cylindrical portion (e.g., an axis H-H shown in FIG. 3B) based on the geometry of the tracker 47, specifically, the geometric relationship between the reflective spheres on the array S4 and the V-shaped groove on the first portion 1505 of the clamp 1500.

Figure 6B:
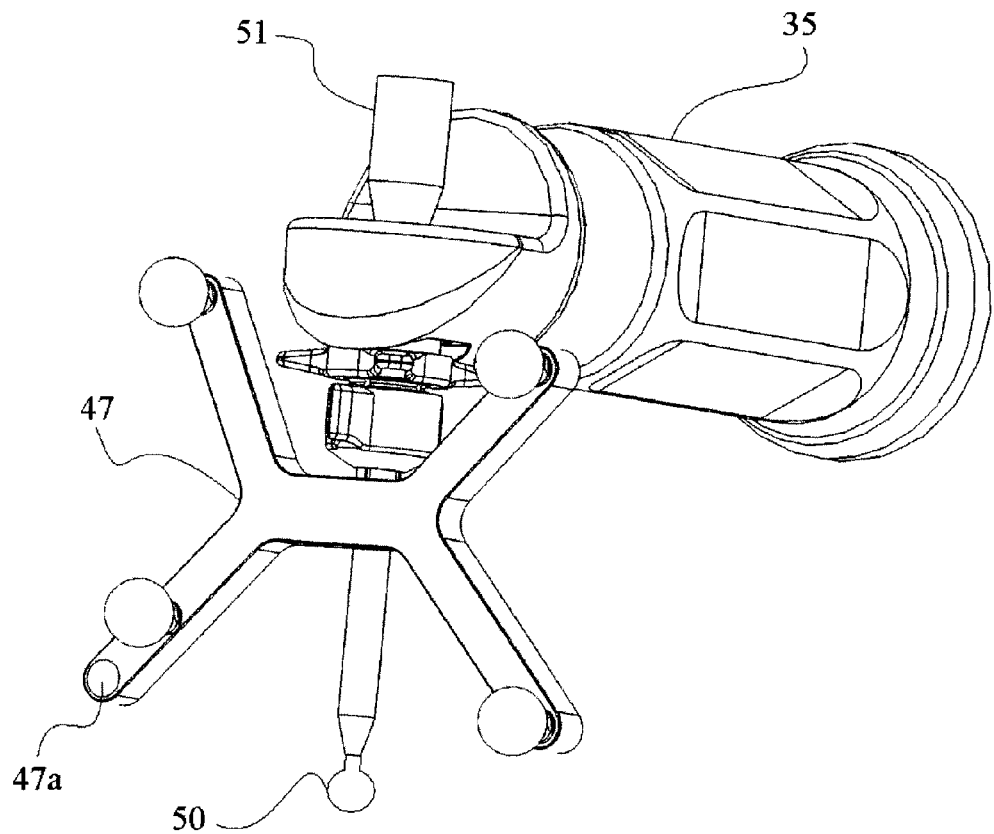
FIG. 6B is a perspective view of the end effector tracker of FIG. 6A attached to the end effector of FIG. 3A.

To install the end effector tracker 47 on the haptic device 30, the first and second portions 1505 and 1510 of the clamp 1500 are disposed around a cylindrical portion of the tool 50 or the tool holder 51 and tightened together using the thumbscrew 1515. The effector 47 may include a feature configured to aid in positioning the tracker 47 relative to the end effector 35. For example, the tracker 47 may include one or more surfaces 1503 (shown in FIG. 6B) that are adapted to abut corresponding surfaces on the haptic device 30. In one embodiment, the surfaces 1503 are configured to abut a portion of the tool holder 51, such as fingers or tangs of the collet 151c as shown in FIG. 6B. In operation, the user slides the clamp 1500 along the cylindrical portion of the tool holder 51 until the surfaces 1503 abut the fingers or tangs of the collet 151c and then tightens the thumb screw 1515. The tracker 47 may be removed by loosening the thumbscrew 1515 and sliding the tracker 47 off the cylindrical portion. In this manner, the tracker 47 may be removably and repeatably secured in a known position relative to the end effector 35. The tracker 47 may also include a feature, such as a divot 47a shown in FIG. 6B, to facilitate orientation of the tracker 47 relative to the end effector 35, for example, to avoid installing the tracker 47 upside down. After installation of the tracker 47, the user may reorient the tracker 47 (if desired) by loosening the clamp 1500 and swiveling the tracker 47 around the cylindrical portion. Thus, the clamp 1500 enables adjustability of the tracker 47 relative to the end effector 35. Adjustability is particularly useful during the haptic device registration calibration (described below) to orient the tracker 47 to face the detection device 41 to thereby improve tracking accuracy and visibility.

Alternatively, instead of a separate end effector tracker 47, the haptic device 30 may incorporate fiducials on the end effector 35. The fiducials may be similar to the unique array S4 of markers and may include, for example, reflective spheres. In contrast to the end effector tracker 47, the fiducials are not removed from the end effector 35 prior to surgery. One disadvantage of not removing the fiducials is that blood and debris may contaminate the fiducials during surgery, which occludes the fiducials and degrades their ability to reflect light to the detection device 41. Thus, the fiducials preferably include a smooth plastic coating so that any surface contamination can be easily removed. The fiducials should be mounted in a location on the end effector 35 that is visible to the detection device 41 during the haptic device registration calibration (described below) but that will not impede the surgeon during the surgical procedure. For example, the fiducials may be mounted on an underside of the end effector 35. Alternatively, the fiducials may be mounted on an adjustable linkage that can be positioned in a registration calibration position where there is a clear line of site between the fiducials and the detection device 41 and a stowed position where the fiducials will not hamper the surgeon during the surgical procedure.

In one embodiment, the end effector tracker 47 is used only during the haptic device registration calibration (discussed below) and is removed prior to performance of the surgical procedure. In this embodiment, the end effector tracker 47 is disposed on the end effector 35 and the haptic device tracker 45 is mounted to the base 32 (e.g., via the adjustable arm 34) so that a position of the haptic device tracker 45 with respect to the haptic device 30 is adjustable. Because the position of the haptic device tracker 45 is adjustable, the surgical system 10 does not know the location of the haptic device tracker 45 relative to the haptic device 30. To determine the geometric relationship between the haptic device 30 and the haptic device tracker 45, the registration calibration process utilizes the end effector tracker 47 (as described below). Although the end effector tracker 47 may remain on the haptic device 30 for the surgical procedure and can be continuously monitored, it is advantageous to remove the end effector tracker 47 when the registration calibration is complete to prevent the tracker 47 from impeding the surgeon during the surgical procedure. Another advantage of removing the tracker 47 is that movement of the tracker 47 during the surgical procedure may result in degraded performance of the surgical system 10 due to delays or limited bandwidth as the tracking system 40 detects and processes movement of the tracker 47.

In an alternative embodiment, the end effector tracker 47 may be eliminated. In this embodiment, the haptic device tracker 45 is fixed in a permanent position on the haptic device 30. Because the haptic device tracker 45 is permanently fixed on the haptic device 30, the relationship between the haptic device tracker 45 and the coordinate frame of the haptic device 30 is known. Accordingly, the surgical system 10 does not need the end effector tracker 47 for the registration calibration to establish a relationship between the haptic device tracker 45 and the coordinate frame of the haptic device 30. In this embodiment, the haptic device tracker 45 may be rigidly mounted on the haptic device 30 in any position that permits the tracking system 40 to see the array S3 of the haptic device tracker 45, that is close enough to the surgical site so as not to degrade accuracy, and that will not hinder the user or interfere with other personnel or objects in the surgical environment.

In another alternative embodiment, the haptic device 30 is firmly locked in position. For example, the haptic device 30 may be bolted to a floor of the operating room or otherwise fixed in place. As a result, the global or gross position of the haptic device 30 does not change substantially so the surgical system 10 does not need to track the global or gross position of the haptic device 30. Thus, the haptic device tracker 45 may be eliminated. In this embodiment, the end effector tracker 47 may be used to determine an initial position of the haptic device 30 after the haptic device 30 is locked in place. One advantage of eliminating the haptic device tracker 45 is that the surgical system 10 does not need to include monitoring data for the haptic device tracker 45 in the control loop. As a result, noise and errors in the control loop are reduced. Alternatively, the haptic device tracker 45 may be retained but is monitored only for detecting excessive motion of the base 32 or the tracking system 40 rather than being included in the control loop.

In another alternative embodiment, the tracking system 40 is attached to the haptic device 30 in a permanently fixed position. For example, the tracking system 40 (including the detection device 41) may be mounted directly on the haptic device 30 or connected to the haptic device 30 via a rigid mounting arm or bracket so that the tracking system 40 is fixed in position with respect to the haptic device 30. In this embodiment, the haptic device tracker 45 and the end effector tracker 47 may be eliminated because a position of the tracking system 40 relative to the haptic device 30 is fixed and can be established during a calibration procedure performed, for example, during manufacture or set up of the haptic device 30.

In another alternative embodiment, the tracking system 40 is attached to the haptic device 30 in an adjustable manner. For example, the tracking system 40 (including the detection device 41) may be connected to the haptic device 30 with an arm, such as the adjustable arm 34 (described above in connection with the haptic device tracker 45) so that the tracking system 40 is moveable from a first position to a second position relative to the haptic device 30. After the arm and the tracking system 40 are locked in place, a calibration can be performed to determine a position of the tracking system 40 relative to the haptic device 30. A calibration to determine the position of the tracking system 40 relative to the haptic device 30 may be performed, for example, by viewing the end effector tracker 47 with the tracking system 40.

Figure 7:
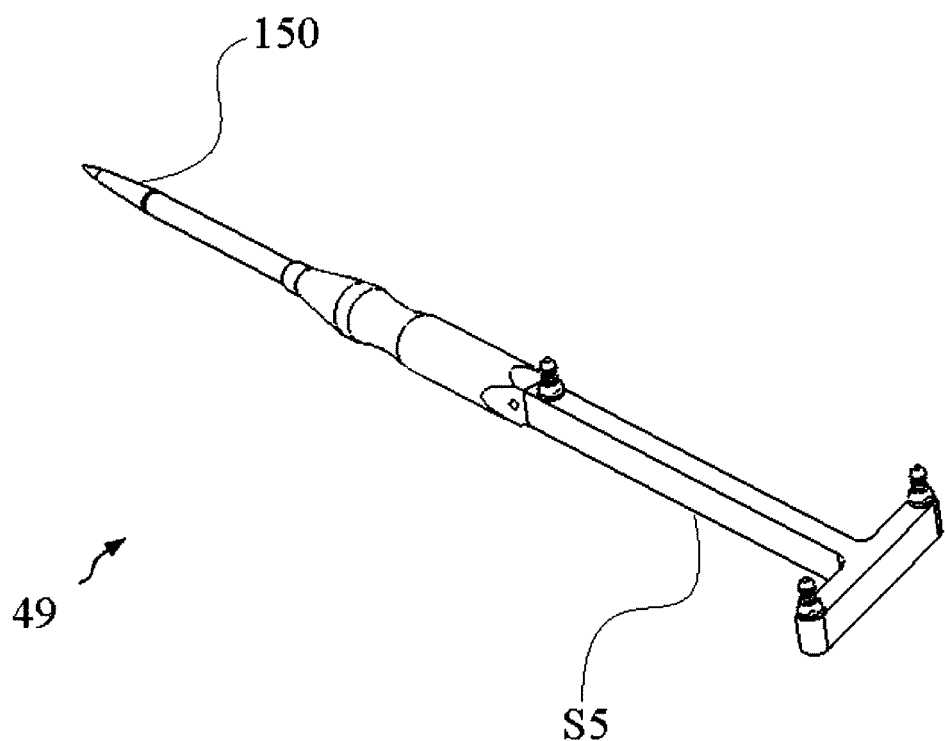
FIG. 7 is a perspective view of an embodiment of an instrument tracker according to the present invention.

The instrument tracker 49 is adapted to be coupled to an instrument 150 that is held manually in the hand of the user. The instrument 150 may be, for example, a probe, such as a registration probe. As shown in FIG. 7, the instrument tracker 49 may comprise a unique array S5 of markers (e.g., reflective spheres) formed integrally with the instrument 150 or affixed to the instrument 150 in any known manner, such as with mechanical hardware, adhesive, welding, a threaded connection, a clamping device, a clip, or the like. When the instrument tracker 49 is removably connected to the instrument 150, such as with a clip or a clamping device, the instrument tracker 49 should be calibrated to the instrument 150 to determine a relationship between the instrument tracker 49 and a geometry of the instrument 150. Calibration may be accomplished in any suitable manner, such as with a tool calibrator having a divot or a V-groove (e.g., as described in U.S. Patent Application Pub. No. US 2003/0209096, which is hereby incorporated by reference herein in its entirety). Knowing a geometric relationship between the array S5 and the instrument 150, the surgical system 10 is able to calculate a position of a tip of the instrument 150 in physical space. Thus, the instrument 150 can be used to register an object by touching a tip of the instrument 150 to a relevant portion of the object. For example, the instrument 150 may be used to register a bone of the patient by touching landmarks or points on the surface of the bone.

The tracking system 40 may additionally or alternatively include a mechanical tracking system. In contrast to the non-mechanical tracking system (which includes a detection device 41 that is remote from the trackers 43, 45, 47, and 49), a mechanical tracking system may be configured to include a detection device (e.g., an articulating linkage having joint encoders) that is physically connected to the tracked object. The tracking system 40 may include any known mechanical tracking system, such as a mechanical tracking system as described in U.S. Pat. Nos. 6,033,415, 6,322,567, and/or Pub. No. US 2006/0142657, each of which is hereby incorporated by reference herein in its entirety, or a fiber optic tracking system.

Figure 15:
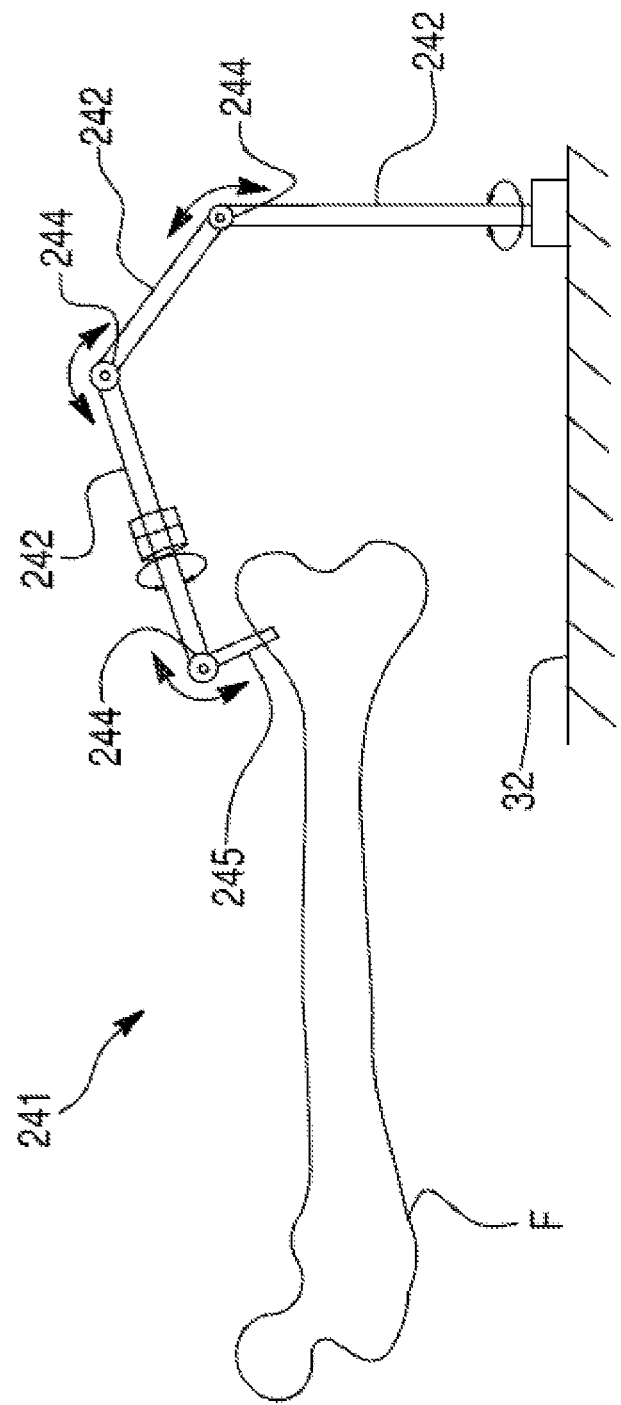
FIG. 15 is a view of an embodiment of a mechanical tracking system according to the present invention.

For example, as described in U.S. Pub. No. 2006/0142657, the tracking system 40 includes a mechanical tracking system having a jointed mechanical arm 241 (e.g., an articulated arm having six or more degrees of freedom) adapted to track a bone of the patient. As shown in FIG. 15, the arm 241 has a proximal end affixed to the base 32 of the haptic device 30 and a freely moveable distal end fixed to the femur F of the patient. Alternatively, the proximal end may be affixed to any other suitable location (such as, for example, to a rail of an operating table, a leg holder, etc.) but is preferably connected (e.g., directly or via a bracket) to the base 32 of the haptic device 30 so that the arm 241 moves globally with the haptic device 30. The distal end of the arm 241 includes an fixation device 245 adapted for rigid fixation to the femur F, such as, for example, a bone pin, bone screw, clamp, wearable device, surgical staple, or the like. The arm 241 is configured to have multiple degrees of freedom. For example, in one embodiment, as shown in FIG. 15, the arm 241 includes a plurality of links 242 connected at joints 244. Each joint 244 incorporates one or more position sensors (not shown) to track a pose of the arm 241. The position sensors may include any suitable sensor, such as, for example, the position sensors described above in connection with the arm 33 of the haptic device 30. In operation, as the femur F moves, the distal end of the arm travels with the femur F. The position sensors (and appropriate software) produce measurements of a pose of the distal end of the arm relative to the proximal end of the arm fixed to the haptic device 30. In this manner, motion of the femur F relative to the haptic device 30 is captured. The mechanical tracking system may also include a second arm that is identical to the arm 241 but is rigidly affixed to the tibia T to enable the tracking system to track motion of the tibia T. In this manner, the mechanical tracking system may be used to track the femur F and the tibia T so that the surgical system 10 can detect bone motion in real time during surgery. Using bone motion data in conjunction with appropriate software, the surgical system 10 can compensate for the bone motion in real time during surgery.

Figure 11:
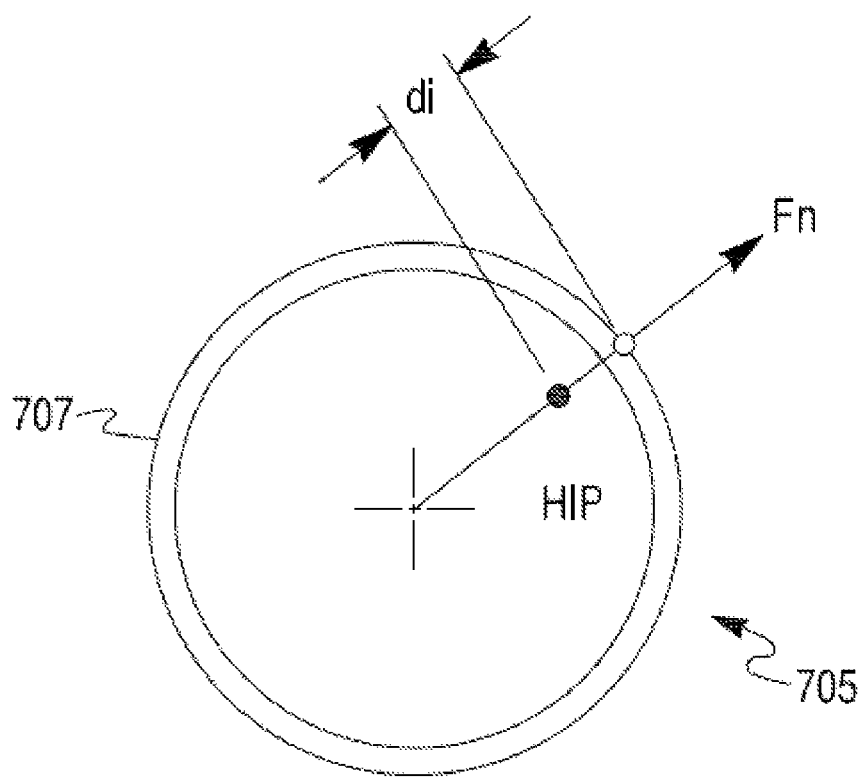
FIG. 11 is a representation of an embodiment of a 3D geometric haptic object according to the present invention.

In operation, the computing system 20, the haptic device 30, and the tracking system 40 cooperate to enable the surgical system 10 to provide haptic guidance to the user during a surgical procedure. The haptic guidance manifests as a result of the user's interaction with a virtual environment generated by a haptic rendering process. The haptic rendering process may include any suitable haptic rendering process, such as, for example, a haptic rendering process as described in U.S. Pat. No. 6,111,577, which is hereby incorporated by reference herein in its entirety. In a preferred embodiment, the haptic rendering process includes a haptic rendering algorithm as disclosed in the above-referenced Pub. No. US 2006/0142657 and/or U.S. patent application Ser. No. 11/646,204, filed Dec. 27, 2006, and incorporated by reference herein in its entirety. In the preferred embodiment, the surgical system 10 employs point-based haptic interaction where only a virtual point, or haptic interaction point (HIP), interacts with virtual objects in the virtual environment. The HIP corresponds to a physical point on the haptic device 30, such as, for example, a tip of the tool 50. The HIP is coupled to the physical point on the haptic device 30 by a virtual spring/damper model. The virtual object with which the HIP interacts may be, for example, a haptic object 705 (shown in FIG. 11) having a surface 707 and a haptic force normal vector $F_n$. A penetration depth $d_i$ is a distance between the HIP and the nearest point on the surface 707. The penetration depth $d_i$ represents the depth of penetration of the HIP into the haptic object 705.

Figure 10:
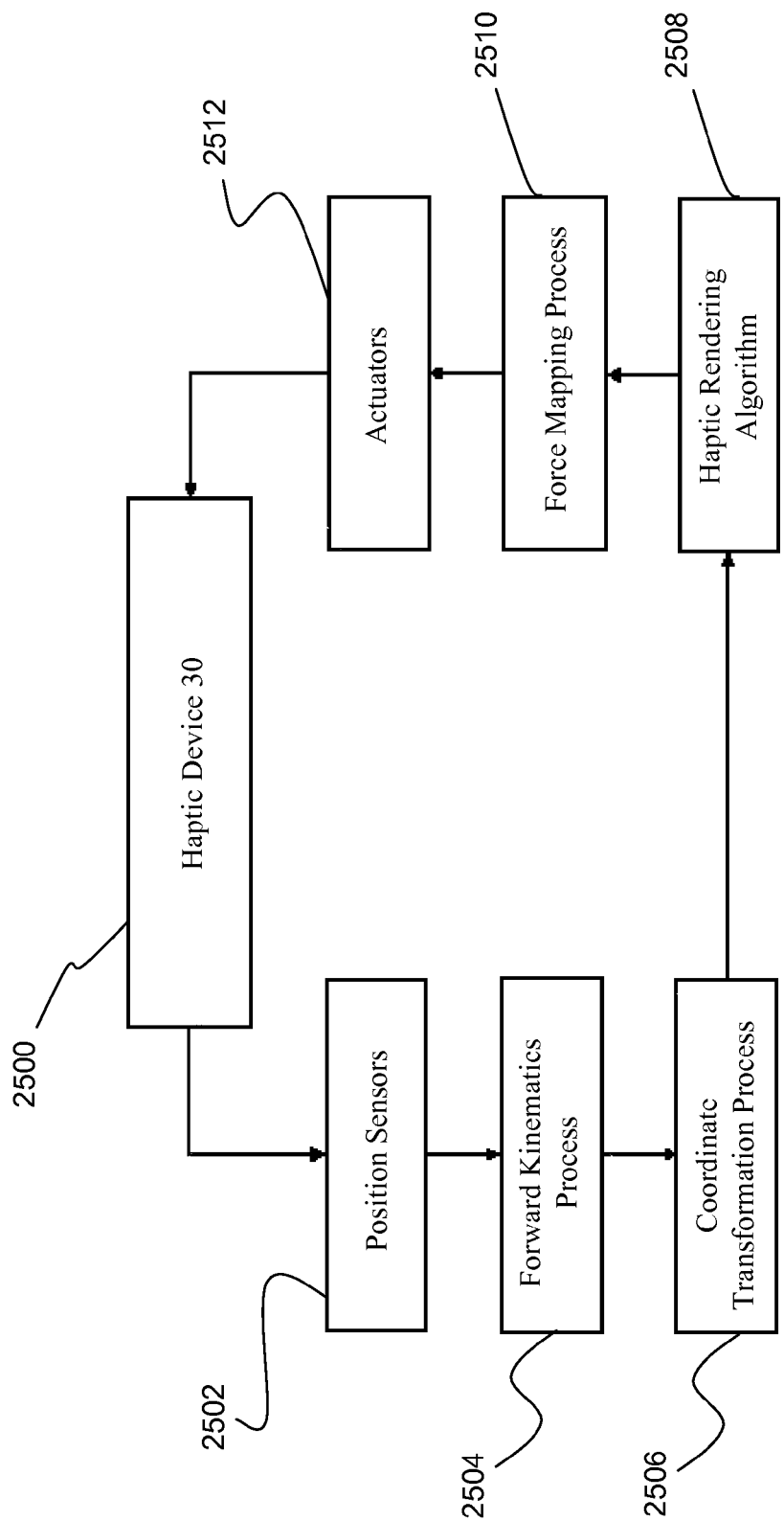
FIG. 10 is a block diagram of an embodiment of a haptic rendering process according to the present invention.

One embodiment of a haptic rendering process is represented generally in FIG. 10. In operation, position sensors (block 2502) of the haptic device 30 (block 2500) provide data to a forward kinematics process (block 2504). Output of the forward kinematics process is input to a coordinate transformation process (block 2506). A haptic rendering algorithm (block 2508) receives data from the coordinate transformation process and provides input to a force mapping process (block 2510). Based on the results of the force mapping process, actuators (block 2512) of the haptic device 30 are actuated to convey an appropriate haptic wrench (i.e., force and/or torque) to the user.

Figure 12A:
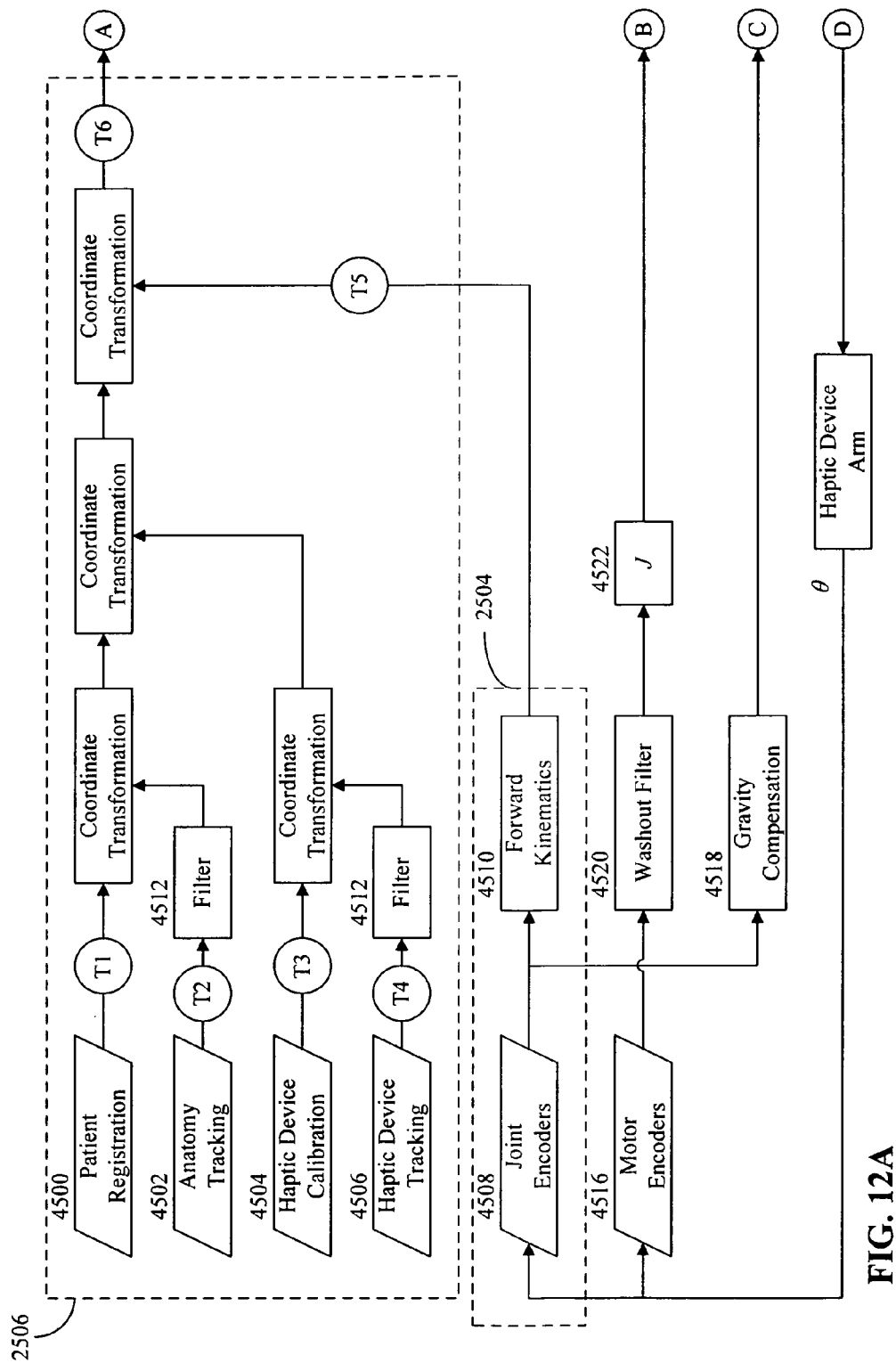
FIGS. 12A-B show a block diagram of an embodiment of a haptic rendering process according to the present invention.
Figure 12B:
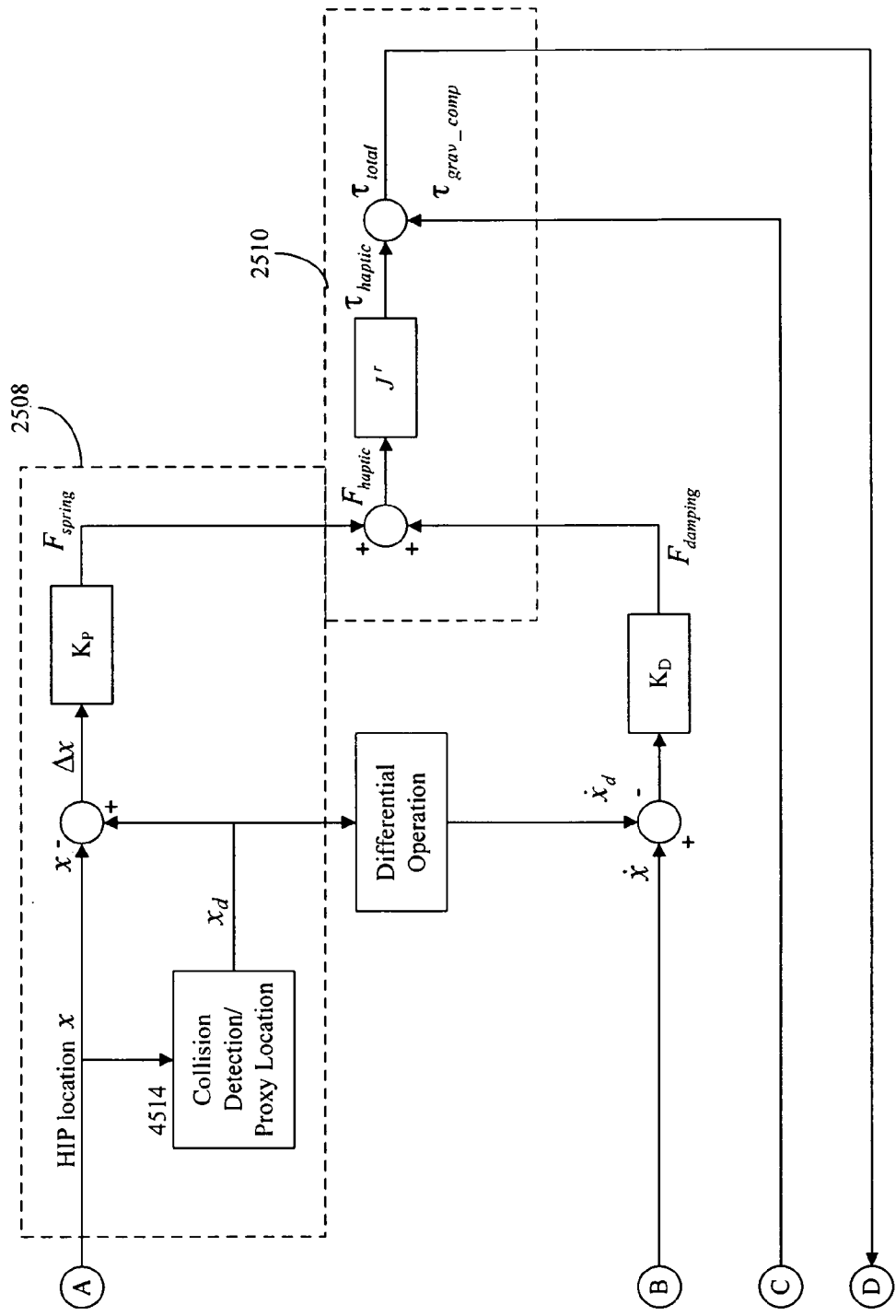

In one embodiment, the surgical system 10 includes a haptic rendering process as shown in FIGS. 12A-B. The dashed lines of FIGS. 12A-B correspond to the blocks of FIG. 10. As shown in FIGS. 12A-B, the coordinate transformation process 2506 utilizes registration and tracking information for the anatomy and the haptic device 30 and input from the forward kinematics process 2504 to determine coordinate transformations (or transforms) that enable the surgical system 10 to calculate a location of an endpoint of the haptic device 30 relative to specified portions of the anatomy. For example, the coordinate transformation process 2506 enables the surgical system 10 to calculate a location of the tip of the tool 50 relative to desired cut surfaces on the anatomy.

Figure 13:
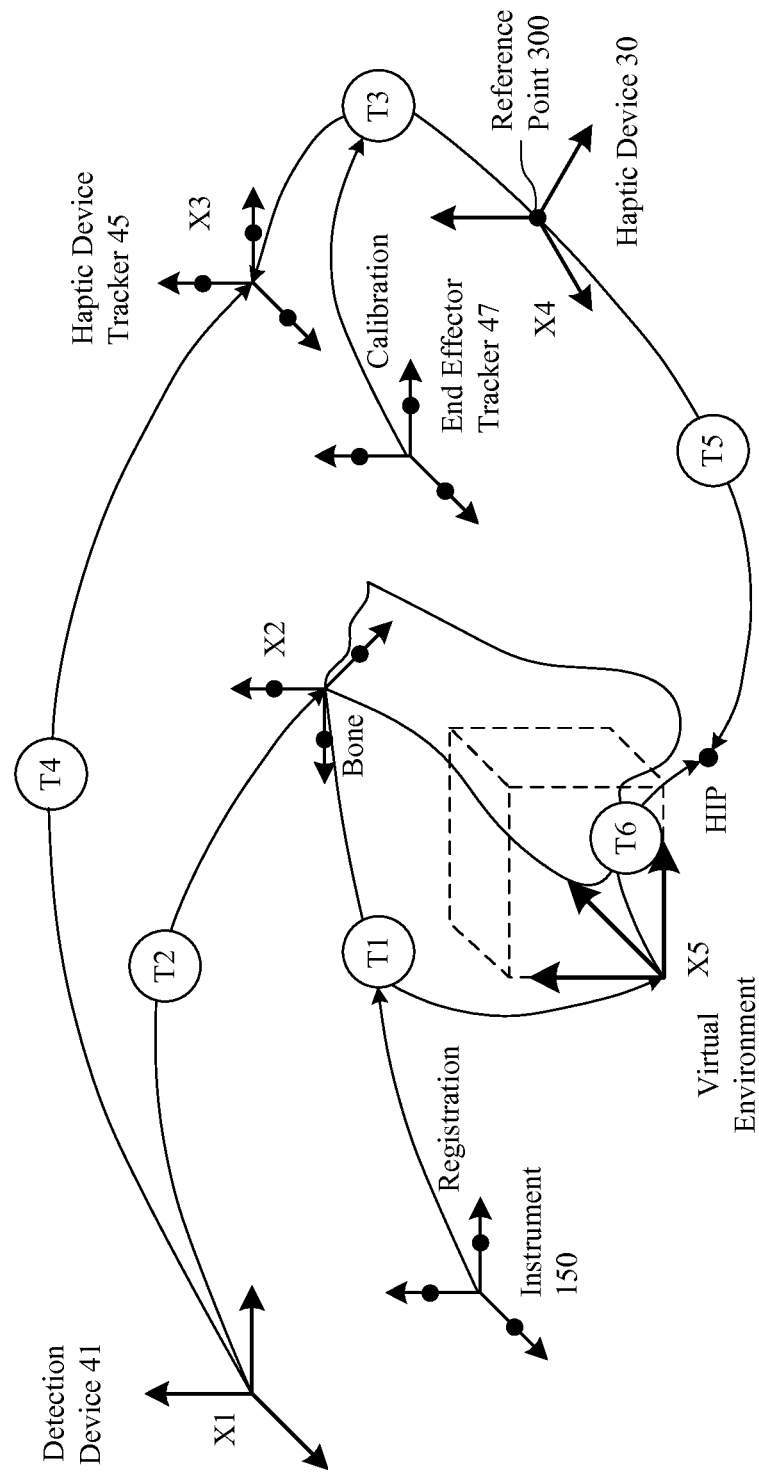
FIG. 13 is a pictorial representation illustrating coordinate systems and transformations according to the present invention.

As shown in FIG. 13, the coordinate transformation process 2506 includes defining various coordinate systems, including a first coordinate system $X_1$ associated with the detection device 41 of the tracking system 40, a second coordinate system $X_2$ associated with the anatomy (e.g., a bone or an anatomy tracker 43a or 43b affixed to the bone), a third coordinate system $X_3$ associated with the haptic device tracker 45, a fourth coordinate system $X_4$ associated with the haptic device 30 (e.g., the base 32 of the haptic device), and a fifth coordinate system $X_5$ associated with a virtual environment (e.g., a representation of the anatomy including a virtual (or haptic) object defining desired cut surfaces for installation of an implant). Coordinate transformations are then determined that enable coordinates in one coordinate system to be mapped or transformed to another coordinate system.

A first coordinate transformation $T_1$ (shown in FIGS. 12A-B and 13) is a transformation from the coordinate system of the anatomy (the second coordinate system $X_2$) to the coordinate system of the virtual environment (the fifth coordinate system $X_5$). Thus, in embodiments where the virtual environment includes a virtual object defining a shape of an implant, the transformation $T_1$ relates the physical anatomy to the desired cut locations for installation of the implant. As represented by block 4500 in FIG. 12A, the transformation $T_1$ may be determined by registering the physical anatomy of the patient to a representation of the anatomy (as described below) and positioning the virtual object relative to the representation of the anatomy. Positioning the virtual object relative to the representation of the anatomy may be accomplished, for example, using any suitable planning process, such as an implant planning process as disclosed in the above-referenced Pub. No. US 2006/0142657. For example, a virtual model that defines a virtual cutting boundary (such as a model of an implant to be implanted in the bone) may be positioned relative to the representation of the anatomy (such as an image of the anatomy) displayed on the display device 23.

A second coordinate transformation $T_2$ (shown in FIGS. 12A-B and 13) is a transformation from the coordinate system of the detection device 41 (the coordinate system $X_1$) to the coordinate system of the anatomy (the coordinate system $X_2$). As represented by block 4502 in FIG. 12A, the tracking system 40 outputs the transformation $T_2$ during a surgical procedure as the detection device 41 monitors motion of the anatomy. Because the detection device 41 continuously monitors the anatomy, the transformation $T_2$ is regularly updated to reflect motion of the anatomy.

A third coordinate transformation $T_3$ (shown in FIGS. 12A-B and 13) is a transformation from the coordinate system of the haptic device tracker 45 (the third coordinate system $X_3$) to the coordinate system of the haptic device 30 (the fourth coordinate system $X_4$). In this embodiment, the haptic device tracker 45 is coupled to the base 32 of the haptic device 30 via the arm 34 (as shown in FIG. 2A). Thus, the transformation $T_3$ relates the location of the haptic device tracker 45 to the base 32 of the haptic device 30. As represented by block 4504 in FIG. 12A, the transformation $T_3$ may be determined, for example, by performing the haptic device registration calibration as described below.

A fourth coordinate transformation $T_4$ (shown in FIGS. 12A-B and 13) is a transformation from the coordinate system of the detection device 41 (the coordinate system $X_1$) to the coordinate system of the haptic device tracker 45 (the coordinate system $X_3$). As represented by block 4506 in FIG. 12A, the tracking system 40 outputs the transformation $T_4$ during a surgical procedure as the detection device 41 monitors motion of the haptic device tracker 45. Because the detection device 41 continuously monitors the haptic device tracker 45, the transformation $T_4$ is regularly updated to reflect motion of the haptic device tracker 45.

A fifth coordinate transformation $T_5$ (shown in FIGS. 12A-B and 13) is a transformation that results from the forward kinematics process 2504. The forward kinematics process 2504 computes a Cartesian endpoint position of the arm 33 of the haptic device 30 as a function of joint angle. As represented by blocks 4508 and 4510 in FIG. 12A, the forward kinematics process 2504 receives input from position sensors in the joints of arm 33. Based on this input, the forward kinematics process 2504 computes a position of a distal end of the arm 33 relative to the base 32 of the haptic device 30. Based on a known geometric relationship between the tool 50 and the distal end of the arm 33, a position of the tip of the tool 50 relative to the base 32 of the haptic device 30 can then be computed. Because the position sensors continuously monitor joint position, the transformation $T_5$ is regularly updated to reflect motion of the arm 33.

A sixth coordinate transformation $T_6$ (shown in FIGS. 12A-B and 13) is obtained by multiplying the first through fifth coordinate transformations together in an appropriate sequence. In one embodiment, $T_6=T_1^{-1}T_2^{-1}T_4T_3^{-1}T_5$. The result of the transformation $T_6$ (represented by a variable x in FIG. 12B) is a location of a virtual point, or haptic interaction point (HIP), relative to the virtual environment. In this embodiment, the HIP corresponds to a location of a physical point on the haptic device 30 (e.g., the tip of the tool 50) relative to the desired cut surfaces defined by the virtual object. Because motion of the anatomy, the haptic device tracker 45, and the arm 33 of the haptic device 30 are continuously monitored, the transformation $T_6$ is regularly updated to reflect motion of the anatomy, the base 32 of the haptic device 30, and the arm 33 of the haptic device 30. In this manner, the surgical system 10 compensates for motion of objects during a surgical procedure.

One advantage of the present invention is that the surgical system 10 is able to compensate for motion of objects during the surgical procedure in a dynamic manner that is transparent to the user. Specifically, the surgical system 10 operates synchronously by continually monitoring motion of the anatomy, the haptic device tracker 45, and the arm 33 and continually updating the transformations $T_2$, $T_4$, and $T_5$ without interrupting operation of the haptic device 30. In contrast, conventional surgical systems typically operate asynchronously, for example, by requiring the user to stop and reset the system or reregister tracked objects when movement of a tracked object is detected. As a result, with conventional systems, the operation of the system may be interrupted or impeded when motion of a tracked object is detected. Although the present invention can operate synchronously without interrupting the operation of the haptic device 30, it is advantageous to occasionally restrict operation of the haptic device 30, for example, when the surgical system 10 detects abnormal motion, such as when a tracked object moves too fast and/or too far.

In one embodiment, a method of compensating for motion of objects during a surgical procedure includes (a) determining a pose of the anatomy; (b) determining a pose of the tool 50; (c) determining at least one of a position, an orientation, a velocity, and an acceleration of the tool 50; (d) associating the pose of the anatomy, the pose of the tool 50, and a relationship between the pose of the anatomy and the at least one of the position, the orientation, the velocity, and the acceleration of the tool 50; and (e) updating the association in response to motion of the anatomy and/or motion of the tool 50 without interrupting operation of the surgical device during the surgical procedure. The method may also include the step of providing haptic guidance, based on the relationship, to the user to constrain the user's manipulation of the surgical tool. The relationship may be based, for example, on a desired interaction between the anatomy and a position, an orientation, a velocity, and/or an acceleration of the tool 50. In one embodiment, the relationship is defined by a virtual object or parameter positioned relative to the anatomy and representing a desired location of an implant and/or cut surfaces for installing the implant. The step of associating the pose of the anatomy, the pose of the tool 50, and the relationship may be accomplished, for example, using registration processes, coordinate transformation processes (e.g., block 2506 of FIG. 10), and implant planning processes (e.g., as described in the above-reference Pub. No. US 2006/0142657). In one embodiment, the step of associating includes (a) defining a first transformation for transforming a coordinate system of the anatomy to a coordinate system of a representation of an anatomy; (b) defining a second transformation for transforming a coordinate system of the tool 50 to a coordinate system of the representation of the anatomy; and (c) associating the relationship with the coordinate system of the representation of the anatomy. To associate the relationship with the coordinate system of the representation of the anatomy, the user may, for example, position a virtual object relative to an image of the anatomy (e.g., as described in the above-reference Pub. No. US 2006/0142657). To enable the surgical system 10 to compensate for motion of objects during the surgical procedure, the step of updating the association may include updating the first transformation and/or the second transformation in response to motion of the anatomy and/or motion of the tool 50.

In this embodiment, the pose of the tool 50 is determined by determining a pose of a first portion of the haptic device 30 to which the tool 50 is coupled, determining a pose of a second portion of the haptic device 30, and calculating the pose of the tool 50 based at least in part on the poses of the first and second portions of the haptic device 30 and a known geometric relationship between the tool 50 and the first portion of the haptic device 30. In one embodiment, the first portion of the haptic device 30 comprises the distal end of the arm 33, and the second portion of the haptic device 30 comprises the base 32 of the haptic device 30. In another embodiment, the second portion of the haptic device 30 comprises an intermediate portion of the arm 33 (e.g., the segments 33a, 33b, or 33c). In one embodiment, rather than mounting the end effector tracker 35 to a distal end of the arm, the end effector tracker 35 could be mounted to an intermediate portion of the arm, such as the elbow. The step of determining the pose of the second portion of the haptic device 30 includes determining a pose of the haptic device tracker 45 (which is mounted on the second portion of the haptic device 30, e.g., to the base 32 or an intermediate portion of the arm 33). Because the pose of the tool 50 is determined based on the poses of the first and second portions of the haptic device 30 and because the surgical system 10 continually updates the poses of the first and second portions (e.g., based on joint encoder data and a position of the haptic device tracker 45), the pose of the tool 50 is updated to account for motion of the first and second portions. As a result, motion to the tool 50 is determined based on motion of the first and second portions. In this manner, the surgical system 10 is able to compensate for motion of objects during a surgical procedure.

In one embodiment, the tracking system 40 is a non-mechanical tracking system (e.g., as described above in connection with the tracking system 40) that operates at a different update rate than the haptic device 30. For example, the haptic device 30 may update at 2000 Hz while the tracking system 40 updates at 15-30 Hz. The lower update rate of the tracking system 40 limits the dynamic performance of the motion compensation because the 15-30 Hz updates are separated by ¹⁄₁₅ to ¹⁄₃₀ seconds during which time no tracking information is available. Additionally, higher frequency motions of a tracked object will not be present in the output data of the tracking system 40. One disadvantage of poor dynamic performance is that the surgical system 10 may not have sufficient data to move the haptic object precisely in sync with the physical anatomy. As a result, any cuts the surgeon makes may have reduced accuracy. For example, when the surgical system 10 is providing haptic guidance to guide the surgeon in cutting a planar bone surface with a spherical burr, momentary motion of one of the tracked objects combined with poor dynamic performance may result in divots or peaks in the final cut surface. The worse the dynamic performance, the larger the divots and peaks will be. If the bone cuts are for a cemented implants, small divots are acceptable because cement will simply fill the divots. For press fit implants, however, divots cause gaps between the implant and the bone that may potentially inhibit full in-growth of the bone into the implant. Peaks are less critical than divots because they can be easily removed with the burr but will increase the amount of time required to complete bone preparation.

For motion compensation applications, several techniques are beneficial in maximizing performance from tracking systems with dynamic performance issues. First, because of the different update rates, if the coordinate transformation process 2506 uses data directly from the tracking system 40, the desired cut surfaces defined by the virtual object move in abrupt steps in response to detected motion of the anatomy. As a result, a user manipulating the haptic device 30 may experience a rough or "jumpy" feeling when interacting with a haptic object. To address this problem, the surgical system 10 may include an interpolation or other appropriate filter (represented by the blocks 4512 in FIG. 12A). The filter also acts to reduce the output noise of the tracking system, which would otherwise result in the user feeling a vibration when interacting with a haptic object, or result in the cut having a rough surface. In a preferred embodiment, the filter is a 3rd order Butterworth filter with a cutoff frequency in a range of 5-10 Hz that samples data from the tracking system 40 at 2000 Hz and produces a filtered output. The filtered output reduces "jumpiness" of the cut surfaces relative to the anatomy from both the "stairstep" output from the tracking system and the noise inherent in the tracking system output updates. The Butterworth filter is characterized by a flat frequency in the passband and is easily designed using commonly available filter design software, such as Mathwork's Matlab Signal Processing Toolbox "butter" function, which outputs digital or analog filter coefficients based on the desired order and cutoff frequency. Using a higher order will result in sharper rolloff characteristics but require additional computation. A lower cutoff frequency will improve the filtering of the discrete tracking system updates and the tracking system noise but degrade the dynamic performance of the tracking. Alternatively, a Chebychev, Inverse Chebychev, Elliptic, Bessel (Thomson), or other filter can be used instead of a Butterworth filter. In another embodiment, a finite impulse response (FIR) filter can be used. An FIR filter can be designed to be "linear phase" so that all frequencies are delayed by the same amount, which makes compensation for filter delay easier. FIR filters are also well suited to "multi-rate" applications. For the tracking application of the present invention, interpolation would be used to convert the low frequency tracking signal to the high frequency rate of the haptic device 30. FIR filters are better than infinite impulse response (IIR) filters for multi-rate applications because FIR filters do not have feedback, i.e., their outputs are only a function of the input signal, not the output of the filter. Also, computation is only required for the low frequency signal samples, not for every high frequency sample.

In their traditional implementation, all of the above filters are designed for scalar input signals. However, the tracking system 40 will generally output multiple position and orientation signals. In a preferred embodiment, the filter 4512 receives the tracking system output, expressed as a homogenous transformation four by four size matrix that contains the position and orientation information. It is not desirable to filter the elements of this matrix directly because the result will not be a valid homogenous matrix and the orientation will not be filtered properly. Instead, the homogenous transformation is first converted to a three element position vector and a quaternion, which is a four element vector that represents the orientation information. For the small motions between samples, these seven values can then be independently filtered. The quaternion may be normalized before taking the filtered values and converting them back to a homogenous transformation, which is then output from the filter 4512.

In most cases, the position output of the tracking system 40 represents the position of the relevant tracked object at some point in the past. The latency is the time interval between the time when the tracking system 40 samples the tracked object's position and the time when the surgical system 10 receives this position output. This time interval may include processing time of the tracking system 40, communication delays, and a fraction or multiple of the sampling time of the tracking system 40. The filter 4512 adds additional latency based on the phase delay of the particular filter selected. These latency sources all combine to degrade the dynamic tracking performance and cause the haptic surfaces to lag behind the motion of their associated tracked objects. However, these latency values are usually known or can be measured or estimated fairly accurately. Thus, the latency effect can be partially compensated for. For example, if the combined latency of the tracking system 40 and the filter 4512 is $t_l$, then the filtered position output p may be corrected by $\Delta p = v \cdot t_l$. The velocity value v can be computed by a (possibly filtered) difference of successive position values or with a washout filter, as described below. In another embodiment, as is well known to those skilled in the art of control theory, a state estimator, state observer, or Kalman filter, which include a simple simulated model of the anatomy and/or the base 32 of the haptic device 30 and internally compute both the position and velocity of the tracked object, could be used to eliminate the latency of the filter 4512. Alternatively, the filter 4512 could be eliminated by utilizing a higher frequency tracking system, such as an encoder-based mechanical tracking system or high speed optical tracking system.

Some tracking systems, notably optical tracking systems, may not produce accurate outputs when tracked objects are moving relative to the camera (i.e., the detection device 41). Errors may result, for example, from motion blur caused by the exposure time or scanning rate of the camera. If the velocity of the tracked object is computed using one of the methods described above and an error model of the tracking system as a function of velocity and/or position is known or determined, these errors may be corrected by adding this error value to the filtered position output.

Dynamic performance of the tracking system 40 is only relevant if the haptic device 30 is capable of rendering a moving haptic object effectively. The haptic rendering capabilities of the haptic device 30 are impacted by the type of haptic control scheme used. The haptic device 30 may utilize any suitable haptic control scheme, such as, for example, admittance control, impedance control, or hybrid control. In an admittance control mode, the haptic device 30 accepts force input and yields position (or motion) output. For example, the haptic device 30 measures or senses a wrench at a particular location on the haptic device 30 (e.g., the user interface 37) and acts to modify a position of the haptic device 30. In an impedance control mode, the haptic device 30 accepts position (or motion) input and yields wrench output. For example, the haptic device 30 measures, senses, and/or calculates a position (i.e., position, orientation, velocity, and/or acceleration) of the tool 50 and applies an appropriate corresponding wrench. In a hybrid control mode, the haptic device 30 utilizes both admittance and impedance control. For example, a workspace of the haptic device 30 may be divided into a first subspace in which admittance control is used and a second subspace in which impedance control is used and/or both position and force inputs may be used to compute a force or position output. For example, in a substantially impedance controlled device, force inputs may be used to cancel out some of the natural friction of the system. In a preferred embodiment, the haptic device 30 is designed for impedance control, where the haptic device 30 reads the position and/or orientation of the user-manipulated surgical tool 50 and outputs an appropriate force and/or torque. Impedance control devices have the advantage of simplicity (no force sensor is required), better stability properties when the tool contacts physical objects (such as when cutting bone), and better performance when moving in free space. Admittance control devices, however, have an advantage in that they can render haptic objects with very stiff walls more easily than impedance control devices. With regard to motion tracking, impedance control devices are advantageous in that their performance is related to the open-loop force bandwidth and physical system dynamics. In contrast, the performance of an admittance control device depends on the closed-loop position control performance, which tends to be slower than the open-loop force and physical system dynamics.

Returning to the haptic rendering algorithm of FIG. 10, the HIP location, x, determined by the coordinate transformation process 2506 is provided as input to the haptic rendering algorithm 2508 as shown in FIG. 12B. A collision detection/proxy location haptic rendering process (represented by block 4514 in FIG. 12B) receives the HIP location, x, as input and outputs a desired location, $x_d$. The HIP location, x, is subtracted from the desired location, $x_d$, and the result, $\Delta x$, is multiplied by a haptic stiffness, $K_p$, to determine a position-dependent force command, $F_{spring}$. A desired velocity is also determined by taking the derivative, $\dot{x}_d$, of the desired location, $x_d$. The desired velocity is used in the computation of a damping force, $F_{damping}$.

As shown in FIG. 12B, the damping force, $F_{damping}$, is computed by subtracting the desired velocity, $\dot{x}_d$, from a Cartesian endpoint velocity, $\dot{x}$, of the haptic device 30 and multiplying the result by a damping gain, $K_D$. The Cartesian endpoint velocity, $\dot{x}$, is computed using data from position sensors in motors of the arm 33. As discussed above in connection with the haptic device 30, the arm 33 of the haptic device 30 preferably includes a cable transmission and position sensors in the motors and joints of the arm 33. In a preferred embodiment, joint encoders (represented by block 4508 of FIG. 12A) are used to obtain joint position measurements, and motor encoders (represented by block 4516 of FIG. 12A) are used to compute velocity measurements. The joint position measurements are used in the forward kinematics process 2504 to determine the transformation $T_5$ and are also provided as input to a gravity compensation algorithm (represented by block 4518 in FIG. 12A). The gravity compensation algorithm computes gravity torques, $\tau_{grav\_comp}$, required to counteract gravity loads on the segments of the arm 33 as a function of joint angle. In contrast, the motor position measurements are differenced and filtered to compute a motor velocity measurement. A washout filter (as represented by block 4520 in FIG. 12A) combines the differentiating and smoothing into one filter. The washout filter may be represented in the Laplace domain as:

$$F_{WOF}(s) = \frac{s}{\frac{s}{p} + 1}$$

where s is the Laplace transform variable, and where p determines the location of poles and in general should be located about two to three times faster than the fastest system pole. In one embodiment, the pole is placed at about 80 Hz. The filtered velocity is then multiplied by a Jacobian matrix, J, to obtain the Cartesian endpoint velocity, $\dot{x}$, of the haptic device 30.

The washout filter limits the high-frequency gain thereby limiting the amplification of noise inherent in a derivative or differencing operation and removing sampling-rate artifacts. The washout filter has a single parameter, p, which simplifies design and tuning of the filter, compared with separate velocity differencing and smoothing operations. The Laplace domain representation given above can be transformed into a discrete-time representation that is suitable for implementation on a digital computer using the well-known bilinear transform or z-transform. In an alternative embodiment to the washout filter, a simple differenced position signal can be filtered with a Butterworth or other filter described above to provide a velocity measure. Alternatively, a filtered position signal can be differenced and possibly filtered again using any of the filters described above.

As shown in FIG. 12B, $F_{damping}$ and $F_{spring}$ are summed in the force mapping process 2510 to obtain a desired haptic force, $F_{haptic}$. The desired haptic force is multiplied by a transposed Jacobian matrix, $J^T$, to computer motor torques, $\tau_{haptic}$, required to generate the desired haptic force. The gravity torques, $\tau_{grav\_comp}$, are added to the motor torques, $\tau_{haptic}$, to obtain a total torque, $\tau_{total}$. The haptic device 30 is commanded to apply the total torque, $\tau_{total}$, to the motors of the arm 33. In this manner the haptic rendering process enables the surgical system 10 to control the haptic device 30, which then responds to the commanded torques, user interaction, and interaction with the anatomy.

The haptic device 30 is preferably configured to operate in various operating modes. For example, the haptic device 30 may be programmed to operate in an input mode, a hold mode, a safety mode, a free mode, an approach mode, a haptic (or burring) mode, and/or any other suitable mode. The operating mode may be selected manually by the user (e.g., using a selection button represented graphically on the display device 23 or a mode switch located on the haptic device 30 and/or the computing system 20) and/or automatically by a controller or software process. In the input mode, the haptic device 30 is enabled for use as an input device to input information to the surgical system 10. When the haptic device 30 is in the input mode, the user may operate the haptic device 30 as a joystick or other input device, for example, as described above in connection with the end effector 35 and/or in U.S. patent application Ser. No. 10/384,078 (Pub. No. US 2004/0034282), which is hereby incorporated by reference herein in its entirety.

In the hold mode, the arm 33 of the haptic device 30 may be locked in a particular pose. For example, the arm 33 may be locked using brakes, control servoing techniques, and/or any other appropriate hardware and/or software for stabilizing the arm 33. The user may desire to place the haptic device 30 in the hold mode, for example, during an activity such as bone cutting to rest, confer with a colleague, allow cleaning and irrigation of the surgical site, and the like. In the safety mode, the tool 50 coupled to the haptic device 30 may be disabled, for example, by shutting off power to the tool 50. In one embodiment, the safety mode and the hold mode may be executed simultaneously so that the tool 50 is disabled when the arm 33 of the haptic device 30 is locked in position.

In the free mode, the end effector 35 of the haptic device 30 is freely moveable within the workspace of the haptic device 30. Power to the tool 50 is preferably deactivated, and the haptic device 30 may be adapted to feel weightless to the user. A weightless feeling may be achieved, for example, by computing gravitational loads acting on the segments 33a, 33b, and 33c of the arm 33 and controlling motors of the haptic device 30 to counteract the gravitational loads (e.g., as described below in connection with block 4518 of FIG. 12A). As a result, the user does not have to support the weight of the arm. The haptic device 30 may be in the free mode, for example, until the user is ready to direct the tool 50 to a surgical site on the patient's anatomy.

In the approach mode, the haptic device 30 is configured to guide the tool 50 to a target object, such as, for example, a surgical site, feature of interest on the patient's anatomy, and/or haptic object registered to the patient, while avoiding critical structures and anatomy. For example, in one embodiment, the approach mode enables interactive haptic positioning of the tool 50 as described in U.S. patent application Ser. No. 10/384,194 (Pub. No. US 2004/0034283), which is hereby incorporated by reference herein in its entirety. In another embodiment, the haptic rendering application may include a haptic object defining an approach volume (or boundary) that constrains the tool 50 to move toward the target object while avoiding sensitive features such as blood vessels, tendons, nerves, soft tissues, bone, existing implants, and the like. For example, as shown in FIG. 1, the approach volume may include the haptic object 300, which is substantially cone-shaped, funneling from a large diameter to a small diameter in a direction toward the target object (e.g., a proximal end of the tibia T or a distal end of the femur F). In operation, the user may freely move the tool 50 within the boundaries of the approach volume. As the user moves the tool 50 through the approach volume, however, the tapering funnel shape constrains tool movement so that the tool 50 does not penetrate the boundaries of the approach volume. In this manner, the tool 50 is guided directly to the surgical site.

Figure 8:
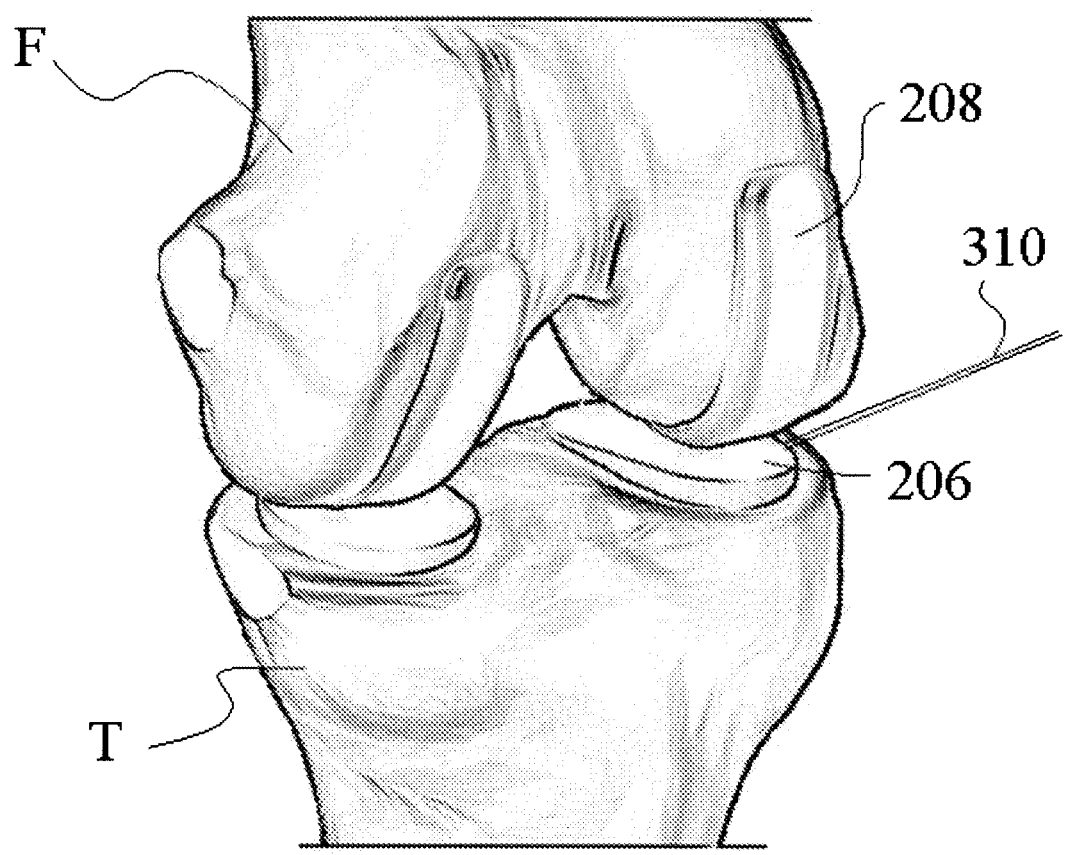
FIG. 8 is a perspective view of a femur and a tibia showing an embodiment of a graphical representation of a haptic object according to the present invention.

Another embodiment of the approach mode is shown in FIG. 8, which illustrates a haptic object 208 corresponding to a femoral component of a knee prosthesis and a haptic object 208 corresponding to a tibial component of the knee prosthesis. In this embodiment, the haptic rendering application creates a virtual object that represents a pathway from a first position to a second position. For example, the virtual object may include a haptic object 310, which is a virtual guide wire (e.g., a line) defining a pathway from a first position (e.g., a position of the tool 50 in physical space) to a second position that includes a target (e.g., a target object such as the haptic object 206 or 208). In the approach mode, the haptic object 310 is activated so that movement of the tool 50 is constrained along the pathway defined by the haptic object 310. The surgical system 10 deactivates the haptic object 310 when the tool 50 reaches the second position and activates the target object (e.g., the haptic object 206 or 208). The tool 50 may be automatically placed in the haptic (or burring) mode when the haptic object 206 or 208 is activated. In a preferred embodiment, the haptic object 310 may be deactivated to enable the tool 50 to deviate from the pathway. Thus, the user can override the haptic guidance associated with the haptic object 310 to deviate from the guide wire path and maneuver the tool 50 around untracked objects (e.g., retractors, lamps, etc.) that cannot be accounted for when the virtual guide wire is generated. Thus, the approach mode enables the user to quickly deliver the tool 50 to a target object while avoiding critical structures and anatomy. In the approach mode, power to the tool 50 is preferably deactivated so that the tool is not accidentally energized, for example, when the user is inserting the tool through an incision or navigating soft tissue in a joint. The approach mode generally precedes the haptic mode.

In the haptic (or burring) mode, the haptic device 30 is configured to provide haptic guidance to the user during a surgical activity such as bone preparation. In one embodiment, as shown in FIG. 8, the haptic rendering application may include the haptic object 206 defining a cutting volume on the tibia T. The haptic object 206 may have a shape that substantially corresponds to a shape of a surface of a tibial component. The haptic device 30 may enter the haptic mode automatically, for example, when the tip of the tool 50 approaches a predefined point related to a feature of interest. In the haptic mode, the haptic object 206 may also be dynamically modified (e.g., by enabling and disabling portions of a haptic surface) to improve performance of the haptic device 30 when sculpting complex shapes or shapes with high curvature as described, for example, in U.S. patent application Ser. No. 10/384,194 (Pub. No. US 2004/0034283), which is hereby incorporated by reference herein in its entirety. In the haptic mode, power to the tool 50 is activated, and the tip of the tool 50 is constrained to stay within the cutting volume to enable a precise bone resection. In another embodiment, an orientation constraint may be implemented, for example, by generating a slowly increasing force to draw the user inside the haptic volume if the user is in proximity to the haptic volume. Additionally, in this embodiment, the tool 50 can be disabled whenever the tool 50 is outside the haptic volume. In another embodiment, the tool 50 can be disabled unless the haptic device 30 is generating haptic feedback forces.

In operation, the surgical system 10 may be used for surgical planning and navigation as disclosed in the above-referenced Pub. No. US 2006/0142657. The surgical system 10 may be used, for example, to perform a knee replacement procedure or other joint replacement procedure involving installation of an implant. The implant may include any implant or prosthetic device, such as, for example, a total knee implant; a unicondylar knee implant; a modular knee implant; implants for other joints including hip, shoulder, elbow, wrist, ankle, and spine; and/or any other orthopedic and/or musculoskeletal implant, including implants of conventional materials and more exotic implants, such as orthobiologics, drug delivery implants, and cell delivery implants. Prior to performance of the procedure, the haptic device 30 is initialized, which includes a homing process, a kinematic calibration, and a haptic device registration calibration.

The homing process initializes the position sensors (e.g., encoders) in the arm 33 of the haptic device 30 to determine an initial pose of the arm 33. Homing may be accomplished in any known manner such as by manipulating the arm 33 so that each joint encoder is rotated until an index marker on the encoder is read. The index marker is an absolute reference on the encoder that correlates to a known absolute position of the joint. Thus, once the index marker is read, the control system of the haptic device 30 knows that the joint is in an absolute position. As the arm 33 continues to move, subsequent positions of the joint are calculated based on the absolute position and subsequent displacement of the encoder.

The kinematic calibration identifies errors in the kinematic parameters of the forward kinematics process 2504 (shown in FIG. 10). The forward kinematics process 2504 calculates a Cartesian position and orientation of the end effector 35 based on the measured joint angles of the arm 33 and the as-designed geometric properties of the haptic device 30 (e.g., length and offset of the segments 33a, 33b, and 33c of the arm 33). Due to manufacturing inaccuracies, however, the actual geometric properties of the haptic device 30 may deviate from the as-designed geometric properties, which results in error in the output of the forward kinematics process 2504. To determine the error, a kinematic calibration fixture is attached to the haptic device 30. In one embodiment, the fixture is a calibration bar having a fixed, known length. To perform the kinematic calibration, the end effector 35 is replaced with a calibration end effector having one or more ball joints (e.g., four ball joints arranged to form a cross, where a ball joint is located on each endpoint of the cross), and the arm 34 (on which the haptic device tracker 45 mounts) is removed and remounted in a horizontal configuration. A first end of the calibration bar is magnetically engaged with a ball joint on the arm 34, and a second end of the calibration bar is magnetically engaged with one of the ball joints on the calibration end effector. The calibration end effector is then moved to a plurality of positions (manually or automatically) as data is captured by the surgical system 10. After sufficient data has been collected (e.g., 100 data points), the second end of the calibration bar is magnetically engaged with a different ball joint on the calibration end effector. The process is repeated until data is captured for each ball joint on the calibration end effector. Using the existing kinematic parameters and measured joint angles, the data is used to calculate the length of the calibration bar. The computed length of the calibration bar is compared with the known actual length. The difference between the computed length and the known length is the error. Once the error is determined, the kinematic parameters can be adjusted to minimize aggregate error in the forward kinematics process 2504 using, for example, a numerical nonlinear minimization algorithm such as Levenberg-Marquardt.

The haptic device registration calibration establishes a geometric relationship or transformation between a coordinate system of the haptic device tracker 45 (e.g., the coordinate system $X_3$ shown in FIG. 13) and the coordinate system of the haptic device 30 (e.g., the coordinate system $X_4$ shown in FIG. 13). If the haptic device tracker 45 is fixed in a permanent position on the haptic device 30, the registration calibration is unnecessary because the geometric relationship between the tracker 45 and the haptic device 30 is fixed and known (e.g., from an initial calibration performed during manufacture or setup). In contrast, if the tracker 45 can move relative to the haptic device 30 (e.g., if the arm 34 on which the tracker 45 is mounted is adjustable), the registration calibration must be performed to determine the geometric relationship between the tracker 45 and the haptic device 30.

The registration calibration involves securing the haptic device tracker 45 in a fixed position on the haptic device 30 and temporarily affixing the end effector tracker 47 to the end effector 35, for example, with the clamp 1500 shown in FIG. 6A. To register the haptic device tracker 45 to the haptic device 30, the end effector 35 (and thus the end effector tracker 47) is moved to various positions in a vicinity of the anatomy (e.g., positions above and below the knee joint, positions medial and lateral to the knee joint) while the tracking system 40 acquires pose data for the trackers 45 and 47 relative to the tracking system 40 in each of the positions. Multiple data points are collected and averaged to minimize the effects of sensor noise and other measurement errors. Acquisition of the pose data during the registration calibration may be automatic. Alternatively, the user can initiate the collection of data using an input device such as a foot pedal.

In one embodiment, the user manually moves the end effector 35 to the various positions while the end effector 35 in the free mode. In another embodiment, the surgical system 10 controls the haptic device 30 to automatically move the end effector 35 to the various positions. In yet another embodiment, the haptic device 30 provides haptic guidance to guide the user in moving the end effector 35 to predefined points in the workspace of the haptic device 30. To improve the accuracy of the registration calibration, the predefined points are preferably located in a vicinity of the surgical site (e.g., close to the actual bone preparation site). The predefined points may include, for example, vertices of a shape, such as a two or three dimensional polytope (e.g., a polygon or polyhedron). In one embodiment, the shape is a cube centered at the relevant anatomy, such as the knee joint. The vertices are preferably displayed on the display device 23 along with an arrow indicating an allowable direction of motion for the end effector 35. One advantage of utilizing haptic guidance to guide the user in moving the end effector 35 to predefined points is that the user is able to move the end effector 35 to a plurality of positions in a repeatable fashion, which improves the accuracy of the registration calibration.

In addition to capturing data relating the pose of the trackers 45 and 47 to the tracking system 40, the surgical system 10 determines a pose of the end effector 35 relative to the haptic device 30 (e.g., relative to a reference point fixed in relation to the base 32 of the haptic device 30) based on data from the position sensors (e.g., joint encoders) in the arm 33. The surgical system 10 uses the data obtained during the registration calibration to calculate the geometric relationship between the haptic device tracker 45 and the coordinate frame of reference of the haptic device 30 (e.g., the coordinate system $X_4$ shown in FIG. 13, which has its origin at a reference point 300 fixed in relation to the base 32 of the haptic device 30).

In one embodiment, a transformation, $T_R^B$, of the haptic device tracker 45 relative to the base 32 of the haptic device 30 (e.g., relative to a reference point fixed in relation to the base 32 of the haptic device 30) is calculated as follows. As the end effector 35 is moved to the various positions, the surgical system 10 records (a) a position of the end effector tracker 47 (e.g., a known position on the end effector 35) relative to the tracking system 40, $P_C^E$, which is obtained from the tracking system 40; (b) a position and an orientation of the haptic device tracker 45 relative to the tracking system 40, $T_C^B$, which is obtained from the tracking system 40; and (c) a position of the end effector tracker 47 relative to the base of the haptic device 30, r, which is obtained from the joint encoders of the haptic device 30. If noise is present in the tracking system output, multiple samples can be taken for each end effector position. In the event the haptic device 30 moves during data sampling, the surgical system 10 can alert the user. Additionally, any affected data points should be thrown out because there will be latency between the data from the tracking system 40 and the data from the joint encoders of the haptic device 30. A position of the end effector tracker 47 relative to the haptic device tracker 45 is computed as $b_i = T_{B,i}{}^C P_{C,i}{}^E$ for each test location, i. A position of the end effector tracker 47 relative to the base 32 of the haptic device 30 at each test location, i, is denoted by $r_i$.

After data collection is complete, the transformation of the haptic device tracker 45 relative to the base 32 of the haptic device 30, (i.e., relative to a reference point on the base 32 of the haptic device 32), $T_R^B$, is separated into orientation and position terms, $$T_R^B = \begin{bmatrix} R_R^B & P_R^B \\ 0 & 1 \end{bmatrix}.$$

The orientation component $R_R^B$ is found by solving the equation $R_R^B \bar{b}_i = \bar{r}_i$. For this equation, the position error vectors $\bar{b}_i$ and $\bar{r}_i$ are computed according to $\bar{b}_i = b_i - b_m$ and $\bar{r}_i = r_i - r_m$, where $$b_m = \frac{\sum_{k=1}^{n} b_k}{n} \text{ and } r_m = \frac{\sum_{k=1}^{n} r_k}{n}.$$

A least-squares estimator using singular value decomposition is used to solve for $R_R^B$. The position vector $P_R^B$ can then be found from the equation $P_R^B = r_m - R_R^B b_m$. The transformation of the haptic device tracker 45 relative to the base 32 of the haptic device 30, $T_R^B$, can then be reconstructed according to $$T_R^B = \begin{bmatrix} R_R^B & P_R^B \\ 0 & 1 \end{bmatrix}.$$

After the registration calibration is complete, the end effector tracker 47 is removed from the haptic device 30. During surgery, the surgical system 10 can determine a pose of the tool 50 based on (a) a known geometric relationship between the tool 50 and the end effector 35, (b) a pose of the end effector 35 relative to the haptic device 30 (e.g., from the position sensors in the arm 33), (c) the geometric relationship between the haptic device 30 and the haptic device tracker 45 determined during the registration calibration, and (d) the global or gross position of the haptic device 30 (e.g., from the pose of the haptic device tracker 45 relative to the tracking system 40). The registration calibration need not be performed if the haptic device tracker 45 has not moved with respect to the haptic device 30 since the previous registration calibration and the previously acquired registration calibration data is still reliable.

In one embodiment, a method for performing the registration calibration includes (a) acquiring first data including at least one of a position and an orientation of a first object disposed on the haptic device 30 at a first location; (b) acquiring second data including at least one of a position and an orientation of a second object disposed on the haptic device 30 at a second location; (c) determining third data including at least one of a position and an orientation of the first object relative to the second location; and (d) determining at least one of a position and an orientation of the second object relative to the second location based at least in part on each of the first data, the second data, and the third data. The method may also include (e) moving the first object (e.g., the end effector tracker 47 disposed on the arm 33 of the haptic device 30) to a plurality of positions; (f) providing haptic guidance (e.g., force feedback) to guide the user in moving the first object to at least one of the plurality of positions; (g) acquiring the first data or the second data when the first object is in each of the plurality of positions; and (h) alerting the user if the first object, the second object, the first location, and/or the second location moves during acquisition of the first data, the second data, and/or the third data.

In one embodiment, the first object is the end effector tracker 47, and the second object is the haptic device tracker 45. In this embodiment, the steps of acquiring the first data and the second data include detecting the trackers 45 and 47 with the detection device 41. Alternatively, the second object may comprise one or more components of the tracking system 40, such as the detection device 41. As described above in connection with the end effector tracker 47, the end effector tracker 47 may be disposed at a location (e.g., the first location) on the haptic device 30 that includes a locating feature, such as a cylindrical feature of the tool 50 or the tool holder 51. In this case, the step of acquiring the first data may include determining a position and/or an orientation of a point and/or an axis of the cylindrical feature (e.g., the axis H-H shown in FIG. 3B or any point thereon). As described above in connection with the haptic device tracker 45, the haptic device tracker 45 (or the detection device 41) may be disposed at a location (e.g., the second location) on the haptic device 30, such as the base 32 (e.g., via the arm 34) on which the proximal end of the arm 33 is disposed. Alternatively, the haptic device tracker 45 (or the end effector tracker 47) may be located on an intermediate portion of the arm 33. During the haptic device registration calibration, the position and/or the orientation of the first object and the second object are fixed relative to the first and second locations, respectively. Fixation may be accomplished, for example, by clamping the end effector tracker 47 to the end effector 35 with the clamp 1500 and by fixing the position of the arm 34 on which the haptic device tracker 47 (or the detection device 41) is mounted. To determine the position and orientation of the first object relative to the second location (i.e., the third data), the surgical system 10 determines a configuration of the arm 33, for example, based on data from the joint encoders.

After the haptic device 30 is initialized, the surgeon can register the patient and the surgical tool 50 to a representation of the anatomy (such as a CT image) and perform a surgical procedure, such as preparing a bone to receive an implant based on a surgical plan. Registration, implant planning, and surgical navigation may be accomplished, for example, as described in the above-referenced Pub. No. US 2006/0142657. Throughout the surgical procedure, the surgical system 10 monitors a position of the bone to detect movement of the bone and makes corresponding adjustments to programs running on the computer 21 and/or the computer 31. For example, the surgical system 10 can adjust a representation (or image) of the bone in response to detected movement of the bone. Similarly, the surgical system 10 can adjust a representation (or image) of the surgical tool 50 in response to detected movement of the surgical tool 50. Thus, images of the bone and the surgical tool on the display device 23 move dynamically in real-time as the bone and the surgical tool 50 move in physical space. The surgical system 10 can also adjust a virtual object associated with the bone in response to detected movement of the bone. For example, the virtual object may define a virtual cutting boundary corresponding to a shape of a surface of the implant. As the bone moves, the surgical system 10 adjusts the virtual object so that the virtual cutting boundary moves in correspondence with the physical bone. In this manner, the surgeon can make accurate bone cuts even when the bone is moving. Additionally, adjustment of the images and the haptic object are transparent to the surgeon so that the surgeon's operation of the haptic device 30 is not interrupted during the surgical procedure.

To improve the safety of the surgical system 10, the surgical system 10 may include a safety feature adapted to constrain the user's operation of the tool 50 when an unsafe condition exists. For example, if an unsafe condition is detected, the surgical system 10 may issue a fault signal. A fault condition may exist if there is a system problem (e.g., a problem with the hardware or software), if an occlusion detection algorithm (e.g., as described below) detects an occluded condition, if a tracked object is moving too fast for the tracking system to process (e.g., when the patient's leg or the haptic device tracker 45 suddenly drops), when the tracking data is questionable, when the user is pushing too hard on the interface 37, and/or if the tool 50 is in an undesirable location. In one embodiment, the surgical system 10 is programmed to issue a fault if a relationship between the anatomy and a position, an orientation, a velocity, and/or an acceleration of the tool 50 does not correspond to a desired relationship and/or if the detection device 41 is unable to detect the position of the anatomy or the position of the surgical tool 51. In response to the fault signal, the surgical system 10 may impose a constraint on the haptic device 30. The constraint may include, for example, providing haptic guidance to the user (e.g., to prevent the user from moving the tool 50 in an unsafe manner) or changing the mode of the haptic device 30 (e.g., from a haptic mode to a free mode). In the preferred embodiment, the constraint is applied to the interface 37, which is both manipulated by the user and is proximal to the surgical site. For a teleoperated haptic device, which includes a "master" device that is operated by the surgeon and is typically remote from the surgical site and a "slave" device that holds the surgical tool proximal to the surgical site and is controlled by the master device, the constraint may be applied to the master device, the slave device, or both.

In one embodiment, a fault signal may be issued if the haptic rendering algorithm determines that a penetration depth of the tool 50 into a haptic boundary exceeds a predetermined threshold. The predetermined threshold may be, for example, a penetration depth in a range of about 1 mm to about 1.25 mm. In one embodiment, the haptic rendering algorithm determines whether the predetermined threshold is exceeded based on the haptic wrench (i.e., force and/or torque) being applied by the haptic device 30 to the user. For example, the haptic rendering algorithm may include a linear force versus position curve where the haptic force is set to about 20,000 N/m (or 20 N/mm). Thus, if the user moves the tip of the tool 50 to a penetration depth of 1 mm, the haptic device 30 outputs a haptic force of about 20 N. Similarly, if the user moves the tip of the tool 50 to a penetration depth of 1.25 mm, the haptic device 30 outputs a haptic force of about 25 N. In this embodiment, the fault signal is triggered when the haptic force reaches about 22.5 N, which corresponds to a penetration depth of about 1.125 mm. Additionally, a threshold haptic force value can be used to protect against the haptic device 30 generating excessively high forces. For example, haptic objects can be designed as independent primitives (e.g., simple geometric shapes) and combined during haptic rendering. If the cumulative effect of the primitives is undesirable (e.g., the total haptic force is too high), a fault signal can be issued.

In another embodiment, a fault signal may issue if rapid motion of the anatomy is detected as indicated, for example, by a velocity of the anatomy trackers 43a and 43b. Rapid motion may be caused, for example, when the anatomy shifts or a tracking element or the detection device 41 is bumped. In one embodiment, the fault signal issues if a velocity of the anatomy tracker 43a is greater than about 40 mm/s or a velocity of the anatomy tracker 43b is greater than about 26 mm/s. The indication of rapid motion may also be based on position (as opposed to velocity) such as when a position of the anatomy tracker 43a or 43b abruptly changes significantly. An abrupt change may be indicated, for example, if a change from the last known good position reported by the tracking system 40 to the current position reported by the tracking system 40 is greater than a predetermined threshold. In addition to rapid motion of the anatomy, the fault signal may issue if rapid motion of the haptic device tracker 45 is detected, such as when the haptic device tracker 45 has a high velocity or an abrupt change in position, which may indicate that the tracker 45 has been bumped or is not securely secured to the arm 34.

The surgical system 10 may have different levels or stages of faults. For example, in one embodiment, there are three stages of faults. The first fault stage applies when the tip of the tool 50 penetrates too deeply into or beyond a haptic boundary. The second fault stage applies when rapid motion of the anatomy is detected. The third fault stage applies when a system fault is present. The surgical system 10 responds to the fault stages by imposing a constraint on the haptic device 30. For example, the surgical system 10 may respond to the first fault stage by disabling the tool 50. The surgical system 10 may respond to the second fault stage by disabling both the tool 50 and the haptic guidance. Disabling the haptic guidance when rapid motion of the anatomy is detected (e.g., when the patient's leg slips off the operating table) advantageously prevents the virtual haptic surfaces that define the haptic cutting volume from moving with the falling bone and dragging the tool 50 along. In contrast, if the haptic surfaces are not disabled when the bone moves rapidly, the haptic surfaces will follow the bone and the haptic device 30 will exert a large force on the arm 33 to maintain the tool 50 within the falling haptic volume. As a result, the arm 33 will be dragged downward as the bone falls. Disabling the haptic guidance avoids this dangerous situation. The surgical system 10 may respond to the third fault stage by disabling the tool 50, shutting off power to the arm 33, and locking the brakes of the arm 33. In one embodiment, the surgical system 10 responds to a fault signal by disabling the tool 50 and placing the haptic device 30 in the free mode (rather than applying the brakes) so that the arm 33 does not pull or apply stress to the anatomy. In this manner, the surgical system 10 avoids damaging the anatomy by preventing the user from operating the tool 50 and/or the arm 33 when an unsafe condition exists.

In one embodiment, a safety feature of the surgical system 10 includes a tool disabling feature. For example, if the tool 50 is an electric tool, the surgical system 10 may include a relay disposed along an electrical connection between the tool 50 and a user input device for controlling the tool 50. For example, the relay may be located between a foot pedal and a tool control console (e.g., the ANSPACH® foot pedal and console described above in connection with the tool 50). Alternatively, the relay could be disposed along a control cable for a handheld instrument. In the case of a pneumatic tool, a pneumatic shutoff valve may be disposed in an air connection between the user input device and the tool motor. In lieu of a relay, the surgical system 10 could supply a digital or analog signal to a "disable input" port on the tool control console. In one embodiment, the surgical system 10 includes a relay that is closed under normal operating conditions so that the tool 50 is activated when the user depresses the foot pedal. If a fault condition is detected, the surgical system 10 issues a fault signal and commands the relay to open so that the tool 50 cannot be activated even when the user depresses the foot pedal. In another embodiment, the relay is a "normally open" relay so that the tool 50 will be remain shut off or disabled unless the tool 50 is specifically enabled by the surgical system 10. One advantage of a "normally open" relay is that if the haptic device 30 completely shuts down, the tool 50 will be disabled. Alternatively or in addition to disabling the tool 50 by commanding a relay or shut off valve, a fault condition may trigger the surgical system 10 to disable the tool 50 by commanding a power shutoff to the console or to the power supplies or amplifiers that drive the tool 50.

In one embodiment, a method of controlling the haptic device 30 based on the tool disabling features includes (a) enabling operation of the haptic device 30; (b) manipulating the haptic device 30 to perform a procedure on a patient; (c) determining whether a relationship between the anatomy of the patient and a position, an orientation, a velocity, and/or an acceleration of the tool 50 of the haptic device 30 corresponds to a desired relationship; and (d) issuing a fault signal and/or imposing a constraint on the haptic device 30 if the relationship does not correspond to the desired relationship or if the detection device 41 is unable to detect the anatomy or the tool 50. The relationship may be based, for example, on a desired interaction between the anatomy and the tool 50. In one embodiment, the relationship is defined by a virtual object positioned relative to the anatomy and representing a desired location of an implant and/or cut surfaces for installing the implant. The method may further include implementing control parameters for controlling the haptic device 30 to provide at least one of haptic guidance to the user and a limit on user manipulation of the surgical device based on the relationship. In one embodiment, in response to the fault signal, the surgical system 10 disables operation of the haptic device 30, locks a portion of the haptic device 30 in position, and/or places the haptic device 10 in a safety mode. In the safety mode, operation of and/or manipulation of the haptic device 30 may be impeded or constrained. To determine whether the relationship corresponds to the desired relationship, the surgical system 10 may, for example, determine whether a penetration depth of the tool 50 into a virtual boundary associated with the anatomy exceeds a desired penetration depth, determine whether the haptic device 30 has violated an operational constraint (e.g., a parameter generated by the haptic rendering algorithm), and/or determine whether the detection device 41 is able to detect a position of the anatomy and/or a position of the tool 50.

In another embodiment, a safety feature of the surgical system 10 includes an occlusion detection algorithm adapted to mitigate risk during a cutting operation in the event tracking elements (e.g., the trackers 43a, 43b, 45) associated with the haptic device 30 and/or the anatomy become occluded. An occluded state may exist, for example, when the detection device 41 is unable to detect a tracking element (e.g., when a person or object is interposed between the tracking element and the detection device 41), when a lens of the detection device 41 is occluded (e.g., by dust), and/or when reflectivity of markers on a tracking element is degraded (e.g., by blood, tissue, dust, bone debris, etc.). If an occluded state is detected, the occlusion detection algorithm alerts the user, for example, by causing a warning message to be displayed on the display device 23, an audible alarm to sound, and/or the generation of tactile feedback (e.g., vibration). The occlusion detection algorithm may also issue a control signal, such as a command to the surgical system 10 to shut off power to or otherwise disable the tool 50 or to impose a constraint on the haptic device 30 (e.g., providing haptic guidance, changing a mode of the haptic device 30, etc.). In this manner, the occlusion detection algorithm prevents the tool 50 from damaging the anatomy when the tracking system 40 is not able to accurately determine relative positions of the tool 50 and the anatomy.

In one embodiment, the occlusion detection algorithm considers a position of the tool 50 relative to a haptic boundary. In this embodiment, if the occlusion detection algorithm detects an occluded state, the surgical system 10 determines whether the tool 50 is touching a haptic boundary of a haptic object. If the tool 50 is not in contact with a haptic boundary at the time of an occlusion event, the occlusion detection algorithm disables the tool 50 and places the haptic device 30 in the free mode so that the tool 50 will move with the patient and, if necessary, can be withdrawn from the patient. When the occluded state ends (e.g., when all occluded trackers become visible), the surgical system 10 places the haptic device 30 in the approach mode so that the user may resume the procedure. In this manner, the occlusion detection algorithm permits the haptic boundary to be deactivated if the user isn't pushing against the haptic wall at the time of the occlusion event. In contrast, if the surgical system 10 determines that the tool 50 is touching the haptic boundary and/or exceeding the haptic boundary at the time of the occlusion event, the occlusion detection algorithm waits for a predetermined period of time (e.g., 1 second) to see if the occluded tracker(s) become visible. During this time, the tool 50 is disabled, and the user is alerted that the tracker(s) are occluded (e.g., via a visual, audible, or tactile signal). If the haptic device tracker 45 and the anatomy trackers 43a and 43b all become visible within the predetermined period of time, the haptic (or burring) mode is resumed. Otherwise, the haptic device 30 is placed in the free mode so that the tool 50 will move with the patient and, if necessary, can be withdrawn from the patient. As before, when the occluded state ends (e.g., when all occluded trackers again become visible), the surgical system 10 places the haptic device 30 in the approach mode so that the user may resume the procedure. One advantage of utilizing the predetermined period of time (or time interval) is that the occlusion detection algorithm allows the haptic wall to remain active during momentary occlusion events. Additionally, sudden removal of the haptic walls, which might result in sudden motion from the surgeon during cutting, is avoided. Additionally, if the occluded condition ceases to exist within the predetermined period of time, the low pass filter utilized for dynamic tracking (motion compensation) is reset to prevent the tracking system 40 from perceiving small motions as discontinuous motion.

Figure 14A:
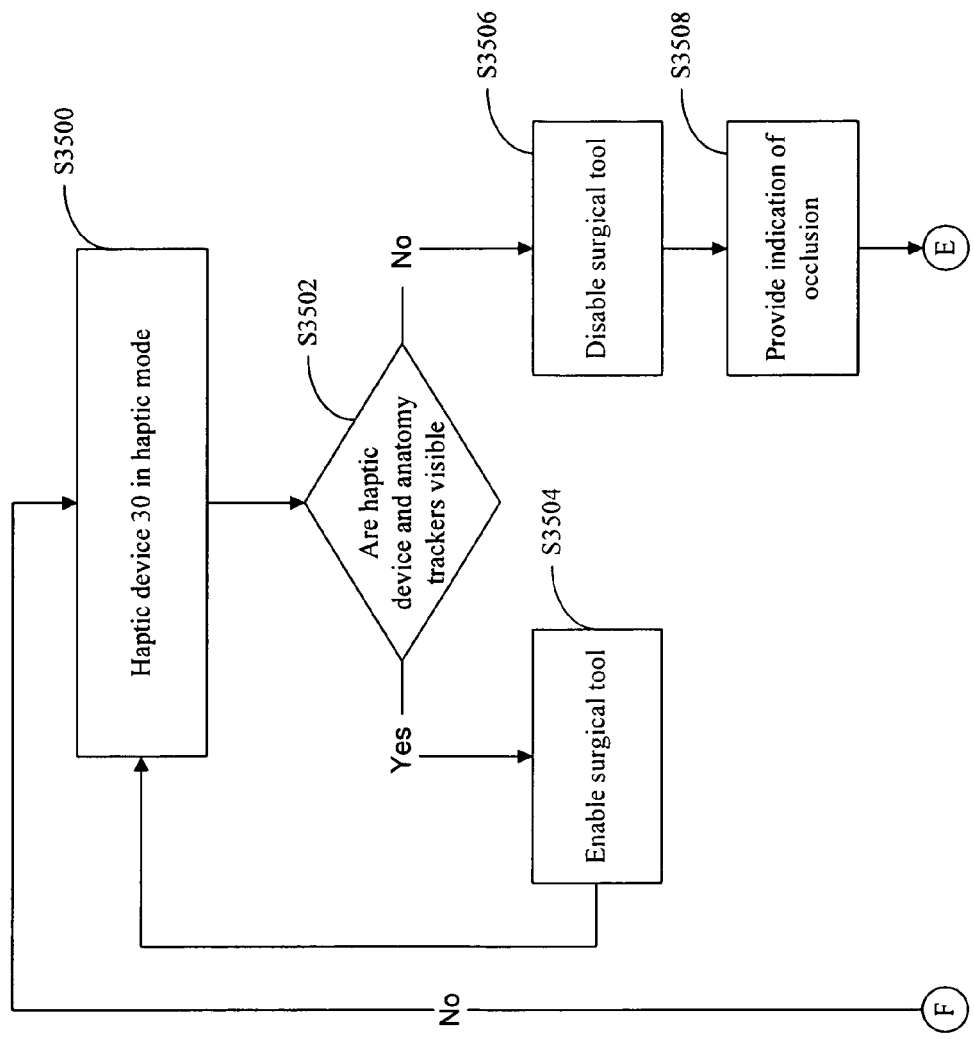
FIGS. 14A-B show a block diagram of an embodiment of an occlusion detection algorithm according to the present invention.
Figure 14B:
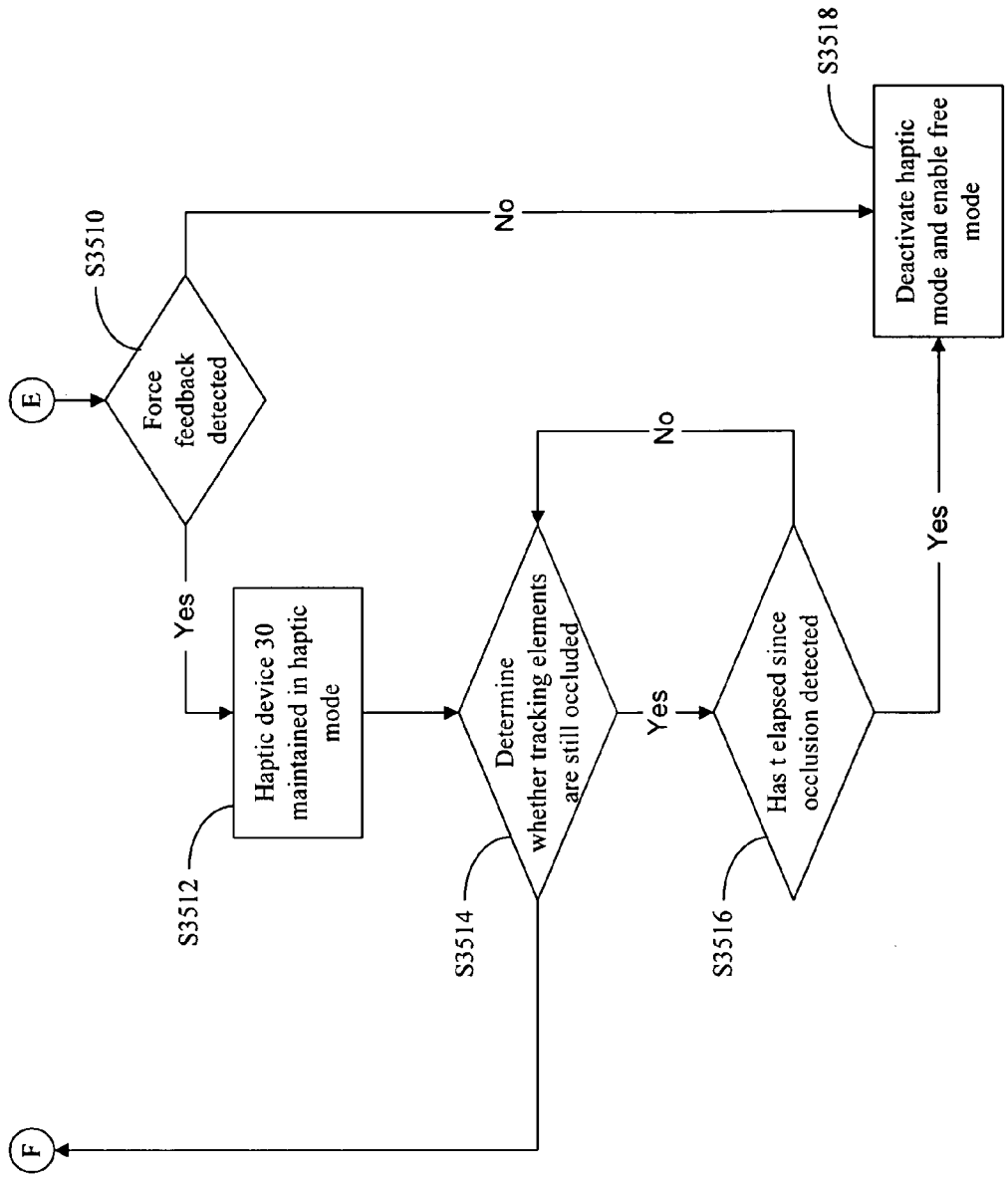

FIGS. 14A-14B show a diagram of an embodiment of an occlusion detection algorithm. In step S3500, the haptic device 30 is in the haptic (or burring) mode. In step S3502, the algorithm determines whether the haptic device tracker 45 and the relevant anatomy tracker are both visible (i.e., not occluded) to the detection device 41. The relevant anatomy tracker is the anatomy tracker associated with the bone of interest. Thus, for a knee replacement procedure, if the surgeon is preparing the femur F, the relevant anatomy tracker is the anatomy tracker 43a. Similarly, if the surgeon is preparing the tibia T, the relevant anatomy tracker is the anatomy tracker 43b. Although additional anatomy trackers may also be monitored, the occlusion detection algorithm preferably monitors only the relevant anatomy tracker to avoid unnecessary false triggers (e.g., triggers based on occlusion of trackers associated with portions of the anatomy other than the bone of interest). If both the haptic device tracker 45 and the relevant anatomy tracker are visible, the algorithm proceeds to step S3504 and enables the surgical tool 50. The surgical tool 50 may be enabled, for example, by providing power to the tool 50 so that the tool 50 can be activated by the user, such as by depressing a foot pedal. As shown in the loop of FIG. 14 (steps S3500, S3502, and S3504), as long as both trackers are visible, the haptic device 30 continues in the haptic mode with the surgical tool 50 enabled.

In contrast, if the detection device 41 in step S3502 is unable to detect the haptic device tracker 45 and/or the relevant anatomy tracker, the algorithm concludes that at least one of the trackers is occluded and proceeds to step S3506. The surgical tool 50 may be disabled, for example, by shutting off power to the tool 50 so that the tool 50 cannot be activated by the user even if the user attempts to activate the tool 50, such as by depressing a foot pedal. After the tool 50 is disabled, the algorithm the proceeds to step S3508 and provides an indication to the user that an occluded state exists. The indication may be any suitable signal, such as a visual signal on the display device 23, an audible signal (e.g., a beep, alarm, or other warning sound), a tactile signal (e.g., vibration), and/or a control signal (e.g., a control signal that commands the haptic device 30 to lock the arm 33 in position). In step S3510, the algorithm determines whether a haptic force is detected. A haptic force is detected, for example, when the haptic device 30 is providing force feedback to the user (e.g., haptic guidance and/or a limit on user manipulation of the arm 33). If a haptic force is not detected in step S3510, the algorithm proceeds to step S3518, deactivates the haptic mode, and enables the free mode. When the haptic device 30 is in the free mode, the tool 50 will move with the patient and, if necessary, can be withdrawn from the patient. When the occluded state ends, the surgical system 10 places the haptic device 30 in the approach mode so that the surgeon may resume the procedure.

In contrast, if a haptic force is detected, the algorithm proceeds to step S3512 and maintains the haptic device 30 in the haptic mode. In step S3514, the algorithm determines whether the haptic device tracker 45 and/or the relevant anatomy tracker is still occluded. If the trackers are not occluded, the algorithm returns to step S3500 where the haptic device 30 is maintained in the haptic mode 30 so that the surgeon may continue the procedure. In contrast, if at least one of the trackers is still occluded, the algorithm proceeds to step S3516 and determines whether a time t has elapsed since the occluded state was detected. The time t may be chosen based on the application. In one embodiment, the time t is about 1 second. If the time t has not elapsed, the algorithm returns to step S3514. If the time t has elapsed, the algorithm proceeds to step S3518, deactivates the haptic mode, and enables the free mode. When the haptic device 30 is in the free mode, the tool 50 will move with the patient and, if necessary, can be withdrawn from the patient. When the occluded state ends, the surgical system 10 places the haptic device 30 in the approach mode so that the surgeon may resume the procedure. In this manner, the occlusion detection algorithm advantageously limits the user's ability to activate the tool 50 when the surgical system 10 is not able to determine the relative positions of the haptic device 30 and the anatomy. As a result, the risk of damaging the anatomy is mitigated.

Another embodiment of the occlusion detection algorithm includes a method for controlling the haptic device 30 comprising the following steps: (a) detecting with the detection device 41 a first object comprising at least one of the anatomy and a tracking element associated with the anatomy; (b) detecting with the detection device 41 a second object comprising at least one of the haptic device 30 and a tracking element associated with the haptic device 30; and (c) providing an indication to the user if the detection device 41 is unable to detect the first object and/or the second object. The indication may be, for example, a signal, such as a visual, an audible, a tactile, and/or a control signal, or may be provided by disabling at least a portion of the haptic device 30, such as the tool 50. In one embodiment, the method includes imposing a constraint on the haptic device 30, such as limiting movement of at least a portion of the haptic device 30 (e.g., the arm 33, the tool 50) or limiting operation of the haptic device 30 (e.g., shutting off power to or otherwise disabling the tool 50, changing a mode of the haptic device, etc.). The constraint is preferably removed after a predetermined time interval (e.g., 1 second as discussed above in connection with step S3516 of FIG. 14B). The method may also include enabling the haptic device 30 only if the detection device 41 is able to detect both the first object and the second object.

In one embodiment, the occlusion detection algorithm determines whether the haptic device 30 is providing haptic guidance to the user and/or a limit on user manipulation of the haptic device 30. The haptic guidance and/or the limit on user manipulation may be based, for example, on a virtual boundary associated with the anatomy. If haptic guidance and/or a limit on user manipulation is being provided, the haptic guidance and/or the limit on user manipulation is preferably maintained to avoid damage to the anatomy (e.g., damage caused by sudden removal of the virtual boundary or haptic wall when the user is pushing against the virtual boundary with the tool 50). Accordingly, the virtual boundary is preferably maintained if a portion of the haptic device 30 (e.g., the tip of the tool 50) is proximate to, in contact with, or exceeding the virtual boundary. The method may also include deactivating the virtual boundary if the portion of the haptic device 30 is not interacting with the virtual boundary (e.g., if the tool 50 is not in contact with the virtual boundary or haptic wall). In this situation, because the user is not pushing against the virtual boundary with the tool 50, the tool 50 is not likely to damage the anatomy if the virtual boundary is suddenly removed. As a result, the risk of damaging the anatomy is reduced.

Thus, embodiments of the present invention provide a surgical system that is able to cooperatively interact with a surgeon to enable the surgeon to sculpt complex shapes in bone in a minimally invasive manner and that has the ability to dynamically compensate for motion of objects in the intraoperative environment in a manner that safeguards the patient and is substantially transparent to the surgeon.

A system and method for verifying calibration of a surgical device is disclosed in U.S. patent application Ser. No. 11/750,807, entitled System and Method for Verifying Calibration of a Surgical Device, by Louis Arata, Sherif Aly, Robert Van Vorhis, Sandi Glauser, Timothy Blackwell, Rony Abovitz, and Maurice R. Ferre, filed on May 18, 2007, the disclosure of which is hereby incorporated herein by reference in its entirety.

What is claimed is:

1. A system for calibrating a surgical device, comprising:
   an arm tracker configured to be tracked by a detection device and to provide data indicating at least one of a global position and orientation of the arm tracker, wherein the arm tracker is coupled to a distal portion of an arm of the surgical device;
   a device tracker configured to be tracked by the detection device and to provide data indicating at least one of a global position and orientation of the device tracker, wherein the device tracker is coupled to a base of the surgical device; and a computing system programmed to:
perform a registration calibration of the surgical device, the registration calibration comprising:
receiving, from the detection device, first data indicating the at least one of a global position and an orientation of the arm tracker when the arm tracker is disposed on the distal portion of the arm of the surgical device;
receiving, from the detection device, second data indicating the at least one of a global position and an orientation of the device tracker when the device tracker is coupled to the base of the surgical device;
receiving third data indicating at least one of a position and an orientation of the arm tracker relative to a reference point fixed in relation to the base;
determining, while tracking the arm tracker and the device tracker by the detection device, at least one of the position and the orientation of the device tracker relative to the reference point based at least on each of the first data, the second data, and the third data; and
alert a user if at least one of the arm tracker, the device tracker, the distal portion of the arm, and the reference point moves during the registration calibration while receiving at least one of the first data and the second data.

2. The system of claim 1, wherein the surgical device is configured to support a surgical tool coupled to the distal portion of the arm, and wherein the arm comprises an articulated linkage comprising at least one of a serial mechanism, a parallel mechanism, or a hybrid mechanism.

3. The system of claim 2, wherein a proximal portion of the arm is coupled to the base of the surgical device.

4. The system of claim 1, wherein the arm tracker includes a surface configured to abut a corresponding surface of the distal portion of the arm of the surgical device.

5. The system of claim 1, wherein the arm tracker includes a fixation device for attachment to the distal portion of the arm of the surgical device, and is configured such that the computing system can determine at least one of a point and an axis of the distal portion of the arm of the surgical device when the arm tracker is disposed on the distal portion of the arm of the surgical device.

6. The system of claim 5, wherein the fixation device is releasable, and the arm tracker is configured to be removed from the surgical device prior to a surgical procedure.

7. The system of claim 1, wherein the arm tracker comprises a first tracking element detectable by a detection device, and wherein the arm tracker has an as-designed geometric relationship with respect to at least one of a point and an axis of the surgical device when coupled to the distal portion of the arm of the surgical device.

8. The system of claim 7, wherein the device tracker comprises a second tracking element detectable by the detection device.

9. The system of claim 8, wherein the first tracking element comprises a first array of markers and the second tracking element comprises a second array of markers.

10. The system of claim 9, wherein the detection device comprises an optical tracking system configured to detect positions of the first and second arrays of markers.

11. The system of claim 10, wherein the first data is associated with the first array of markers and the second data is associated with the second array of markers.

12. The system of claim 11, wherein the first and second data comprise multiple data points, and wherein the computing system is further programmed to average the multiple data points to reduce effects of sensor noise.

13. The system of claim 12, wherein at least a portion of the third data is associated with readings provided by position sensors configured to detect a configuration of the arm.

14. The system of claim 13, wherein the position sensors comprise joint encoders configured to detect relationships between segments of the arm.

15. The system of claim 1, wherein a position of the device tracker is adjustable relative to the reference point.

16. The system of claim 15, wherein the device tracker is coupled to the base by way of an adjustable linkage configured to allow the device tracker to move with respect to the base and further configured to lock the device tracker in a fixed position with respect to the base.

17. The system of claim 1, wherein the computing system is further programmed to transform at least a portion of the first and second data from a first coordinate frame to a second coordinate frame.

18. A system for calibrating a surgical device, comprising:
a first object configured to be tracked by a detection device and to provide data indicating at least one of a global position and orientation of the first object wherein the first object is disposed on the surgical device;
a second object configured to be tracked by the detection device and to provide data indicating at least one of a global position and orientation of the second object wherein the second object is disposed on the surgical device; and
a computing system programmed to:
perform a registration calibration of the surgical device, the registration calibration comprising:
determining, using data from the detection device, first data including at least one of a position and an orientation of the first object when the first object is disposed on the surgical device at a first location;
determining, using data from the detection device, second data including at least one of a position and an orientation of the second object when the second object is disposed on the surgical device at a second location;
determining third data including at least one of a position and an orientation of the first object relative to a reference location; and
determining, while tracking the first object and the second object by the detection device, at least one of a position and an orientation of the second object relative to the reference location based at least on each of the first data, the second data, and the third data,
wherein the computing system is programmed to alert a user if at least one of the first object, the second object, the first location, and the second location moves during the registration calibration while determining at least one of the first data and the second data.

* * * * *